(12) United States Patent
Yue et al.

(10) Patent No.: US 7,985,736 B2
(45) Date of Patent: Jul. 26, 2011

(54) HIGH THROUGHPUT SCREEN UTILIZING NEWLY DISCOVERED INTRAMOLECULAR NEURONAL CALCIUM CHANNEL INTERACTIONS TO DISCOVER NEW ANALGESICS

(75) Inventors: David T. Yue, Baltimore, MD (US); Heather L. Agler, Baltimore, MD (US)

(73) Assignee: The John Hopkins University, Baltimore, MD (US)

( * ) Notice: Subject to any disclaimer, the term of this patent is extended or adjusted under 35 U.S.C. 154(b) by 373 days.

(21) Appl. No.: 11/793,058

(22) PCT Filed: Dec. 14, 2005

(86) PCT No.: PCT/US2005/045708
§ 371 (c)(1),
(2), (4) Date: May 21, 2008

(87) PCT Pub. No.: WO2006/066110
PCT Pub. Date: Jun. 22, 2006

(65) Prior Publication Data
US 2008/0279864 A1    Nov. 13, 2008

Related U.S. Application Data

(60) Provisional application No. 60/636,017, filed on Dec. 14, 2004.

(51) Int. Cl.
*A61K 38/16*  (2006.01)
*A61K 38/17*  (2006.01)
*C07K 14/00*  (2006.01)

(52) U.S. Cl. ............ 514/21.3; 514/17.4; 514/18.3; 530/300

(58) Field of Classification Search ............ None
See application file for complete search history.

(56) References Cited

U.S. PATENT DOCUMENTS

| | | | |
|---|---|---|---|
| 4,389,404 A * | 6/1983 | Zhorov et al. | 514/282 |
| 5,429,921 A | 7/1995 | Harpold et al. | |
| 5,792,846 A | 8/1998 | Harpold et al. | |
| 6,846,823 B2 * | 1/2005 | Landau et al. | 514/249 |
| 7,410,950 B2 * | 8/2008 | Garry et al. | 514/18 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) the Protein Folding Problem and Tertiary Structure Prediction. Birkhauser:Boston, pp. 491-495.*
Malmberg et al. (1995). Pain, 60:83-90.*

* cited by examiner

*Primary Examiner* — Christine J Saoud
*Assistant Examiner* — Jon M Lockard
(74) *Attorney, Agent, or Firm* — Edwards Angell Palmer & Dodge LLP; Peter F. Corless; Melissa Hunter-Ensor, Esq.

(57) ABSTRACT

The present invention relates to compositions to treat $Ca_V2$ disorders. The invention also relates to methods treating $Ca_V2$ disorders. The invention further relates to kits for treating $Ca_V2$ disorders in a subject. The invention further relates to methods of identifying novel treatments for treating $Ca_V2$ disorders in a subject.

12 Claims, 7 Drawing Sheets

SEQUENCE LISTING

<160> NUMBER OF SEQ ID NOS: 18

<210> SEQ ID NO 1
<211> LENGTH: 95
<212> TYPE: PRT
<213> ORGANISM: Homo sapiens

<400> SEQUENCE: 1

Met Val Arg Phe Gly Asp Glu Leu Gly Gly Arg Tyr Gly Gly Pro Gly
1               5                   10                  15

Gly Gly Glu Arg Ala Arg Gly Gly Ala Gly Gly Ala Gly Gly Pro
            20                  25                  30

Gly Pro Gly Gly Leu Gln Pro Gly Gln Arg Val Leu Tyr Lys Gln Ser
        35                  40                  45

Ile Ala Gln Arg Ala Arg Thr Met Ala Leu Tyr Asn Pro Ile Pro Val
    50                  55                  60

Lys Gln Asn Cys Phe Thr Val Asn Arg Ser Leu Phe Val Phe Ser Glu
65                  70                  75                  80

Asp Asn Val Val Arg Lys Tyr Ala Lys Arg Ile Thr Glu Trp Pro
                85                  90                  95

<210> SEQ ID NO 2
<211> LENGTH: 50
<212> TYPE: PRT
<213> ORGANISM: Homo sapiens

<400> SEQUENCE: 2

Lys Gln Ser Ile Ala Gln Arg Ala Arg Thr Met Ala Leu Tyr Asn Pro
1               5                   10                  15

Ile Pro Val Lys Gln Asn Cys Phe Thr Val Asn Arg Ser Leu Phe Val
            20                  25                  30

Phe Ser Glu Asp Asn Val Val Arg Lys Tyr Ala Lys Arg Ile Thr Glu
        35                  40                  45

Trp Pro
    50

<210> SEQ ID NO 3
<211> LENGTH: 40
<212> TYPE: PRT
<213> ORGANISM: Homo sapiens

<400> SEQUENCE: 3

Met Ala Leu Tyr Asn Pro Ile Pro Val Lys Gln Asn Cys Phe Thr Val
1               5                   10                  15

Asn Arg Ser Leu Phe Val Phe Ser Glu Asp Asn Val Val Arg Lys Tyr
            20                  25                  30

Ala Lys Arg Ile Thr Glu Trp Pro
        35                  40

<210> SEQ ID NO 4
<211> LENGTH: 5
<212> TYPE: PRT
<213> ORGANISM: Homo sapiens

<400> SEQUENCE: 4

Ser Thr Ser Val Ser
1               5

<210> SEQ ID NO 5

```
<211> LENGTH: 5
<212> TYPE: PRT
<213> ORGANISM: Homo sapiens

<400> SEQUENCE: 5

Ala Ala Ala Val Ala
1               5

<210> SEQ ID NO 6
<211> LENGTH: 5
<212> TYPE: PRT
<213> ORGANISM: Homo sapiens

<400> SEQUENCE: 6

Thr Val Ser Thr Ser
1               5

<210> SEQ ID NO 7
<211> LENGTH: 5
<212> TYPE: PRT
<213> ORGANISM: Homo sapiens

<400> SEQUENCE: 7

Ala Val Ala Ala Ala
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Leu Ser Gly Glu Phe Ser Lys
1               5

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Glu Ile Gly Glu Asp Arg Phe Ala Asp
1               5                   10

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Asp Arg Arg Cys
1               5

<210> SEQ ID NO 11
<211> LENGTH: 26
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 11

Met Val Arg Phe Gly Asp Glu Leu Gly Gly Arg Tyr Gly Gly Ala Gly
1               5                   10                  15

Gly Ala Glu Arg Ala Arg Gly Gly Gly Ala
            20                  25

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Arg Asp Gln Met Gln Gln Ser Ser Met Val Ser Lys Gly Glu
1               5                   10                  15

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Thr Leu Gly Met Asp Glu Leu Val Lys
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Leu Arg Ala Leu
1               5

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Cys Leu Thr Leu Asp Asn Val Val Arg Lys Tyr Ala Lys Arg Ile
1               5                   10                  15

Thr Glu Trp Pro
            20

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Ala Arg Thr Arg Ile Thr Glu Trp
1               5

<210> SEQ ID NO 17
<211> LENGTH: 126
<212> TYPE: PRT
<213> ORGANISM: Homo sapiens

<400> SEQUENCE: 17

Gly Glu Phe Ala Lys Glu Arg Glu Arg Val Glu Asn Arg Arg Ala Phe
1               5                   10                  15

Leu Lys Leu Arg Arg Gln Gln Gln Ile Glu Arg Glu Leu Asn Gly Tyr
                20                  25                  30

Leu Glu Trp Ile Phe Lys Ala Glu Glu Val Met Leu Ala Glu Glu Asp
            35                  40                  45

Arg Asn Ala Glu Glu Lys Ser Pro Leu Asp Val Leu Lys Arg Ala Ala
        50                  55                  60

Thr Lys Lys Ser Arg Asn Asp Leu Ile His Ala Glu Glu Gly Glu Asp
65                  70                  75                  80

Arg Phe Ala Asp Leu Cys Ala Val Gly Ser Pro Phe Ala Arg Ala Ser
                85                  90                  95

Leu Lys Ser Gly Lys Thr Glu Ser Ser Ser Tyr Phe Arg Arg Lys Glu
                100                 105                 110

Lys Met Phe Arg Phe Phe Ile Arg Arg Met Val Lys Ala Gln
                115                 120                 125

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 18

His His His His His His
1               5
```

HIGH THROUGHPUT SCREEN UTILIZING NEWLY DISCOVERED INTRAMOLECULAR NEURONAL CALCIUM CHANNEL INTERACTIONS TO DISCOVER NEW ANALGESICS

RELATED APPLICATIONS

This application claims priority from U.S. Provisional Application No. 60/636,017, filed Dec. 14, 2004, entitled, "A High Throughput Screen Utilizing Newly Discovered Intramolecular Neuronal Calcium Channel Interactions To Discover New Analgesics," which is incorporated herein by reference in its entirety.

BACKGROUND OF THE INVENTION

The underlying mechanism of opiates involves N-type ($Ca_V2.2$) $Ca^{2+}$ channels that drive synaptic transmission and thereby convey pain impulses to the central nervous system. The effects of opiates are then produced in substantial measure by receptor activation of G proteins that inhibit these very channels. N-type $Ca^{2+}$ channels figure prominently in conveying this sensory modality, and the renowned analgesia of opiates is produced in large measure via receptor activation of $G\beta\gamma$ to inhibit these channels. Classic opiates like morphine produce tolerance and threaten addiction at therapeutic doses, so adjunct strategies have been devised, such as toxin inhibition of N-type channels. Still, such alternate approaches also incur serious side effects. In the context of pain, known drug therapies have utility, but there are serious drawbacks to their use. Many existing drugs also have substantial adverse side effects in certain subjects leading to careful and expensive monitoring. Additionally, most existing drugs bring only temporary relief to sufferers and must be taken consistently on a daily or weekly basis for continued relief and with disease progression, the amount of medication needed to alleviate the pain may increase thus increasing the potential for side effects.

Genetic or pharmacological perturbations in ion channel function can have dramatic clinical consequences and toxic side affects such as arrhythmia and seizure which are triggered by certain drugs are due to interference with ion channel function. Thus, there is still a need for an effective and safe treatment to alleviate pain and to produce analgesia and for pharmaceutical compositions useful for the therapeutic modulation of ion channel activity and methods for developing such methods that have applications in treatment of many pathological conditions.

BRIEF SUMMARY OF THE INVENTION

The present invention provides novel compositions, methods, and kits to treat $Ca_V2$ disorders. The invention further provides methods of identifying novel treatments for treating $Ca_V2$ disorders in a subject.

According to one aspect, pharmaceutical compositions are presented and comprise a pharmaceutically effective amount of a $Ca_V2$ voltage gated calcium channel modulator effective to treat, prevent, ameliorate, reduce or alleviate a $Ca_V2$ related disorder or symptoms thereof.

In another aspect, the invention provides pharmaceutical compositions to enhance potency of an opioid agonist comprising a pharmaceutically effective amount of a $Ca_V2$ voltage gated calcium channel modulator.

According to one embodiment, the compositions may further include a pharmaceutically acceptable excipient.

In one embodiment, the compositions may further comprise an opioid analgesic. In a related embodiment, the opioid analgesic is any compound or composition acting, at least in part, by activation of G-protein coupled receptors leading to G-protein beta gamma subunit ($G\beta\gamma$) modulation of $Ca_V2$ channels. In another related embodiment, the opioid analgesic is morphine, hydrocodone, oxycodone, codeine, fentanyl, alfentanil, hydromorphone, meperidine, methadone, oxymorphone, propoxyphene, or tramadol.

In another embodiment, the $Ca_V2$ voltage gated calcium channel modulator interacts with a predominate modulation determinant of a $Ca_V2$ channel.

In certain embodiments, the $Ca_V2$ related disorder is a $Ca_V2.2$, $Ca_V2.1$, or $Ca_V2.3$ related disorder. In a related embodiment, the $Ca_V2$ channel is one or more of N—($Ca_V2.2$), P/Q-($Ca_V2.1$) or R-type ($Ca_V2.3$) calcium channels.

In one embodiment, the $Ca_V2$ voltage gated calcium channel modulator is selected from one or more of a small molecule, an anti-$Ca_V2$ antibody, an antigen-binding fragment of an anti-$Ca_V2$ antibody, a polypeptide, a peptidomimetic, a nucleic acid encoding a peptide, or an organic molecule.

In another embodiment, the antibody is one or more of a monoclonal antibody, a chimeric antibody, single chain antibody, an anti-idiotypic antibody, a humanized antibody, fully human antibody, or a primatized antibody.

In one embodiment, the $Ca_V2$ voltage gated calcium channel modulator is a peptide comprising $NT_B$ (45-95), $NT_B$ (56-95), full length $NT_B$ or a fragment or variant thereof.

In a related embodiment, the full length $NT_B$ comprises the sequence MVRFGDELGGRYGGPGGGERARGGGAG-GAGGPGPGGLQPGQRVLYKQSI AQRARTMALYN-PIPVKQNCFTVNRSLFVFSEDNVVRKYAKRITEWP (SEQ ID NO.: 1) or a fragment or variant thereof. In another related embodiment, the $NT_B$ (45-95) comprises the sequence KQSIAQRARTMALYN-PIPVKQNCFTVNRSLFVFSEDNVVRKYAKRITEWP (SEQ ID NO.: 2) or a fragment or variant thereof. In a further related embodiment, the $NT_B$ (56-95) comprises the sequence MALYNPIPVKQNCFTVNRSLFVFSEDNV-VRKYAKRITEWP (SEQ ID NO.: 3) or a fragment of variant thereof.

In a related embodiment, the $Ca_V2$ related disorder is pain (chronic, neuropathic, acute), trauma, migraine, neurological disorders (anxiety, stroke, psychoses, schizophrenia, depression, epilepsy), cardiovascular conditions (hypertension and cardiac arrhythmias), cancer, drug addiction, analgesic side effect, analgesic tolerance, diabetes, infertility, or a behavioral disorder.

In another embodiment, the behavioral disorder is one or more of anxiety, depression, or drug-related effect or behavior. In a related embodiment, the drug-related effect or behavior comprises an effect or behavior selected from the group consisting of a sedative effect, a hypnotic effect, an ataxic effect, drug reward, and drug consumption.

In one aspect, the invention provides, an isolated peptide comprising peptide comprising $NT_B$ (45-95), $NT_B$ (56-95), or full length $NT_B$ or fragments or variants thereof.

In another aspect, the invention provides, a vector encoding one or more of $NT_B$ (45-95), $NT_B$ (56-95), or full length $NT_B$ or fragments or variants thereof.

The invention also provides, in one aspect, an isolated cell that recombinantly expresses one or more peptides identified by $NT_B$ (45-95), $NT_B$ (56-95), or full length $NT_B$ or fragments or variants thereof.

The invention further provides, in one aspect, methods to treat, prevent, ameliorate, reduce or alleviate a $Ca_V2$ related disorder or symptoms thereof, comprising administering to a subject in need thereof a composition comprising a pharmaceutically effective amount of a $Ca_v2$ voltage gated calcium channel modulator. In one embodiment, the $Ca_v2$ voltage gated calcium channel modulator reversibly inhibits the voltage regulated calcium influx of a $Ca_v2$ channel.

In another embodiment, the method may further comprise administering one or more $G\beta\gamma$ polypeptides. In yet another embodiment, the methods may further comprise administering one or more opioid agonists. In certain embodiments, the opioid antagonist is from about 0.1 mg to about 300 mg.

In certain embodiments, the $Ca_v2$ related disorder is pain (chronic, neuropathic, acute), trauma, migraine, neurological disorders (anxiety, stroke, psychoses, schizophrenia, depression, epilepsy), cardiovascular conditions (hypertension and cardiac arrhythmias), cancer (e.g., breast, heart, lung, bone, skin, etc.), drug addiction, analgesic side effect, analgesic tolerance, diabetes (e.g., Type I or Type II), infertility (e.g., male or female), and a behavioral disorder.

In one embodiment, the composition further comprises one or more opioid agonists. In another embodiment, the opioid agonist is morphine, hydrocodone, oxycodone, codeine, fentanyl, alfentanil, hydromorphone, meperidine, methadone, oxymorphone, propoxyphene, or tramadol.

In another embodiment, the voltage gated calcium channel modulator is one or more of a small molecule, an anti-$Ca_v2$ antibody, an antigen-binding fragment of an anti-$Ca_v2$ antibody, a polypeptide, a peptidomimetic, a nucleic acid encoding a peptide, or an organic molecule.

In yet another embodiment, the $Ca_v2$ voltage gated calcium channel modulator is a peptide comprising $NT_B$ (45-95), $NT_B$ (56-95), full length $NT_B$ or fragments or variants thereof.

In one embodiment, the $Ca_v2$ voltage gated calcium channel modulator is administered prophylactically to a subject at risk of being afflicted a $Ca_v2$ related disorder.

In another embodiment, the $Ca_v2$ voltage gated calcium channel modulator enhances the interaction between calcium channels and $\beta\gamma$ subunits of a G protein.

In one embodiment, the composition further comprises a therapeutically effective amount of one or more of at least one anticonvulsant, non-narcotic analgesic, non-steroidal anti-inflammatory drug, antidepressant, glutamate receptor antagonist, nicotinic receptor antagonist, or local anesthetic. In a related embodiment, the anticonvulsant is lamotrigine, gabapentin, valproic acid, topiramate, famotodine, phenobarbital, diphenylhydantoin, phenyloin, mephenyloin, ethotoin, mephobarbital, primidone, carbamazepine, ethosuximide, methsuximide, phensuximide, trimethadione, benzodiazepine, phenacemide, acetazolamide, progabide, clonazepam, divalproex sodium, magnesium sulfate injection, metharbital, paramethadione, phenyloin sodium, valproate sodium, clobazam, sulthiame, dilantin, diphenylan, or L-5-hydroxytryptophan. In a related embodiment, the composition further comprises one or more nonsteroidal anti-inflammatory drugs selected from aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxican, sulindac, tolmetin, or zomepirac. In one embodiment, the composition further comprises tricyclic antidepressant that is amitriptyline, imipramine, desipramine or nortriptyline.

In another embodiment, the composition further comprises a glutamate receptor antagonist that is that is ketamine, MK801, memantine, dextromethorphan, dextrorphan, LY293558, LY382884, amantadine, agmatine, aptiganel, gavestinel, selfotel, 7-chlorokynurenate, MRZ 2/579, MDL 105,519, riluzole, CPP, AP5, APV, NBQX, CNQX or trans-ACPD.

In another embodiment, the composition further comprises a local anesthetic that is bupivicaine hydrochloride, chloroprocaine hydrochloride, dibucaine, dibucaine hydrochloride, etidocaine hydrochloride, lidocaine, lidocaine hydrochloride, mepivacaine hydrochloride, piperocaine hydrochloride, prilocaine hydrochloride, procaine hydrochloride, propoxycaine hydrochloride tetracaine, or tetracaine hydrochloride.

In one embodiment, the composition is administered to the subject orally, intravenously, intrathecally or epidurally, intramuscularly, subcutaneously, perineurally, intradermally, topically or transcutaneously.

In certain embodiments, the subject is a mammal, for example, dog, cat, cow, pig, rabbit, horse, goat, or a primate (e.g., non human and human primates).

In one embodiment, a $Ca_v2$ related disorder or symptom thereof is indicated by alleviation of allodynia, hyperalgesia, spontaneous burning pain, phantom pain, or hyperesthesia.

In another embodiment, the a $Ca_v2$ related disorder is pain associated with migraine, diabetes, diabetic neuropathy, shingles, burn injury, ophthalmic injury, oral nerve injury, sensory nerve injury or damage or damage, reflex sympathetic dystrophy (RSD), post-herpetic neuralgia, arthritis, cancer, or administration of a therapeutic agent.

According to another embodiment, the methods may further comprise obtaining the $Ca_v2.2$ voltage gated calcium channel modulator, for example, from a company manufacturing or selling the modulator or by making the modulator.

In one aspect, the invention provides, methods for enhancing the potency of an opioid agonist comprising administering to a subject in need thereof a composition comprising a therapeutically effective amount of a $Ca_v2.2$ voltage gated calcium channel modulator.

In one embodiment, a pharmaceutically effective amount of a $Ca_v2$ voltage gated calcium channel modulator.

In another embodiment, the method further comprise administering an opioid analgesic. The amount may be, for example, less than the amount that would be needed if the opioid analgesic were administered alone or without the $Ca_v2$ voltage gated calcium channel modulator.

In one embodiment, the $Ca_v2$ voltage gated calcium channel modulator interacts with a predominate modulation determinant of a $Ca_v2$ channel.

In another embodiment, the $Ca_v2$ voltage gated calcium channel modulator is selected from one or more of a small molecule, an anti-$Ca_v2$ antibody, an antigen-binding fragment of an anti-$Ca_v2$ antibody, a polypeptide, a peptidomimetic, a nucleic acid encoding a peptide, or an organic molecule.

In another embodiment, the $Ca_v2$ voltage gated calcium channel modulator is a peptide comprising $NT_B$ (45-95), $NT_B$ (56-95), full length $NT_B$ or a fragment or variant thereof.

The invention also provides, in one aspect, methods for identifying lead compounds for a pharmacological agent useful in the treatment of a $Ca_v2$ related disorder comprising contacting a predominant modulation determinant of a calcium channel with a test compound, and measuring channel modulation.

In one embodiment, the methods may further comprise identifying the predominant modulation determinant of a calcium channel.

In another embodiment, the predominant modulation determinant of a calcium channel is identified by a FRET two-hybrid, yeast two-hybrid, phage display, and channel structure-function screen.

In one embodiment, the channel modulation is measured by one or more of compound-state analysis, $K_{d\ EFF}$, G/Q analysis, DF facilitation, channel activation status, and current recording. In another embodiment, the channel modulation is measured by customized electrophysicalogical analyses, e.g., compound-state analysis, $K_{d\ EFF}$, G/Q analysis, DF facilitation, channel activation status, current recording.

According to one embodiment, the methods may further comprise contacting a modified calcium channel with the test compound.

In another embodiment, the modified calcium channel is a chimeric channel, and a deletion mutant.

According to one embodiment, the methods may further comprise activating the calcium channel prior to or after contacting it with a test compound. In another embodiment, the calcium channel is activated with a Gβγ protein. In one embodiment, the test compounds is one or more of a peptide corresponding to the predominant modulation determinant of a calcium channel, a small molecule, an antibody or fragment thereof, and nucleic acid or a library thereof.

According to one aspect, the invention provides methods for identifying lead compounds for a pharmacological agent useful to treat, prevent, ameliorate, reduce or alleviate a $Ca_v2$ related disorder or symptoms thereof, comprising contacting a cell or other membrane-encapsulated space comprising a calcium channel with a candidate pharmacological agent, wherein the calcium channel has a defined predominant modulation determinant; and determining a test amount of voltage regulated calcium influx as a measure of the effect of the lead compound. In certain embodiments, a test amount of voltage regulated calcium influx which is less than a control amount indicates that the candidate pharmacological agent is a lead compound for a pharmacological agent to treat a $Ca_v2.2$ disorder.

According to one embodiment, the methods may further comprise loading the cell or other membrane-encapsulated space with a calcium-sensitive compound which is detectable in the presence of calcium, wherein the calcium-sensitive compound is detected as a measure of the voltage regulated calcium influx.

In another embodiment, the pharmacological agent that specifically reduces voltage regulated calcium influx mediated by a N-type calcium channel is an agent that reduces N-type calcium channel current densities in nociceptive neurons.

According to one embodiment, the methods may further comprise providing Gβγ polypeptides.

In one embodiment, the methods may further comprise contacting a control cell or other membrane-encapsulated space comprising a control calcium channel with a candidate pharmacological agent, wherein the control calcium channel has a defined predominant modulation determinant.

In another embodiment, the control calcium channel is a truncated $Ca_v2.2$ calcium channel or a chimeric calcium channel.

In one embodiment, the control calcium channel is one or more of N-terminus truncated N-type $Ca_v2.2$ calcium channel, N-terminus replaced with $α_{1B}$ with $α_{1C}$, α1B channel with a C-tail truncation at 1877, $α_{1B}$ channel with a C-tail truncation at 1877 fused to YFP, deletion of $NT_B$ residues of the $α_{1B}$ subunit ($α_{1b(Δ56-90)BbBBBb}$), an N-type $Ca_v2.2$ calcium channel with a replacement of the I-II loop of $α_{1B}$ with that of $α_{1C}$.

In one aspect, the invention provides, methods for modulating calcium influx in a neuronal cell mediated by a $Ca_v2$ channel, comprising: contacting the neuronal cell with an amount of an $Ca_v2.2$ voltage gated calcium channel modulator effective to inhibit calcium influx in the mammalian cell.

In one aspect, the invention provides, kits comprising: a) an $Ca_v2$ channel voltage gated calcium channel modulator and a pharmaceutically acceptable carrier and b) instructions for use.

In another aspect, the invention provides, transgenics non-human animals comprising an over-expressed $NT_B$ peptide or a fragment or variant thereof.

In one aspect, the invention provides, use of a transgenic animal to test therapeutic agents.

In one aspect, the invention provides, methods for screening a therapeutic agent to treat, prevent, ameliorate, reduce or alleviate a $Ca_v2$ related disorder or symptoms thereof, comprising, administering a test agent to a mouse having an over-expressed $NT_B$ peptide, and measuring modulation of pain thresholds or calcium influx.

In one embodiment, a decrease in the influx of calcium indicates that the test agent may be useful in treating a $Ca_v2$ disorder.

In one embodiment, a change in the calcium influx, wherein a decrease in the influx indicates that the agent may be useful in treating a $Ca_v2$ related disorder.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

Other embodiments of the invention are disclosed infra.

Figure 10:
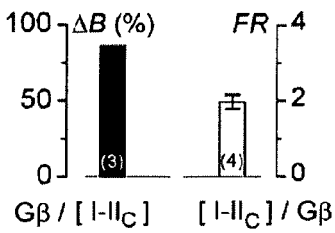

FIG. 10 shows the conductance conversion factor for yeast- and FRET two-hybrid assays. Format for yeast two-hybrid assays (left) as in FIG. 2C, with error bars smaller than can be resolved. For yeast two-hybrid, we used G$\beta_1$/pGADT7 as in FIG. 2C, and I-II$_C$ (436-554)/pGBKT7. FRET assays (right) by acceptor photo-bleaching methodology. I-II$_C$-YFP construct as in FIG. 2Ec. For GB in FRET assays, G$\beta_1$ was co-transfected with CFP-G$\gamma_{2mut}$, where CFP was appended to the N-terminal end of G$\gamma_2$, and the prenylation site at residue 68 has been mutated from C to A, allowing for a cytoplasmic disposition of both interacting partners in the FRET two-hybrid assay.

Figure 11:
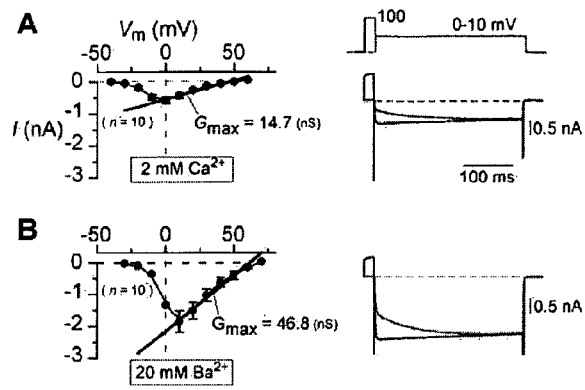

FIG. 11 shows that engineered muscarinic receptor exhibits little desensitization. Determination of a conversion factor: (A) Left, the average facilitated current-voltage (I-V) relationship for $\alpha_{1B}$ channels in 2 mM Ca$^{2+}$. Right, a typical current at 0 mV from an $\alpha_{1B}$ channel in 2 mM Ca$^{2+}$. (B) Left, the average facilitated I-V relationship for the same cells as in panel A, using 20 mM Ba$^{2+}$. Right, a 10 mV step in 20 mM Ba$^{2+}$ from the same cell shown in the right half of panel A. For comparison, a voltage step to 10 mV (in 20 mM Ba$^{2+}$) is used to compare to the voltage step to 10 mV in panel A (2 mM Ca$^{2+}$), since they both represent the peak current in the respective solutions.

Figure 12:
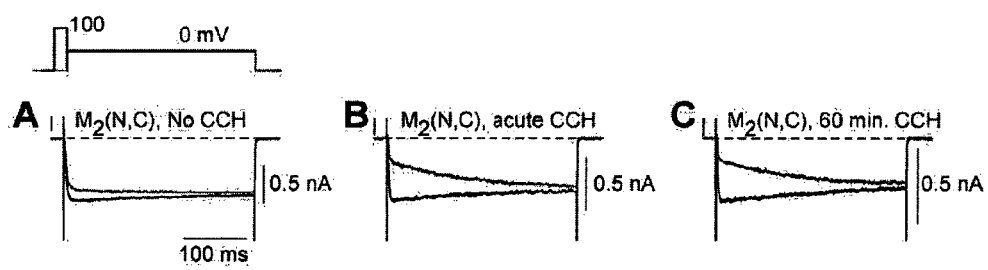

FIG. 12 details the construction of $\alpha_{1B\Delta(56-90)BbBBBb}$, ancillary data establishing that NT$_B$ residues 56-95 are critical for producing constitutive inhibition of N-type channels during G-protein activation, sub-mapping I-II$_B$ for interaction with NT$_B$. (A) Response of $\alpha_{1B}$ channels to receptor-mediated activation of G proteins, as produced by engineered m2R. Exemplar cell during voltage steps to 0 mV, with and without a prepulse to 100 mV (black and gray traces, respectively). Recordings at room temperature in all panels. (B) Exemplar cell after acute application of 50 μM carbachol in bath, showing obvious signs of G-protein modulation. (C) Traces from different exemplar cell than in panel A. Cell was incubated with carbachol for 60 minutes in the incubator at 37° C., then transferred to the patch-clamp rig for recording at room temperature. Cell was maintained in carbachol during whole-cell current recording. Even after 60 minutes in carbachol at 37° C., modulation is still clearly present at comparable levels to that in panel B.

Figure 13:
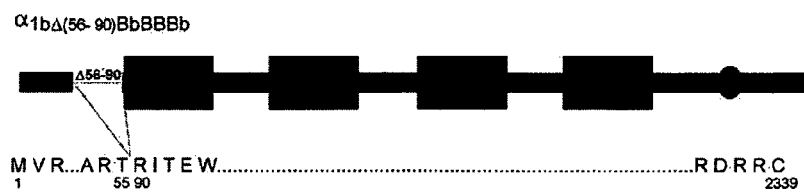

FIG. 13 Critical amino-acid boundaries for α1bΔ(56-90) BbBBBb. Amino acids 56 through 90 were deleted using overlap extension PCR.

Figure 14:
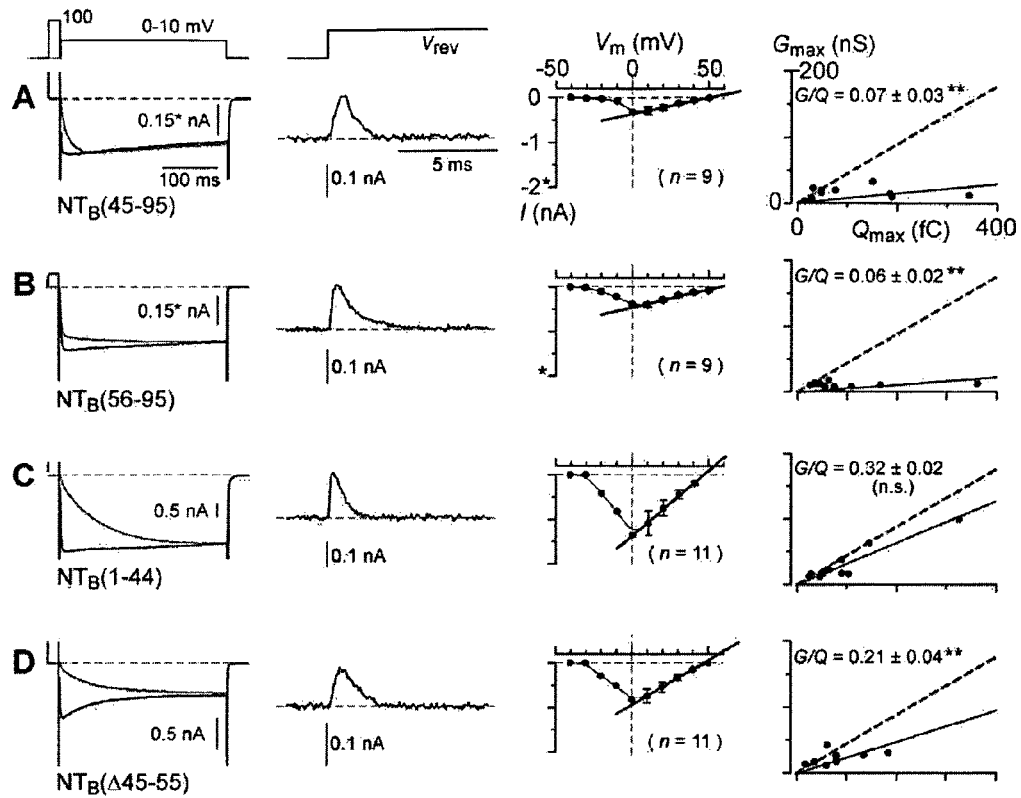

FIG. 14 shows the G/Q analysis for various NT$_B$ subdomains co-expressed with N-type channels and G$\beta\gamma$. Format identical to that in FIG. 3. Dashed lines represent the relation for control N-type channels expressed alone. *Currents originally measured in 20 mM Ba$^{2+}$, followed by conversion to equivalent 2 mM Ca$^{2+}$ traces.

Figure 15:
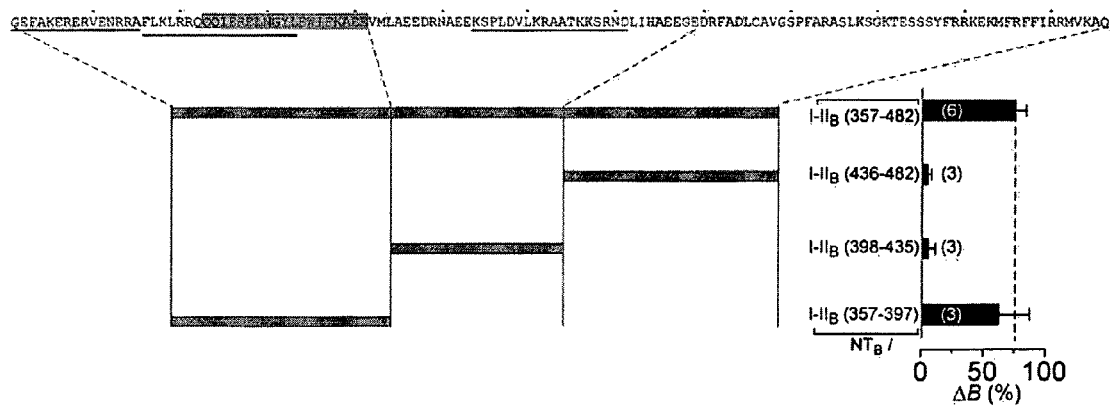

FIG. 15 shows yeast two-hybrid mapping of I-II$_B$ subdomains required for interaction with NT$_B$ element. Top, amino-acid sequence for the I-II$_B$ (residues 357-482), N-terminal end at the left. Boxed region, AID interaction region with auxiliary B subunit (Van Petegem et al., 2004). Underline, peptide segments found to inhibit G-protein modulation (Zamponi et al., 1997). Below, left, various I-II$_B$ segments (pGADT7) paired with NT$_B$ (pGBKT7) in hybridization assays. Below, right, ΔB index for high-stringency interaction, format as in FIG. 2D.

DETAILED DESCRIPTION

This invention is based, in part, on the discovery of that the G-protein gated interaction of the amino terminus (NT$_B$ region) and I-II loop of the $\alpha_{1B}$ subunit of Ca$_v$2.2 channels is the predominant molecular determinant of Ca$_v$2.2 channel inhibition by G-protein βγ subunits. The present invention provides novel compositions, methods, and kits to treat Ca$_v$2 disorders. The invention further provides methods of identifying novel treatments for treating Ca$_v$2 disorders in a subject.

The Ca$_v$2 family of voltage-gated calcium channels (presynaptic calcium channels) consist of 3 main subtypes Ca$_v$2.1 (P or Q-type calcium currents), Ca$_v$2.2 (N-type calcium currents) and Ca$_v$2.3 (R-type calcium currents). These currents are found almost exclusively in the central nerves system (CNS), peripheral nerves system (PNS) and neuroendocrine cells and constitute the predominant forms of presynaptic voltage-gated calcium current. Presynaptic calcium entry is modulated by many types of G-protein coupled receptors (GPCRs) and modulation of Ca$_v$2 channels is a widespread and highly efficacious means of regulating neurotransmission. The subunit composition of the Ca$_v$2 channels is defined by their $\alpha_1$ subunit ($\alpha_1$2.1, $\alpha_1$2.2 and $\alpha_1$12.3, also known as $\alpha_{1A}$, $\alpha_{1B}$ and $\alpha_{1E}$ respectively), which forms the pore and contains the voltage-sensing gates; the β subunit; and $\alpha_2\delta$ and γ subunits.

Ca$_v$2.2 channels are found in the periphery and mediate catecholamine release from sympathetic neurons and adrenal chromaffin cells. Some forms of hypertension result from elevated sympathetic tone and Ca$_v$2.2 modulators could be particularly effective in treating this disorder. Although complete block of Ca$_v$2.2 can cause hypotension or impair baroreceptor reflexes, partial inhibition by Ca$_v$2.2 modulators might reduce hypertension with minimal reflex tachycardia (Uneyama, O. D. Int. J. Mol. Med. 1999 3:455-466).

Pain causes a great deal of suffering and is a sensory experience distinct from sensations of touch, pressure, heat and cold. It is often described by sufferers by such terms as bright, dull, aching, pricking, cutting or burning and is generally considered to include both the original sensation and the reaction to that sensation. This range of sensations, as well as the variation in perception of pain by different individuals, renders a precise definition of pain difficult. Where pain is "caused" by the stimulation of nociceptive receptors and transmitted over intact neural pathways, this is termed nociceptive pain. Pain may also be caused by damage to neural structures, and pain is often is manifested as neural supersensitivity; this type of pain is referred to as neuropathic pain.

DEFINITIONS

"Agonist," as used herein refers to a compound or composition capable of combining with (e.g., binding to, interacting with) receptors to initiate pharmacological actions.

Pharmaceutically acceptable refers to, for example, compounds, materials, compositions, and/or dosage forms which are suitable for use in contact with the tissues of human beings and animals without excessive toxicity, irritation, allergic response, or other problems or complications, commensurate with a reasonable benefit/risk ratio.

Pharmaceutically acceptable salts refer to, for example, derivatives of the disclosed compounds wherein the compounds are modified by making at least one acid or base salt thereof, and includes inorganic and organic salts.

An analgesic amount refers, for example, to the administration of an amount of opioid agonist or a Cav2 modulator which causes analgesia in a subject administered the opioid agonist or a Cav2 modulator, and includes standard doses of an opioid agonist which are typically administered to cause analgesia (e.g., mg doses).

A subanalgesic amount of opioid agonist or a Cav2 modulator refers to an amount which does not cause analgesia in a subject administered the opioid agonist or a Cav2 modulator alone, but when used in combination with a potentiating or enhancing amount of a opioid agonist or a Cav2 modulator, results in analgesia.

An effective antagonistic amount of Cav2 modulator refers to an amount that effectively attenuates (e.g. blocks, inhibits, prevents, or competes with) the activity of the channel.

A therapeutically effective amount of a pain-alleviating composition refers to an amount that elicits alleviation or lessening of at least one symptom of pain upon administration to a subject in need thereof.

Potency refer, for example, to the strength of a composition or treatment in producing desired effects, for example, analgesia and/or the alleviation of, for example, hyperalgesia, allodynia, hyperesthesia or phantom pain. Potency also may refer to the effectiveness or efficacy of a composition in eliciting desired effects, for example, analgesia and/or alleviation of hyperalgesia, allodynia, hyperesthesia, spontaneous burning pain or phantom pain. Enhanced potency, for example, refers to the lowering of a dose in achieving desired effects or to an increased therapeutic benefit including that not previously seen, for example, where the increased therapeutic benefit is eliciting desired effects such as analgesia and/or alleviation of hyperalgesia (e.g., hyperalgesia not associated with or resulting from administration of an opioid agonist, such as chronic administration of the opioid agonist), allodynia, hyperesthesia, spontaneous burning pain or phantom pain from oral administration, oral formulation or oral dosage form. In therapeutics, for example, potency may refer to the relative pharmacological activity of a compound or a composition.

Enhance potency of an opioid agonist, as used herein, refers to the ability of the Cav2 modulation agents of the invention to increase the potency of an opionid agent. For example, less of an opioid agent or fewer doses may be administered to achieve the same pain relieving affect on the subject.

An anticonvulsant or anti-epileptic refers to a pharmaceutically acceptable agent or therapeutic agent that treats or prevents or arrests seizures, such as in epilepsy. Anticonvulsants include, for example, cabamazepine, phenyloin, valproate, ethosuximide, gabapentin, lamotrigine, levetiracetam, tiagabine, toprimate, and zonisamide.

A local anesthetic and/or analgesic refers to a pharmaceutically acceptably agent or therapeutic agent that is administered locally to a nerve and anesthetizes local nerves, thereby conferring pain relief. Local anesthetics include, for example, bupivicaine hydrochloride, chloroprocaine hydrochloride, dibucaine, dibucaine hydrochloride, etidocaine hydrochloride, lidocaine, lidocaine hydrochloride, mepivacaine hydrochloride, piperocaine hydrochloride, prilocalne hydrochloride, procaine hydrochloride propoxycaine hydrochloride tetracaine or tetracaine hydrochloride and their 1,2 and 1,3 hydroxy derivatives; meperidine, diphenoxylate, loperimide, fentanyl, sufentanil, alfentanil, remifentanil, and the like.

The term "receptor" refers to a molecule or complex of molecules, typically (although not necessarily) a protein(s), that is specifically bound by one or more particular ligands. The receptor is said to be a receptor for such ligand(s). Ligand-receptor binding, in many instances, induces one or more biological responses.

A "G protein-coupled receptor" is a receptor that activates an associated "G protein" upon ligand-receptor binding.

The term "G protein" refers to a class of heterotrimeric proteins that binds GDP. Ligand-receptor binding stimulates a receptor-G protein interaction that results in the exchange GDP bound to the G protein for GTP. G proteins are made up of alpha, beta, and gamma subunits. One or more G protein subunits then typically interact with one or more effectors or effector systems that mediate a biological response.

The term "channel" refers to a structure that forms a pore in a cell membrane through which ions pass under particular conditions. A "calcium channel" is a channel through which $Ca^{2+}$ ions pass. A "$Ca_v2$ channel" is a voltage-gated calcium channel, wherein membrane depolarization leads to an inward calcium current. $Ca_v2$ channels include the N-type $Ca_v2.2$ subunit, and are inhibited by G protein beta-gamma subunits.

As used herein, a "$Ca_v2$ voltage gated calcium channel modulator" is a compound, therapeutic, composition, peptide, protein, or nucleic acid that modulates $Ca_v2$ voltage gated calcium channel. The modulation may be inhibition or activation. The inhibition and activation may be partial or complete.

As used herein, "predominate modulation determinant of a $Ca_v2$ channel" refers to a portion, section, location sequence or domain of a $Ca_v2$ channel that underlies the G-protein modulation of the channel.

A $Ca_v2$ related disorder as used herein refers to disorders that are N—($Ca_v2.2$), P/Q-($Ca_v2.1$), or R-type ($Ca_v2.3$) calcium channel related disorders. The disorders include, for example, pain (chronic, neuropathic, acute), trauma, migraine, neurological disorders (anxiety, stroke, psychoses, schizophrenia, depression, epilepsy), cardiovascular conditions (hypertension and cardiac arrhythmias), cancer, drug addiction, analgesic side effect, analgesic tolerance, diabetes, infertility, or a behavioral disorder.

The following terms encompass polypeptides that are identified in Genbank by the following designations, as well as polypeptides that are at least about 70% identical to polypeptides identified in Genbank by these designations: subunits of Cav2 channels, particularly N-type $Ca_v2.2$. In alternative embodiments, these terms encompass polypeptides identified in Genbank by these designations and polypeptides sharing at least about 80, 90, 95, 96, 97, 98, or 99% identity.

A "$Ca_v2$ modulator" is either an inhibitor or an enhancer of a $Ca_v2$ channel. A "non-selective" $Ca_v2$ modulator is an agent that modulates other calcium channels at the concentrations typically employed for $Ca_v2$ channel modulation. A "selective" $Ca_v2$ modulator significantly modulates one or more of the normal functions of an Cav2 channel at a concentration at which other calcium channels are not significantly modulated. A modulator "acts directly on" a $Ca_v2$ channel when the modulator binds to the $Ca_v2$ channel. A modulator "acts indirectly on a $Ca_v2$ channel" when the modulator binds to a molecule other than the $Ca_v2$ channel, which binding results in modulation of the $Ca_v2$ channel.

A "modulator of a $Ca_v2$ channel" is an agent that reduces, by any mechanism, the extent of depolarization-induced inward calcium current through $Ca_v2$ channels, as compared to that observed in the absence (or presence of a smaller amount) of the agent. A modulator of an $Ca_v2$ calcium channel can affect: (1) the expression; mRNA stability; or protein trafficking, modification (e.g., phosphorylation), or degradation of an $Ca_v2$ channel or one or more of its subunits (e.g., $Ca_v2.2$), or (2) one or more of the normal functions of a $Ca_v2$ calcium channel, such the depolarization-induced inward calcium current. An modulator of an $Ca_v2$ calcium channel can be non-selective or selective.

An "enhancer of a $Ca_v2.2$ calcium channel" is an agent that increases, by any mechanism, the extent of depolarization-induced inward calcium current through $Ca_v2$ calcium channels, as compared to that observed in the absence (or presence of a smaller amount) of the agent. An enhancer of an $Ca_v2$ calcium channel can affect: (1) the expression; mRNA stability; or protein trafficking, modification (e.g., phosphorylation), or degradation of an $Ca_v2$ calcium channel or one or more of its subunits (e.g., $Ca_v2.2$), or (2) one or more of the normal functions of an $Ca_v2$ calcium channel, such the depolarization-induced inward calcium current. An enhancer of an $Ca_v2$ calcium channel can be non-selective or selective.

The terms "polypeptide" and "protein" are used interchangeably herein to refer a polymer of amino acids, and unless otherwise limited, include atypical amino acids that can function in a similar manner to naturally occurring amino acids.

The terms "amino acid" or "amino acid residue," include naturally occurring L-amino acids or residues, unless otherwise specifically indicated. The commonly used one- and three-letter abbreviations for amino acids are used herein (Lehninger, A. L. (1975) Biochemistry, 2d ed., pp. 71-92, Worth Publishers, N.Y.). The terms "amino acid" and "amino acid residue" include D-amino acids as well as chemically modified amino acids, such as amino acid analogs, naturally occurring amino acids that are not usually incorporated into proteins, and chemically synthesized compounds having the characteristic properties of amino acids (collectively, "atypical" amino acids). For example, analogs or mimetics of phenylalanine or proline, which allow the same conformational restriction of the peptide compounds as natural Phe or Pro are included within the definition of "amino acid."

"Opioid analgesics" as used herein refer to a class of analgesic agents. These compounds are generally include, in a generic sense, all drugs, natural or synthetic, with morphine-like actions. The synthetic and semi-synthetic opioid analgesics are derivatives of five chemical classes of compound: phenanthrenes; phenylheptylamines; phenylpiperidines; morphinans; and benzomorphans. Pharmacologically these compounds have diverse activities, thus some are strong agonists at the opioid receptors (e.g. morphine); others are moderate to mild agonists (e.g. codeine); still others exhibit mixed agonist-antagonist activity (e.g. nalbuphine); and yet others are partial agonists (e.g. nalorphine). Whilst an opioid partial agonist such as nalorphine, (the N-alkyl analogue of morphine) will antagonize the analgesic effects of morphine, when given alone it can be a potent analgesic in its own right. Of all of the opioid analgesics, morphine remains the most widely used and is a suitable archetype compound. Unfortunately, apart from its useful therapeutic properties, morphine also has a number of drawbacks including respiratory depression, decreased gastrointestinal motility (resulting in constipation) and, in some individuals, nausea and vomiting may occur. Another characteristic is the development of tolerance and physical dependence which may limit the clinical use of such compounds.

Anti-inflammatory compounds directed at blocking or reducing synovial inflammation, and thereby improving function, and analgesics directed to reducing pain, are presently the primary method of treating the rheumatoid diseases and arthritis. Aspirin and other salicylate compounds are frequently used in treatment to interrupt amplification of the inflammatory process and temporarily relieve the pain. Other drug compounds used for these purposes include phenylpropionic acid derivatives such as Ibuprofen and Naproxin, Sulindac, phenyl butazone, corticosteroids, antimalarials such as chloroquine and hydroxychloroquine sulfate, and fenemates. For a thorough review of various drugs utilized in treating rheumatic diseases, reference is made to J. Hosp. Pharm., 36:622 (May 1979).

Neurological disorders include, for example, disorders involving the brain, cortex, dorsal root ganglion (DRG) neurons, sciatic nerve, and spinal cord.

Disorders involving the brain include, for example, disorders involving neurons, and disorders involving glia, and developmental diseases, such as neural tube defects, forebrain anomalies, posterior fossa anomalies, and syringomyelia and hydromyelia; perinatal brain injury; cerebrovascular diseases; infections, such as acute meningitis, acute focal suppurative infections, including brain abscess, subdural empyema, and extradural abscess, chronic bacterial meningoencephalitis, including tuberculosis and mycobacterioses, neurosyphilis, and neuroborreliosis, viral meningoencephalitis, progressive multifocal leukoencephalopathy, subacute sclerosing panencephalitis, fungal meningoencephalitis; transmissible spongiform encephalopathies; demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, spinocerebellar degenerations; inborn errors of metabolism; and toxic and acquired metabolic diseases. Disorders of the peripheral nervous system include, inflammatory neuropathies, such as, immune-mediated neuropathies; infectious polyneuropathies, such as, leprosy, diphtheria, varicella-zoster virus; hereditary neuropathies, such as, hereditary motor and sensory neuropathy I, HMSN II, Dejerine-Sottas Disease; acquired metabolic and toxic neuropathies, such as, peripheral neuropathy in adult-onset diabetes mellitus, metabolic and nutritional peripheral neuropathies, neuropathies associated with malignancy, toxic neuropathies; traumatic neuropathies; and tumors of the peripheral nerve.

The phrase "a drug-related effect or behavior" refers to an in vivo effect or behavior that occurs in response to a drug. Exemplary effects include stimulant, sedative, hypnotic, and ataxic effects, as well as drug reward. An example of a drug-related behavior is drug consumption. The term "drug reward" refers to the tendency of a drug to induce a subject to alter their behavior to obtain more of the drug.

A "sedative effect" refers to a decrease in activity and/or excitement in a subject. A "hypnotic effect" includes an increase in drowsiness and/or a facilitation of the onset and/or maintenance of sleep. An "ataxic effect" refers to a decrease in motor coordination.

A "test agent" is any agent that can be screened in the prescreening or screening assays of the invention. The test agent can be any suitable composition, including a small molecule, peptide, or polypeptide.

An agent is said to "modulate" a drug-related effect or behavior if the agent inhibits or enhances the drug-related effect or behavior.

The term "therapy," as used herein, encompasses the treatment of an existing condition as well as preventative treatment (i.e., prophylaxis). Accordingly, "therapeutic" effects and applications include prophylactic effects and applications, respectively. A used herein, the term "high risk" refers to an elevated risk as compared to that of an appropriate matched (e.g., for age, sex, etc.) control population.

"Nucleic acids," as used herein, refers to nucleic acids that are isolated a natural source; prepared in vitro, using techniques such as PCR amplification or chemical synthesis; prepared in vivo, e.g., via recombinant DNA technology; or by any appropriate method. Nucleic acids may be of any shape (linear, circular, etc.) or topology (single-stranded, double-stranded, supercoiled, etc.). The term "nucleic acids" also includes without limitation nucleic acid derivatives such as peptide nucleic acids (PNA's) and polypeptide-nucleic acid conjugates; nucleic acids having at least one chemically modified sugar residue, backbone, internucleotide linkage, base, nucleoside, or nucleotide analog; as well as nucleic acids having chemically modified 5' or 3' ends; and nucleic acids having two or more of such modifications. Not all linkages in a nucleic acid need to be identical.

In general, the oligonucleotides may be single-stranded (ss) or double-stranded (ds) DNA or RNA, or conjugates (e.g., RNA molecules having 5' and 3' DNA "clamps") or hybrids (e.g., RNA:DNA paired molecules), or derivatives (chemically modified forms thereof). However, single-stranded DNA is preferred, as DNA is often less labile than RNA. Similarly, chemical modifications that enhance an aptamer's specificity or stability are preferred.

Chemical modifications that may be incorporated into nucleic acids include, with neither limitation nor exclusivity, base modifications, sugar modifications, and backbone modifications. Base modifications: The base residues in aptamers may be other than naturally occurring bases (e.g., A, G, C, T, U, 5MC, and the like). Derivatives of purines and pyrimidines are known in the art; an exemplary but not exhaustive list includes aziridinylcytosine, 4-acetylcytosine, 5-fluorouracil, 5-bromouracil, 5-carboxymethylaminomethyl-2-thiouracil, 5-carboxymethylaminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine (5MC), N6-methyladenine, 7-methylguanine, 5-methylaminomethyluracil, 5-methoxyaminomethyl-2-thiouracil, beta-D-mannosylqueosine, 5-methoxyuracil, 2-methylthio-N-6-isopentenylade-nine, uracil-5-oxyacetic acid methylester, pseudouracil, queosine, 2-thiocytosine, 5-methyl-2-thiouracil, 2-thiouracil, 4-thiouracil, 5-methyluracil, uracil-5-oxyacetic acid, and 2,6-diaminopurine. In addition to nucleic acids that incorporate one or more of such base derivatives, nucleic acids having nucleotide residues that are devoid of a purine or a pyrimidine base may also be included in aptamers. Sugar modifications: The sugar residues in aptamers may be other than conventional ribose and deoxyribose residues. By way of non-limiting example, substitution at the 2'-position of the furanose residue enhances nuclease stability. An exemplary, but not exhaustive list, of modified sugar residues includes 2' substituted sugars such as 2'-O-methyl-, 2'-O-alkyl, 2'-O-allyl, 2'-S-alkyl, 2'-S-allyl, 2'-fluoro-, 2'-halo, or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and abasic nucleoside analogs such as methyl riboside, ethyl riboside or propylriboside.

Exemplary atypical amino acids, include, for example, those described in International Publication No. WO 90/01940 as well as 2-amino adipic acid (Aad) which can be substituted for Glu and Asp; 2-aminopimelic acid (Apm), for Glu and Asp; 2-aminobutyric acid (Abu), for Met, Leu, and other aliphatic amino acids; 2-aminoheptanoic acid (Ahe), for Met, Leu, and other aliphatic amino acids; 2-aminoisobutyric acid (Aib), for Gly; cyclohexylalanine (Cha), for Val, Leu, and Ile; homoarginine (Har), for Arg and Lys; 2,3-diaminopropionic acid (Dpr), for Lys, Arg, and H is; N-ethylglycine (EtGly) for Gly, Pro, and Ala; N-ethylasparagine (EtAsn), for Asn and Gln; hydroxyllysine (Hyl), for Lys; allohydroxyllysine (Ahyl), for Lys; 3-(and 4-) hydroxyproline (3Hyp, 4Hyp), for Pro, Ser, and Thr; allo-isoleucine (Aile), for Ile, Leu, and Val; amidinophenylalanine, for Ala; N-methylglycine (MeGly, sarcosine), for Gly, Pro, and Ala; N-methylisoleucine (MeIle), for Ile; norvaline (Nva), for Met and other aliphatic amino acids; norleucine (Nle), for Met and other aliphatic amino acids; ornithine (Om), for Lys, Arg, and His; citrulline (Cit) and methionine sulfoxide (MSO) for Thr, Asn, and Gln; N-methylphenylalanine (MePhe), trimethylphenylalanine, halo (F, Cl, Br, and I) phenylalanine, and trifluorylphenylalanine, for Phe.

The terms "identical" or "percent identity," in the context of two or more amino acid or nucleotide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman (1988) Proc. Natl. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle (1987) J. Mol. Evol. 35:351-360. The method used is similar to the method described by Higgins & Sharp (1989) CABIOS 5: 151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al. (1990) J. Mol. Biol. 215: 403-410. Software for performing BLAST analyses is publicly available through the National Center for Biotechnology Information (http://www.ncbi.nlm.nih.go-v/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul (1993) Proc. Natl. Acad. Sci. USA, 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The term "specific binding" is defined herein as the preferential binding of binding partners to another (e.g., two polypeptides, a polypeptide and nucleic acid molecule, or two nucleic acid molecules) at specific sites. The term "specifically binds" indicates that the binding preference (e.g., affinity) for the target molecule/sequence is at least 2-fold, more preferably at least 5-fold, and most preferably at least 10- or 20-fold over a non-specific target molecule (e.g. a randomly generated molecule lacking the specifically recognized site(s)).

A "radioligand binding assay" is an assay in which a biological sample (e.g., cell, cell lysate, tissue, etc.) containing a receptor is contacted with a radioactively labeled ligand for the receptor under conditions suitable for specific binding between the receptor and ligand, unbound ligand is removed, and receptor binding is determined by detecting bound radioactivity.

As used herein, an "antibody" refers to a protein consisting of one or more polypeptides substantially encoded by immunoglobulin genes or fragments of immunoglobulin genes. Immunoglobulin genes include, for example, the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The term antibody, as used herein also includes antibody fragments either produced by the modification of whole antibodies or synthesized de novo using recombinant DNA methodologies, see for example, Fundamental Immunology, W. E. Paul, ed., Raven Press, N.Y. (1993), for a more detailed description of other antibody fragments. While various antibody fragments are defined in terms of the digestion of an intact antibody, one of skill will appreciate that such Fab' fragments may be synthesized de novo either chemically or by utilizing recombinant DNA methodology. Antibodies also include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker. Huston, et al. (1988) Proc. Nat. Acad. Sci. USA, 85: 5879-5883. While the VH and VL are connected to each as a single polypeptide chain, the VH and VL domains associate non-covalently. The scFv antibodies and a number of other structures converting the naturally aggregated, but chemically separated, F light and heavy polypeptide chains from an antibody V region into a molecule that folds into a three-dimensional structure substantially similar to the structure of an antigen-binding site are known to those of skill in the art (see e.g., U.S. Pat. Nos. 5,091,513, 5,132,405, and 4,956,778).

The phrases "an effective amount" and "an amount sufficient to" refer to amounts of a biologically active agent that produce an intended biological activity.

The term "polynucleotide" refers to a deoxyribonucleotide or ribonucleotide polymer, and unless otherwise limited, includes known analogs of natural nucleotides that can function in a similar manner to naturally occurring nucleotides. The term "polynucleotide" refers any form of DNA or RNA, including, for example, genomic DNA; complementary DNA (cDNA), which is a DNA representation of mRNA, usually obtained by reverse transcription of messenger RNA (mRNA) or amplification; DNA molecules produced synthetically or by amplification; and mRNA. The term "polynucleotide" encompasses double-stranded nucleic acid molecules, as well as single-stranded molecules. In double-stranded polynucleotides, the polynucleotide strands need not be coextensive (i.e., a double-stranded polynucleotide need not be double-stranded along the entire length of both strands).

As used herein, the term "complementary" refers to the capacity for precise pairing between two nucleotides. I.e., if a nucleotide at a given position of a nucleic acid molecule is capable of hydrogen bonding with a nucleotide of another nucleic acid molecule, then the two nucleic acid molecules are considered to be complementary to one another at that position. The term "substantially complementary" describes sequences that are sufficiently complementary to one another to allow for specific hybridization under stringent hybridization conditions.

The phrase "stringent hybridization conditions" generally refers to a temperature about 5° C. lower than the melting temperature ($T_m$) for a specific sequence at a defined ionic strength and pH. Exemplary stringent conditions suitable for achieving specific hybridization of most sequences are a temperature of at least about 60° C. and a salt concentration of about 0.2 molar at pH 7.

"Specific hybridization" refers to the binding of a nucleic acid molecule to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

Methods of Treating

The present invention provides for both prophylactic and therapeutic methods of treating a subject at risk of, or susceptible to, a $Ca_v2$ disease or disorder. Treatment is defined as the application or administration of a therapeutic agent to a patient, or application or administration of a therapeutic agent to an isolated tissue or cell line from a patient, who has a $Ca_v2$ disease or disorder, a symptom of a $Ca_v2$ disease or disorder or a predisposition toward a $Ca_v2$ disease or disorder, with the purpose to cure, heal, alleviate, relieve, alter, remedy, ameliorate, improve or affect the $Ca_v2$ disease or disorder, the symptoms of the $Ca_v2$ disease or disorder or the predisposition toward the $Ca_v2$ disease or disorder.

The therapeutic methods of the invention involve the administration of the polypeptide and/or nucleic acid molecules of the invention as described herein.

In one aspect, the invention provides a method for preventing $Ca_v2$ disease or disorder in a subject by administering to the subject a polypeptide or nucleic acid molecule of the invention as described herein.

The invention provides therapeutic methods and compositions for the prevention and treatment of Cav2 disease or disorder. In particular, the invention provides methods and compositions for the prevention and treatment of Cav2 disease or disorder in subjects.

In one embodiment, the present invention contemplates a method of treatment, comprising: a) providing, i.e., administering: i) a mammalian patient particularly human who has, or is at risk of developing a Cav2 disease or disorder, ii) one or more molecules of the invention as described herein.

The term "at risk for developing" is herein defined as individuals an increased probability of contracting an $Ca_v2$ disease or disorder due to exposure or other health factors.

The present invention is also not limited by the degree of benefit achieved by the administration of the molecule. For example, the present invention is not limited to circumstances where all symptoms are eliminated. In one embodiment, administering a molecule reduces the number or severity of symptoms of a Cav2 disease or disorder. In another embodiment, administering of a molecule may delay the onset of symptoms of a Cav2 disease or disorder.

Yet another aspect of this invention relates to a method of treating a subject (e.g., mammal, human, horse, dog, cat, mouse) having a disease or disease symptom (including, but not limited to angina, hypertension, congestive heart failure, myocardial ischemia, arrhythmia, diabetes, urinary incontinence, stroke, pain, traumatic brain injury, or a neuronal disorder). The method includes administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

Yet another aspect of this invention relates to a method of treating a subject (e.g., mammal, human, horse, dog, cat, mouse) having an Cav2 related disease or symptom (including, but not limited to pain, angina, hypertension, congestive heart failure, myocardial ischemia, arrhythmia, diabetes, urinary incontinence, stroke, traumatic brain injury, or a neuronal or neurological disorder). The method includes administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g., opinion) or objective (e.g., measurable by a test or diagnostic method).

Typical subjects for treatment in accordance with the individuals include mammals, such as primates, preferably humans. Cells treated in accordance with the invention also preferably are mammalian, particularly primate, especially human. As discussed above, a subject or cells are suitably identified as in needed of treatment, and the identified cells or subject are then selected for treatment and administered one or more of fusion molecules of the invention.

The treatment methods and compositions of the invention also will be useful for treatment of mammals other than humans, including for veterinary applications such as to treat horses and livestock e.g., cattle, sheep, cows, goats, swine and the like, and pets such as dogs and cats.

The invention provides a method of reducing or preventing a drug-related effect or behavior. The method entails inhibiting an $Ca_v2$ channel in a subject, whereby the drug-related effect or behavior is reduced or prevented. Generally, the method is carried out by administering an $Ca_v2$ channel modulator to a subject. The method is useful for addressing undesirable effects or behaviors associated with a variety of drugs, particularly sedative-hypnotic and analgesic drugs. In particular embodiments, the method is used to reduce or prevent effects or behaviors associated with drugs such as ethanol, cannabinioids, opioids, and the like. Exemplary cannabinioids include Tetrahydrocannabinol (THC), dronabinol, arachidonylethanolamide (anandamide, AEA). Exemplary opioids include morphine, codeine, heroin, butorphanol, hydrocodone, hydromorphone, levorphanol, meperidine, nalbuphine, oxycodone, fentanyl, methadone, propoxyphene, remifentanil, sufentanil, and pentazocine.

Examples of undesirable drug-related effects or behaviors that can be reduced or prevented according to the method of the invention include sedative and hypnotic effects; drug reward; and drug consumption.

The subject of the method can be any individual that has one or more $Ca_v2$ channels. Examples of suitable subjects include research animals, such as *Drosophila melanogaster*, mice, rats, guinea pigs, rabbits, cats, dogs, as well as monkeys and other primates, and humans. The subject can be an individual who is regularly, or intermittently, using one or more of the above drugs or an individual who is at risk for such use.

This method also entails inhibiting one or more $Ca_v2$ channels to a degree sufficient to reduce or prevent the drug-related effect(s) and/or behavior(s) of interest. In various embodiments, the $Ca_v2$ channel is inhibited by at least about 10, 20, 30, 40, 50, 60, 70, 80, 90, and 95 percent, as determined by any suitable measure of channel inhibition (such as, for example, any of the assays described herein).

Suitable types of Cav2 channel modulators include those encoded by SEQ ID NOs: 1-3 or fragments or variants thereof.

In other embodiments, the inhibition $Ca_v2$ channels can be achieved by any available means, e.g., inhibition of: (1) the expression, mRNA stability, protein trafficking, modification (e.g., phosphorylation), or degradation of an $Ca_v2$ channel or one or more of its subunits (e.g., N-type $Ca_v2.2$), or (2) one or more of the normal functions of an $Ca_v2$ channel, such the depolarization-induced inward calcium current.

In one embodiment, $Ca_v2$ channel inhibition is achieved by reducing the level of $Ca_v2$ channels in a tissue having such channels. $Ca_v2$ channels are expressed in neurons of the central and peripheral nervous systems. Thus, the method of the invention can target $Ca_v2$ channels in brain, dorsal root ganglion neurons, and sympathetic ganglion neurons. In a variation of this embodiment, N-type channel level is reduced by reducing the level of N-type $Ca_v2.2$ subunits in the tissue. This can be achieved using, e.g., antisense or RNA interference (RNAi) techniques to reduce the level of N-type $Ca_v2.2$ RNA available for translation.

In one embodiment, the $Ca_v2$ channel modulator can administered with a be non-selective or selective for modulator of the $Ca_v2$ channel. Examples of non-selective modulators suitable for use in the invention include omega conotoxin MVIIC, omega grammotoxin SIA, and omega agatoxin IIIA. Preferred embodiments employ a selective modulator, such as, for example, omega-conotoxin MVIIA, omega conotoxin GVIA, omega conotoxin CNVIIA (Favreau et al., 2001), omega conotoxin CVID (AM336; Lewis et al., 2000), Ptul (a toxin from the assassin bug *Peirates turpis*; Bernard et al. 2001), NMED-126, and NMED-160 (both of the latter two compounds are produced by NeuroMed Technologies, Inc., Vancouver, British Columbia, Calif.). Additional Cav2 channel modulators useful in the invention are described in U.S. Pat. Nos. 6,617,322, 6,492,375; 6,387,897; 6,310,059; 6,267,945; 6,011,035 and in published U.S. application Ser. No. 10/409,868 (published Mar. 4, 2004; Publication No. 20040044004) and Ser. No. 10/409,763 (published Feb. 19, 2004; Publication No. 20040034035).

Methods of Screening

The role of $Ca_v2$ channels in mediating $Ca_v2$ related disorders, e.g., pain (chronic, neuropathic, acute), trauma, migraine, neurological disorders (anxiety, stroke, psychoses, schizophrenia, depression, epilepsy), cardiovascular conditions (hypertension and cardiac arrhythmias), cancer, drug addiction, analgesic side effect, analgesic tolerance, diabetes, infertility, a behavioral disorder, drug-related effects and behaviors makes the Cav2 channel an attractive target for agents that modulate these disorders to effectively treat, prevent, ameliorate, reduce or alleviate the disorders. Accordingly, the invention provides prescreening and screening methods aimed at identifying such agents. The prescreening/screening methods of the invention are generally, although not necessarily, carried out in vitro. Accordingly, screening assays are generally carried out, for example, using purified or partially purified components in cell lysates or fractions thereof, in cultured cells, or in a biological sample, such as a tissue or a fraction thereof or in animals.

The invention provides a prescreening method based on assaying test agents for specific binding to an $Ca_v2$ channel at the predominant modulation determinant region. Agents that specifically bind to the predominant modulation determinant region have the potential to modulate channel function, and thereby modulate one or more $Ca_v2$ disorders.

In one embodiment, therefore, a prescreening method comprises contacting a test agent with an $Ca_v2$ channel or a subunit thereof, such as the N-type $Ca_v2.2$ subunit. Specific binding of the test agent to the N-type channel or subunit at the predominant modulation determinant region is then determined. If specific binding is detected, the test agent is selected as a potential modulator of a drug-related effect or behavior.

Such prescreening is generally most conveniently accomplished with a simple in vitro binding assay. Means of assaying for specific binding of a test agent to a polypeptide are well known to those of skill in the art and are detailed in the Examples infra. In one binding assay, the polypeptide is immobilized and exposed to a test agent (which can be labeled), or alternatively, the test agent(s) are immobilized and exposed to the polypeptide (which can be labeled). The immobilized species is then washed to remove any unbound material and the bound material is detected. To prescreen large numbers of test agents, high throughput assays are generally preferred. Various screening formats are discussed in greater detail below.

Test agents, including, for example, those identified in a prescreening assay of the invention can also be screened to determine whether the test agent affects the levels of $Ca_v2$ channels or channel subunit polypeptides or RNA. Agents that reduce these levels can potentially reduce one or more $Ca_v2$ related disorders.

Accordingly, the invention provides a method of screening for an agent that modulates a $Ca_v2$ related disorder in which a test agent is contacted with a cell that expresses a $Ca_v2$ channel in the absence of test agent. Preferably, the method is carried out using an in vitro assay or in vivo. In such assays, the test agent can be contacted with a cell in culture or to a tissue. Alternatively, the test agent can be contacted with a cell lysate or fraction thereof (e.g., a membrane fraction for detection of $Ca_v2$ channels or channel subunit polypeptides). The level of (i) $Ca_v2$ channels; (ii) channel subunit polypeptide; or (iii) channel subunit RNA is determined in the presence and absence (or presence of a lower amount) of test agent to identify any test agents that alter the level. Where channel subunit polypeptide or RNA is determined, the channel subunit is preferably N-type $Ca_v2.2$. If the level assayed is altered, the test agent is selected as a potential modulator $Ca_v2$ related disorder. In a preferred embodiment, an agent that reduces the level assayed is selected as a potential modulator of one or more $Ca_v2$ related disorders.

Cells useful in this screening method include those from any of the species described above in connection with the method of reducing a drug-related effect or behavior. Cells that naturally express an $Ca_v2$ channel are useful in this screening methods. Examples include PC12 cells, SH-SY5y cells, NG108-15 cells, IMR-32 cells, SK-N-SH cells, RINm5F cells, and NMB cells. Alternatively, cells that have been engineered to express a $Ca_v2$ channel can be used in the method.

In one embodiment, the test agent is contacted with the cell in the presence of a drug. The drug is generally one that produces one or more undesirable effects or behaviors, such as, for example, sedative-hypnotic and analgesic drugs. In particular embodiments, the drug is ethanol, a cannabinioid, or an opioid.

As noted above, screening assays are generally carried out in vitro, for example, in cultured cells, in a biological sample (e.g., brain, dorsal root ganglion neurons, and sympathetic ganglion neurons), or fractions thereof. For ease of description, cell cultures, biological samples, and fractions are referred to as "samples" below. The sample is generally derived from an animal (e.g., any of the research animals mentioned above), preferably a mammal, and more preferably from a human.

The sample may be pretreated as necessary by dilution in an appropriate buffer solution or concentrated, if desired. Any of a number of standard aqueous buffer solutions, employing one or more of a variety of buffers, such as phosphate, Tris, or the like, at physiological pH can be used.

$Ca_v2$ channels and/or channel subunit polypeptides can be detected and quantified by any of a number of methods well known to those of skill in the art. Examples of analytic biochemical methods suitable for detecting $Ca_v2$ channel subunit or, in some cases, entire channels, include electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunohistochemistry, affinity chromatography, immunoelectrophoresis, radioimmunoassay (RIA), receptor-linked immunosorbent assays (ELISAs), immunofluorescent assays, Western blotting, fluorescence resonance energy transfer (FRET) assays, yeast two-hybrid assays, whole or partial cell current recordings, and the like. Peptide modulators may be discovered or screened for example, by phage display. See 5,096,815; 5,198,346; 5,223,409; 5,260,203; 5,403,484; 5,534,621; and 5,571,698.

Methods for identifying lead compounds for a pharmacological agent useful in the treatment of a $Ca_v2$ related disorder comprising contacting a predominant modulation determinant of a calcium channel with a test compound, and measuring channel modulation. The predominant modulation determinant may be isolated or may be part of a partial or complete calcium channel. The calcium channel may also be a modified calcium channel, e.g., a chimeric channel and/or a deletion mutant. The calcium channel may be isolated or may be in a membrane or an artificial membrane. The contacting may be directly or indirectly. The channel modulation may be measured by one or more of compound-state analysis, $K_{d\ EFF}$, G/Q analysis, DF facilitation, and current recording. These methods are known in the art and are further described below in the Examples.

Methods of the invention also comprise identifying the predominant modulation determinant of a calcium channel. For example, by a FRET two-hybrid, yeast two-hybrid, phage display, and channel structure-function screen. Methods are described infra, especially in the Examples below.

The methods of the invention, for example, the screening methods may further comprise activating the calcium channel prior to or after contacting it with a test compound. Activation may be with a Gβγ protein, or a fragment or variant thereof or with a compound.

In the methods, the calcium channel may be one or more of N-terminus truncated N-type $Ca_v2.2$ calcium channel, N-terminus replaced with aIB with $\alpha_{1C}$, $\alpha_{1B}$ channel with a C-tail truncation at 1877, $\alpha_{1B}$ channel with a C-tail truncation at 1877 fused to YFP, deletion of $NT_B$ residues of the $\alpha_{1B}$ subunit ($\alpha_{1b(\Delta56-90)BbBBBb}$), an N-type $Ca_v2.2$ calcium channel with a replacement of the I-II loop of $\alpha_{1B}$ with that of $\alpha_{1C}$.

Methods of the invention also include methods for screening a therapeutic agent to treat, prevent, ameliorate, reduce or alleviate a $Ca_v2$ related disorder or symptoms thereof, comprising administering a test agent to a mouse having an overexpressed $NT_B$ peptide, and measuring modulation of pain thresholds or calcium influx. Transgenic animals over-expressed $NT_B$ peptides are easily made by those of skill in the art. Examples of $NT_B$ peptides include, for example, $NT_B$ (56-95) MALYNPIPVKQNCFTVNRSLFVFSEDNVVRKYAKRITEWP.

In certain methods of the invention, for example screening methods, a decrease in the influx of calcium indicates that the test agent may be useful in treating a $Ca_v2$ disorder.

High Throughput Screening Assays

High throughput screening (HTS) typically uses automated assays to search through large numbers of compounds for a desired activity. Typically HTS assays are used to find new drugs by screening for chemicals that act on a particular receptor or molecule. For example, if a chemical inactivates an receptor it might prove to be effective in preventing a process in a cell which causes a disease. High throughput methods enable researchers to try out thousands of different chemicals against each target very quickly using robotic handling systems and automated analysis of results.

As used herein, "high throughput screening" or "HTS" refers to the rapid in vitro screening of large numbers of compounds (libraries); generally tens to hundreds of thousands of compounds, using robotic screening assays. Ultra high-throughput Screening (uHTS) generally refers to the high-throughput screening accelerated to greater than 100,000 tests per day. Examples include the yeast two-hybrid system and phage display. For examples of phage display see, U.S. Pat. Nos. 5,096,815; 5,198,346; 5,223,409; 5,260,203; 5,403,484; 5,534,621; and 5,571,698.

To achieve high-throughput screening, it is best to house samples on a multicontainer carrier or platform. A multicontainer carrier facilitates measuring reactions of a plurality of candidate compounds simultaneously. Multi-well microplates may be used as the carrier. Such multi-well microplates, and methods for their use in numerous assays, are both known in the art and commercially available.

Screening assays may include controls for purposes of calibration and confirmation of proper manipulation of the components of the assay. Blank wells that contain all of the reactants but no member of the chemical library are usually included. As another example, a known modulator (or activator) of an receptor for which modulators are sought, can be incubated with one sample of the assay, and the resulting decrease (or increase) in the receptor activity determined according to the methods herein. It will be appreciated that modulators can also be combined with the receptor activators or modulators to find modulators which inhibit the receptor activation or repression that is otherwise caused by the presence of the known the receptor modulator. Similarly, when ligands to a sphingolipid target are sought, known ligands of the target can be present in control/calibration assay wells.

Measuring Binding Reactions During Screening Assays

Techniques for measuring the progression of binding reactions in multicontainer carriers are known in the art and include, but are not limited to, the following.

Spectrophotometric and spectrofluorometric assays are well known in the art. Examples of such assays include the use of colorimetric assays for the detection of peroxides, as disclosed in Example 1(b) and Gordon, A. J. and Ford, R. A., The Chemist's Companion: A Handbook Of Practical Data, Techniques, And References, John Wiley and Sons, N.Y., 1972, Page 437.

Fluorescence spectrometry may be used to monitor the generation of reaction products. Fluorescence methodology is generally more sensitive than the absorption methodology. The use of fluorescent probes is well known to those skilled in the art. For reviews, see Bashford et al., Spectrophotometry and Spectrofluorometry: A Practical Approach, pp. 91-114, IRL Press Ltd. (1987); and Bell, Spectroscopy In Biochemistry, Vol. 1, pp. 155-194, CRC Press (1981).

In spectrofluorometric methods, receptors are exposed to substrates that change their intrinsic fluorescence when processed by the target receptor. Typically, the substrate is non-fluorescent and converted to a fluorophore through one or more reactions. As a non-limiting example, SMase activity can be detected using the Amplex®. Red reagent (Molecular Probes, Eugene, Oreg.). In order to measure sphingomyelinase activity using Amplex Red, the following reactions occur. First, SMase hydrolyzes sphingomyelin to yield ceramide and phosphorylcholine. Second, alkaline phosphatase hydrolyzes phosphorylcholine to yield choline. Third, choline is oxidized by choline oxidase to betaine. Finally, $H_2O_2$, in the presence of horseradish peroxidase, reacts with Amplex Red to produce the fluorescent product, Resorufin, and the signal therefrom is detected using spectrofluorometry.

Fluorescence polarization (FP) is based on a decrease in the speed of molecular rotation of a fluorophore that occurs upon binding to a larger molecule, such as a receptor protein, allowing for polarized fluorescent emission by the bound ligand. FP is empirically determined by measuring the vertical and horizontal components of fluorophore emission following excitation with plane polarized light. Polarized emission is increased when the molecular rotation of a fluorophore is reduced. A fluorophore produces a larger polarized signal when it is bound to a larger molecule (e.g., a receptor), slowing molecular rotation of the fluorophore. The magnitude of the polarized signal relates quantitatively to the extent of fluorescent ligand binding. Accordingly, polarization of the "bound" signal depends on maintenance of high affinity binding.

FP is a homogeneous technology and reactions are very rapid, taking seconds to minutes to reach equilibrium. The reagents are stable, and large batches may be prepared, resulting in high reproducibility. Because of these properties, FP has proven to be highly automatable, often performed with a single incubation with a single, premixed, tracer-receptor reagent. For a review, see Owicki et al., Application of Fluorescence Polarization Assays in High-Throughput Screening, Genetic Engineering News, 17:27, 1997.

FP is particularly desirable since its readout is independent of the emission intensity (Checovich, W. J., et al., Nature 375:254-256, 1995; Dandliker, W. B., et al., Methods in Enzymology 74:3-28, 1981) and is thus insensitive to the presence of colored compounds that quench fluorescence emission. Fluoroecence Polarization (FP) and FRET (see below) are well-suited for identifying compounds that block interactions between sphingolipid receptors and their ligands. See, for example, Parker et al., Development of high throughput screening assays using fluorescence polarization: nuclear receptor-ligand-binding and kinase/phosphatase assays, J. Biomol Screen 5:77-88, 2000.

Fluorophores derived from sphingolipids that may be used in FP assays are commercially available. For example, Molecular Probes (Eugune, Oreg.) currently sells sphingomyelin and one ceramide fluorophores. These are, respectively, N-(4,4-difluoro-5,7-dimethyl-4-bora-3a,4a-diaza-s-inda-cene-3-pentanoyl)sphingosyl phosphocholine (BODIPY® FL C5-sphingomyelin); N-(4,4-difluoro-5,7-dimethyl-4-bora-3a,4a-diaza-s-inda-cene-3-dodecanoyl)sphingosyl phosphocholine (BODIPY® FL C12-sphingomyelin); and N-(4,4-difluoro-5,7-dimethyl-4-bora-3a,4a-diaza-s-indacene-3-pentanoyl)sphingosine (BODIPY® FL C5-ceramide). U.S. Pat. No. 4,150,949, (Immunoassay for gentamicin), discloses fluorescein-labelled gentamicins, including fluoresceinthiocarbanyl gentamicin. Additional fluorophores may be prepared using methods well known to the skilled artisan.

Exemplary normal-and-polarized fluorescence readers include the POLARION fluorescence polarization system (Tecan A G, Hombrechtikon, Switzerland). General multi-well plate readers for other assays are available, such as the VERSAMAX reader and the SPECTRAMAX multiwell plate spectrophotometer (both from Molecular Devices).

Fluorescence resonance energy transfer (FRET) is another useful assay for detecting interaction and has been described previously. See, e.g., Heim et al., Curr. Biol. 6:178-182, 1-996; Mitra et al., Gene 173:13-17 1996; and Selvin et al., Meth. Enzymol. 246:300-345, 1995. FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a fMAX multiwell fluorometer (Molecular Devices, Sunnyvale Calif.).

Scintillation proximity assay (SPA) is a particularly useful assay for detecting an interaction with the target molecule. SPA is widely used in the pharmaceutical industry and has been described (Hanselman et al., J. Lipid Res. 38:2365-2373 (1997); Kahl et al., Anal. Biochem. 243:282-283 (1996); Undenfriend et al., Anal. Biochem. 161:494-500 (1987)). See also U.S. Pat. Nos. 4,626,513 and 4,568,649, and European Patent No. 0,154,734. One commercially available system uses FLASHPLATE scintillant-coated plates (NEN Life Science Products, Boston, Mass.).

The target molecule can be bound to the scintillator plates by a variety of well known means. Scintillant plates are available that are derivatized to bind to fusion proteins such as GST, His6 or Flag fusion proteins. Where the target molecule is a protein complex or a multimer, one protein or subunit can be attached to the plate first, then the other components of the complex added later under binding conditions, resulting in a bound complex.

In a typical SPA assay, the gene products in the expression pool will have been radiolabeled and added to the wells, and allowed to interact with the solid phase, which is the immobilized target molecule and scintillant coating in the wells.

The assay can be measured immediately or allowed to reach equilibrium. Either way, when a radiolabel becomes sufficiently close to the scintillant coating, it produces a signal detectable by a device such as a TOPCOUNT NXT microplate scintillation counter (Packard BioScience Co., Meriden Conn.). If a radiolabeled expression product binds to the target molecule, the radiolabel remains in proximity to the scintillant long enough to produce a detectable signal.

In contrast, the labeled proteins that do not bind to the target molecule, or bind only briefly, will not remain near the scintillant long enough to produce a signal above background. Any time spent near the scintillant caused by random Brownian motion will also not result in a significant amount of signal. Likewise, residual unincorporated radiolabel used during the expression step may be present, but will not generate significant signal because it will be in solution rather than interacting with the target molecule. These non-binding interactions will therefore cause a certain level of background signal that can be mathematically removed. If too many signals are obtained, salt or other modifiers can be added directly to the assay plates until the desired specificity is obtained (Nichols et al., Anal. Biochem. 257:112-119, 1998).

In one embodiment, $Ca_v2$ channels are detected/quantified using a ligand binding assay, such as, for example, a radioligand binding assay. Briefly, a sample from a tissue expressing $Ca_v2$ channels is incubated with a suitable ligand under conditions designed to provide a saturating concentration of ligand over the incubation period. After ligand treatment, the sample is assayed for radioligand binding. Any ligand that binds to $Ca_v2$ channels can be employed in the assay, although N-type-selective calcium channel ligands are preferred. Any of the $Ca_v2$ channel modulators discussed above can, for example, be labeled and used in this assay. An exemplary, preferred ligand for this purpose is 125'-omega-conotoxin GVIA. Binding of this ligand to cells can be assayed as described, for example, in Solem et al. (1997) J. Pharmacol. Exp. Ther. 282:1487-95. Binding to membranes (e.g., brain membranes) can be assayed according to the method of Wagner et al. (1995) J. Neurosci. 8:3354-3359 (see also, the modifications of this method described in McMahon et al. (2000) Mol. Pharm. 57:53-58).

In another embodiment, channel subunit polypeptide(s) are detected/quantified in an electrophoretic polypeptide separation (e.g. a 1- or 2-dimensional electrophoresis). Means of detecting polypeptides using electrophoretic techniques are well known to those of skill in the art (see generally, R. Scopes (1982) Polypeptide Purification, Springer-Verlag, N.Y.; Deutscher, (1990) Methods in Enzymology Vol. 182: Guide to Polypeptide Purification, Academic Press, Inc., N.Y.).

A variation of this embodiment utilizes a Western blot (immunoblot) analysis to detect and quantify the presence channel subunit polypeptide(s) in the sample. This technique generally comprises separating sample polypeptides by gel electrophoresis on the basis of molecular weight, transferring the separated polypeptides to a suitable solid support (such as a nitrocellulose filter, a nylon filter, or derivatized nylon filter), and incubating the support with antibodies that specifically bind the target polypeptide(s). Antibodies that specifically bind to the target polypeptide(s) may be directly labeled or alternatively may be detected subsequently using labeled antibodies (e.g., labeled sheep anti-mouse antibodies) that specifically bind to a domain of the primary antibody.

In certain embodiments, channel subunit polypeptide(s) are detected and/or quantified in the biological sample using any of a number of well-known immunoassays (see, e.g., U.S. Pat. Nos. 4,366,241; 4,376,110; 4,517,288; and 4,837,168). For a general review of immunoassays, see also Methods in Cell Biology Volume 37: Antibodies in Cell Biology, Asai, ed. Academic Press, Inc. New York (1993); Basic and Clinical Immunology 7th Edition, Stites & Terr, eds. (1991).

Detectable labels suitable for use in the present invention include any moiety or composition detectable by spectroscopic, photochemical, biochemical, immunochemical, electrical, optical or chemical means. Examples include biotin for staining with a labeled streptavidin conjugate, magnetic beads (e.g., Dynabeads™), fluorescent dyes (e.g., fluorescein, texas red, rhodamine, coumarin, oxazine, green fluorescent protein, and the like, see, e.g., Molecular Probes, Eugene, Oreg., USA), radiolabels (e.g., 3H, 125I, 35S, 14C, or 32P), receptors (e.g., horseradish peroxidase, alkaline phosphatase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

The assays of this invention are scored (as positive or negative or quantity of target polypeptide) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of target polypeptide concentration.

In preferred embodiments, immunoassays according to the invention are carried out using a MicroElectroMechanical System (MEMS). MEMS are microscopic structures integrated onto silicon that combine mechanical, optical, and fluidic elements with electronics, allowing convenient detection of an analyte of interest. An exemplary MEMS device suitable for use in the invention is the Protiveris' multicantilever array. This array is based on chemo-mechanical actuation of specially designed silicon microcantilevers and subsequent optical detection of the microcantilever deflections. When coated on one side with a protein, antibody, antigen or DNA fragment, a microcantilever will bend when it is exposed to a solution containing the complementary molecule. This bending is caused by the change in the surface energy due to the binding event. Optical detection of the degree of bending (deflection) allows measurement of the amount of complementary molecule bound to the microcantilever.

Changes in Cav2 channel subunit expression level can be detected by measuring changes in levels of mRNA and/or a polynucleotide derived from the mRNA (e.g., reverse-transcribed cDNA, etc.).

Polynucleotides can be prepared from a sample according to any of a number of methods well known to those of skill in the art. General methods for isolation and purification of polynucleotides are described in detail in by Tijssen ed., (1993) Chapter 3 of Laboratory Techniques in Biochemistry and Molecular Biology: Hybridization With Nucleic Acid Probes, Part I. Theory and Nucleic Acid Preparation, Elsevier, N.Y. and Tijssen ed.

In one embodiment, amplification-based assays can be used to detect, and optionally quantify, a polynucleotide encoding a channel subunit of interest. In such amplification-based assays, the channel subunit mRNA in the sample act as template(s) in an amplification reaction carried out with a nucleic acid primer that contains a detectable label or component of a labeling system. Suitable amplification methods include, but are not limited to, polymerase chain reaction (PCR); reverse-transcription PCR (RT-PCR); ligase chain reaction (LCR) (see Wu and Wallace (1989) Genomics 4: 560, Landegren et al. (1988) Science 241: 1077, and Barringer et al. (1990) Gene 89: 117; transcription amplification (Kwoh et al. (1989) Proc. Natl. Acad. Sci. USA 86: 1173), self-sustained sequence replication (Guatelli et al. (1990) Proc. Nat. Acad. Sci. USA 87: 1874); dot PCR, and linker adapter PCR, etc.

To determine the level of the channel subunit mRNA, any of a number of well known "quantitative" amplification methods can be employed. Quantitative PCR generally involves simultaneously co-amplifying a known quantity of a control sequence using the same primers. This provides an internal standard that may be used to calibrate the PCR reaction. Detailed protocols for quantitative PCR are provided in PCR Protocols, A Guide to Methods and Applications, Innis et al., Academic Press, Inc. N.Y., (1990). Hybridization techniques are generally described in Hames and Higgins (1985) Nucleic Acid Hybridization, A Practical Approach, IRL Press; Gall and Pardue (1969) Proc. Natl. Acad. Sci. USA 63: 378-383; and John et al. (1969) Nature 223: 582-587. Methods of optimizing hybridization conditions are described, e.g., in Tijssen (1993) Laboratory Techniques in Biochemistry and Molecular Biology, Vol. 24: Hybridization With Nucleic Acid Probes, Elsevier, N.Y.).

The nucleic acid probes used herein for detection of channel subunit mRNA can be full-length or less than the full-length of these polynucleotides. Shorter probes are generally empirically tested for specificity. Preferably, nucleic acid probes are at least about 15, and more preferably about 20 bases or longer, in length. (See Sambrook et al. for methods of selecting nucleic acid probe sequences for use in nucleic acid hybridization.) Visualization of the hybridized probes allows the qualitative determination of the presence or absence of the channel subunit mRNA of interest, and standard methods (such as, e.g., densitometry where the nucleic acid probe is radioactively labeled) can be used to quantify the level of the channel subunit polynucleotide.). A variety of additional nucleic acid hybridization formats are known to those skilled in the art. Standard formats include sandwich assays and competition or displacement assays. Sandwich assays are commercially useful hybridization assays for detecting or isolating polynucleotides.

In one embodiment, the methods of the invention can be utilized in array-based hybridization formats. In an array format, a large number of different hybridization reactions can be run essentially "in parallel." This provides rapid, essentially simultaneous, evaluation of a number of hybridizations in a single experiment. Methods of performing hybridization reactions in array based formats are well known to those of skill in the art (see, e.g., Pastinen (1997) Genome Res. 7: 606-614; Jackson (1996) Nature Biotechnology 14:1685; Chee (1995) Science 274: 610; WO 96/17958, Pinkel et al. (1998) Nature Genetics 20: 207-211). See also, for example, U.S. Pat. No. 5,807,522 describes the use of an automated system that taps a microcapillary against a surface to deposit a small volume of a biological sample. The process is repeated to generate high-density arrays. Arrays can also be produced using oligonucleotide synthesis technology. Thus, for example, U.S. Pat. No. 5,143,854 and PCT Patent Publication Nos. WO 90/15070 and 92/10092 teach the use of light-directed combinatorial synthesis of high-density oligonucleotide microarrays. Synthesis of high-density arrays is also described in U.S. Pat. Nos. 5,744,305; 5,800,992; and 5,445,934.

Many methods for immobilizing nucleic acids on a variety of solid surfaces are known in the art. A wide variety of organic and inorganic polymers, as well as other materials, both natural and synthetic, can be employed as the material for the solid surface. Illustrative solid surfaces include, e.g., nitrocellulose, nylon, glass, quartz, diazotized membranes (paper or nylon), silicones, polyformaldehyde, cellulose, and cellulose acetate. In addition, plastics such as polyethylene, polypropylene, polystyrene, and the like can be used. Other materials that can be employed include paper, ceramics, metals, metalloids, semiconductive materials, and the like. In addition, substances that form gels can be used. Such materials include, e.g., proteins (e.g., gelatins), lipopolysaccharides, silicates, agarose and polyacrylamides. Where the solid surface is porous, various pore sizes may be employed depending upon the nature of the system.

Hybridization assays according to the invention can also be carried out using a MicroElectroMechanical System (MEMS), such as the Protiveris' multicantilever array.

Channel subunit RNA is detected in the above-described polynucleotide-based assays by means of a detectable label. Any of the labels discussed above can be used in the polynucleotide-based assays of the invention. The label may be added to a probe or primer or sample polynucleotides prior to, or after, the hybridization or amplification. So called "direct labels" are detectable labels that are directly attached to or incorporated into the labeled polynucleotide prior to conducting the assay. In contrast, so called "indirect labels" are joined to the hybrid duplex after hybridization. In indirect labeling, one of the polynucleotides in the hybrid duplex carries a component to which the detectable label binds. Thus, for example, a probe or primer can be biotinylated before hybridization. After hybridization, an avidin-conjugated fluorophore can bind the biotin-bearing hybrid duplexes, providing a label that is easily detected. For a detailed review of methods of the labeling and detection of polynucleotides, see Laboratory Techniques in Biochemistry and Molecular Biology, Vol. 24: Hybridization With Nucleic Acid Probes, P. Tijssen, ed. Elsevier, N.Y., (1993)).

The sensitivity of the hybridization assays can be enhanced through use of a polynucleotide amplification system that multiplies the target polynucleotide being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

The invention also provides a screening method based on determining the effect, if any, of a test agent on the level of the depolarization-induced inward calcium current mediated by Cav2 channels. Agents that reduce this current can potentially reduce one or more drug-related effects and/or behaviors. Conversely, agents that increase this current can potentially enhance such drug-related effects and/or behaviors.

The calcium current can be measured using any available technique An indirect measurement of calcium current can be carried out described by McMahon et al. (2000) Mol. Pharm. 57:53-58). In this method, cells are loaded with a dye that fluoresces in the presence of calcium (such as fura-2 AM) prior to depolarization. Cells are generally also preincubated in the presence or absence of an Cav2 channel-specific modulator (e.g., 1 uM omega-conotoxin GVIA) to determine the extent of the calcium current that is attributable to Cav2 channels. Cells are subsequently depolarized by incubation in a 50 mM KCl buffer in the continued presence or absence of the modulator. The resulting calcium current can then be calculated based on fluorescence, as described by Solem et al. (1997) J. Pharmacol. Exp. Ther. 282:1487-95. Ruiz-Velasco and Ikeda (J. Neuroscience (2000) 20:2183-91 describe the direct measurement of calcium currents using a whole-cell variant of the patch-claim technique, which can also be employed in the present invention.

Cells useful for screening based on calcium current include any of those described above in connection with screening based levels of Cav2 channels or channel subunit polypeptides or RNA or described below in the Examples.

In one embodiment, the test agent is contacted with the cell in the presence of the drug. The drug is generally one that produces one or more undesirable effects or behaviors, such as, for example, sedative-hypnotic and analgesic drugs. In particular embodiments, the drug is ethanol, a cannabinioid, or an opioid.

In a preferred embodiment, generally involving the screening of a large number of test agents, the screening method includes the recordation of any test agent selected in any of the above-described prescreening or screening methods in a database of agents that may modulate a drug-related effect or behavior. The term "database" refers to a means for recording and retrieving information. In preferred embodiments, the database also provides means for sorting and/or searching the stored information. The database can employ any convenient medium including, but not limited to, paper systems, card systems, mechanical systems, electronic systems, optical systems, magnetic systems or combinations thereof. Preferred databases include electronic (e.g. computer-based) databases. Computer systems for use in storage and manipulation of databases are well known to those of skill in the art and include, but are not limited to "personal computer systems," mainframe systems, distributed nodes on an inter- or intranet, data or databases stored in specialized hardware (e.g. in microchips), and the like.

Test Agents Identified by Screening

When a test agent is found to modulate one or more $Ca_v2$ channels, channel subunit polypeptide or RNA, or depolarization-induced inward calcium current, a preferred screening method of the invention further includes combining the test agent with a carrier, preferably pharmaceutically acceptable carrier, such as are described above. Generally, the concentration of test agent is sufficient to alter the level of Cav2 channels, channel subunit polypeptide or RNA, or depolarization-induced inward calcium current when the composition is contacted with a cell. This concentration will vary, depending on the particular test agent and specific application for which the composition is intended. As one skilled in the art appreciates, the considerations affecting the formulation of a test agent with a carrier are generally the same as described above with respect to methods of reducing a drug-related effect or behavior.

In a preferred embodiment, the test agent is administered to an animal to measure the ability of the selected test agent to modulate a drug-related effect or behavior in a subject, as described in greater detail below.

In one embodiment, the $Ca_v2$ modulator is an enhancer of an analgesic agent. To screen for this effect, a test agent, e.g., an agent identified in one or more of the screens described herein, is administered to the subject before, during, and/or after administration of the analgesic of interest, and the subject is tested or observed to determine whether the test agent modulates a particular analgesic effect or behavior. Test agents can be administered by any suitable route, as described above for Cav2 channel modulators. Generally, the concentration of test agent is sufficient to alter the level of $Ca_v2$ channels, reduce the amount of analgesic necessary for an angelsic effect or reduce addictive amounts of the analgesic, reduced channel subunit polypeptide or RNA, or depolarization-induced inward calcium current in vivo.

The analgesic effect or behavior studied can be any of those described above. The analgesic is administered by any suitable route and in an amount sufficient to produce the analgesic effect or behavior under examination. The analgesic effect or behavior is measured and compared with that observed in the absence of test agent and/or in the presence of a lower amount of test agent.

Preferred compositions for use in the therapeutic methods of the invention inhibit the Cav2 channel function by about 5% based on, for example, compound state analysis techniques or modulatory profiles described infra, more preferably about 7.5% or 10% inhibition of the calcium channel and still more preferable, at least about 20%, 30%, 40%, 50%, 60%, 70%, 80%, 90% or 100% inhibition of the calcium channel.

Compositions

Soluble polypeptides derived from $Ca_v2$ channel that retain the ability to bind predominant modulation determinant of a calcium channel are useful. In addition, modification of such residues may permit the skilled artisan to tailor the binding specificities and/or affinity of polypeptides.

Polypeptides of particular interest include N—($Ca_v2.2$), P/Q-($Ca_v2.1$) or R-type ($Ca_v2.3$) calcium channels' predominant modulation determinant regions. The $Ca_v2$ channels are of particular interest because they are of interest in the treatment, prevention, amelioration, reduction or alleviation of diseases.

The polypeptides may be prepared in various ways including, for example, molecular biological techniques, including proteolytic digestion of cells or cellular membrane preparations comprising the receptor (Bartfeld et al., Active acetylcholine receptor fragment obtained by tryptic digestion of acetylcholine receptor from Torpedo californica, Biochem Biophys Res Commun. 89:512-9, 1979; Borhani et al., Crystallization and X-ray diffraction studies of a soluble form of the human transferrin receptor, J. Mol. Biol. 218:685-9, 1991), recombinant DNA technologies (Marlovits et al., Recombinant soluble low-density lipoprotein receptor fragment inhibits common cold infection, J Mol. Recognit. 11:49-51, 1998; Huang et al., Expression of a human thyrotrophin receptor fragment in *Escherichia coli* and its interaction with the hormone and autoantibodies from subjects with Graves' disease, J Mol. Endocrinol. 8:137-44, 1992), or by in vitro synthesis of oligopeptides.

Peptidomimetics

In general, a polypeptide mimetic ("peptidomimetic") is a molecule that mimics the biological activity of a polypeptide, but that is not peptidic in chemical nature. While, in certain embodiments, a peptidomimetic is a molecule that contains no peptide bonds (that is, amide bonds between amino acids), the term peptidomimetic may include molecules that are not completely peptidic in character, such as pseudo-peptides, semi-peptides and peptoids. Examples of some peptidomimetics by the broader definition (e.g., where part of a polypeptide is replaced by a structure lacking peptide bonds) are described below. Whether completely or partially non-peptide in character, peptidomimetics according to this invention may provide a spatial arrangement of reactive chemical moieties that closely resembles the three-dimensional arrangement of active groups in a polypeptide. As a result of this similar active-site geometry, the peptidomimetic may exhibit biological effects that are similar to the biological activity of a polypeptide.

There are several potential advantages for using a mimetic of a given polypeptide rather than the polypeptide itself. For example, polypeptides may exhibit two undesirable attributes, i.e., poor bioavailability and short duration of action. Peptidomimetics are often small enough to be both orally active and to have a long duration of action. There are also problems associated with stability, storage and immunoreactivity for polypeptides that may be obviated with peptidomimetics.

Candidate, lead and other polypeptides having a desired biological activity can be used in the development of peptidomimetics with similar biological activities. Techniques of developing peptidomimetics from polypeptides are known. Peptide bonds can be replaced by non-peptide bonds that allow the peptidomimetic to adopt a similar structure, and therefore biological activity, to the original polypeptide. Further modifications can also be made by replacing chemical groups of the amino acids with other chemical groups of similar structure, shape or reactivity. The development of peptidomimetics can be aided by determining the tertiary structure of the original polypeptide, either free or bound to a ligand, by NMR spectroscopy, crystallography and/or computer-aided molecular modeling. These techniques aid in the development of novel compositions of higher potency and/or greater bioavailability and/or greater stability than the original polypeptide (Dean (1994), BioEssays, 16: 683-687; Cohen and Shatzmiller (1993), J. Mol. Graph., 11: 166-173; Wiley and Rich (1993), Med. Res. Rev., 13: 327-384; Moore (1994), Trends Pharmacol. Sci., 15: 124-129; Hruby (1993), Biopolymers, 33: 1073-1082; Bugg et al. (1993), Sci. Am., 269: 92-98, all incorporated herein by reference].

Specific examples of peptidomimetics are set forth below. These examples are illustrative and not limiting in terms of the other or additional modifications.

Peptides With A Reduced Isostere Pseudopeptide Bond

Proteases act on peptide bonds. Substitution of peptide bonds by pseudopeptide bonds may confer resistance to proteolysis or otherwise make a compound less labile. A number of pseudopeptide bonds have been described that in general do not affect polypeptide structure and biological activity. The reduced isostere pseudopeptide bond is a suitable pseudopeptide bond that is known to enhance stability to enzymatic cleavage with no or little loss of biological activity (Couder, et al., (1993), Int. J. Polypeptide Protein Res. 41:181-184, incorporated herein by reference). Thus, the amino acid sequences of these compounds may be identical to the sequences of their parent L-amino acid polypeptides, except that one or more of the peptide bonds are replaced by an isostere pseudopeptide bond. Preferably the most N-terminal peptide bond is substituted, since such a substitution would confer resistance to proteolysis by exopeptidases acting on the N-terminus.

Peptides with a Retro-Inverso Pseudopeptide Bond

To confer resistance to proteolysis, peptide bonds may also be substituted by retro-inverso pseudopeptide bonds (Dalpozzo, et al. (1993), Int. J. Polypeptide Protein Res. 41:561-566, incorporated herein by reference). According to this modification, the amino acid sequences of the compounds may be identical to the sequences of their L-amino acid parent polypeptides, except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus.

Peptoid Derivatives

Peptoid derivatives of polypeptides represent another form of modified polypeptides that retain the important structural determinants for biological activity, yet eliminate the peptide bonds, thereby conferring resistance to proteolysis (Simon, et al., 1992, Proc. Natl. Acad. Sci. USA, 89:9367-9371 and incorporated herein by reference). Peptoids are oligomers of N-substituted glycines. A number of N-alkyl groups have been described, each corresponding to the side chain of a natural amino acid.

Polypeptides

The polypeptides of this invention, including the analogs and other modified variants, may generally be prepared following known techniques. Preferably, synthetic production of the polypeptide of the invention may be according to the solid phase synthetic method. For example, the solid phase synthesis is well understood and is a common method for preparation of polypeptides, as are a variety of modifications of that technique [Merrifield (1964), J. Am. Chem. Soc., 85: 2149; Stewart and Young (1984), Solid Phase polypeptide Synthesis, Pierce Chemical Company, Rockford, Ill.; Bodansky and Bodanszky (1984), The Practice of polypeptide Synthesis, Springer-Verlag, New York; Atherton and Sheppard (1989), Solid Phase polypeptide Synthesis: A Practical Approach, IRL Press, New York].

Alternatively, polypeptides of this invention may be prepared in recombinant systems using polynucleotide sequences encoding the polypeptides. For example, fusion proteins are typically prepared using recombinant DNA technology.

Polypeptide Derivatives

A "derivative" of a polypeptide is a compound that is not, by definition, a polypeptide, i.e., it contains at least one chemical linkage that is not a peptide bond. Thus, polypeptide derivatives include without limitation proteins that naturally undergo post-translational modifications such as, e.g., glycosylation. It is understood that a polypeptide of the invention may contain more than one of the following modifications within the same polypeptide. Preferred polypeptide derivatives retain a desirable attribute, which may be biological activity; more preferably, a polypeptide derivative is enhanced with regard to one or more desirable attributes, or has one or more desirable attributes not found in the parent polypeptide.

Mutant Polypeptides: A polypeptide having an amino acid sequence identical to that found in a protein prepared from a natural source is a "wildtype" polypeptide. Mutant oligopeptides can be prepared by chemical synthesis, including without limitation combinatorial synthesis.

Mutant polypeptides larger than oligopeptides can be prepared using recombinant DNA technology by altering the nucleotide sequence of a nucleic acid encoding a polypeptide. Although some alterations in the nucleotide sequence will not alter the amino acid sequence of the polypeptide encoded thereby ("silent" mutations), many will result in a polypeptide having an altered amino acid sequence that is altered relative to the parent sequence. Such altered amino acid sequences may comprise substitutions, deletions and additions of amino acids, with the proviso that such amino acids are naturally occurring amino acids.

Thus, subjecting a nucleic acid that encodes a polypeptide to mutagenesis is one technique that can be used to prepare mutant polypeptides, particularly ones having substitutions of amino acids but no deletions or insertions thereof. A variety of mutagenic techniques are known that can be used in vitro or in vivo including without limitation chemical mutagenesis and PCR-mediated mutagenesis. Such mutagenesis may be randomly targeted (i.e., mutations may occur anywhere within the nucleic acid) or directed to a section of the nucleic acid that encodes a stretch of amino acids of particular interest. Using such techniques, it is possible to prepare randomized, combinatorial or focused compound libraries, pools and mixtures.

Polypeptides having deletions or insertions of naturally occurring amino acids may be synthetic oligopeptides that result from the chemical synthesis of amino acid sequences that are based on the amino acid sequence of a parent polypeptide but which have one or more amino acids inserted or deleted relative to the sequence of the parent polypeptide. Insertions and deletions of amino acid residues in polypeptides having longer amino acid sequences may be prepared by directed mutagenesis.

Chemically Modified Polypeptides: As contemplated by this invention, the term "polypeptide" includes those having one or more chemical modification relative to another polypeptide, i.e., chemically modified polypeptides. The polypeptide from which a chemically modified polypeptide is derived may be a wildtype protein, a mutant protein or a mutant polypeptide, or polypeptide fragments thereof, an antibody or other polypeptide ligand according to the invention including without limitation single-chain antibodies, bacterial proteins and polypeptide derivatives thereof, or polypeptide ligands prepared according to the disclosure. Preferably, the chemical modification(s) confer(s) or improve(s) desirable attributes of the polypeptide but does not substantially alter or compromise the biological activity thereof. Desirable attributes include but are limited to increased shelf-life; enhanced serum or other in vivo stability; resistance to proteases; and the like. Such modifications include by way of non-limiting example N-terminal acetylation, glycosylation, and biotinylation.

Polypeptides with N-Terminal or C-Terminal Chemical Groups: An effective approach to confer resistance to peptidases acting on the N-terminal or C-terminal residues of a polypeptide is to add chemical groups at the polypeptide termini, such that the modified polypeptide is no longer a substrate for the peptidase. One such chemical modification is glycosylation of the polypeptides at either or both termini. Certain chemical modifications, in particular N-terminal glycosylation, have been shown to increase the stability of polypeptides in human serum (Powell et al. (1993), Pharma. Res. 10: 1268-1273). Other chemical modifications which enhance serum stability include, but are not limited to, the addition of an N-terminal alkyl group, consisting of a lower alkyl of from 1 to 20 carbons, such as an acetyl group, and/or the addition of a C-terminal amide or substituted amide group.

Polypeptides with a Terminal D-Amino Acid: The presence of an N-terminal D-amino acid increases the serum stability of a polypeptide that otherwise contains L-amino acids, because exopeptidases acting on the N-terminal residue cannot utilize a D-amino acid as a substrate. Similarly, the presence of a C-terminal D-amino acid also stabilizes a polypeptide, because serum exopeptidases acting on the C-terminal residue cannot utilize a D-amino acid as a substrate. With the exception of these terminal modifications, the amino acid sequences of polypeptides with N-terminal and/or C-terminal D-amino acids are usually identical to the sequences of the parent L-amino acid polypeptide.

Polypeptides With Substitution of Natural Amino Acids By Unnatural Amino Acids: Substitution of unnatural amino acids for natural amino acids in a subsequence of a polypeptide can confer or enhance desirable attributes including biological activity. Such a substitution can, for example, confer resistance to proteolysis by exopeptidases acting on the N-terminus. The synthesis of polypeptides with unnatural amino acids is routine and known in the art (see, for example, Coller, et al. (1993), cited above).

Post-Translational Chemical Modifications: Different host cells will contain different post-translational modification mechanisms that may provide particular types of post-translational modification of a fusion protein if the amino acid sequences required for such modifications is present in the fusion protein. A large number (.about. 100) of post-translational modifications have been described, a few of which are discussed herein. One skilled in the art will be able to choose appropriate host cells, and design chimeric genes that encode protein members comprising the amino acid sequence needed for a particular type of modification.

Glycosylation is one type of post-translational chemical modification that occurs in many eukaryotic systems, and may influence the activity, stability, pharmacogenetics, immunogenicity and/or antigenicity of proteins. However, specific amino acids must be present at such sites to recruit the appropriate glycosylation machinery, and not all host cells have the appropriate molecular machinery. *Saccharomyces cerevisieae* and *Pichia pastoris* provide for the production of glycosylated proteins, as do expression systems that utilize insect cells, although the pattern of glyscoylation may vary depending on which host cells are used to produce the fusion protein.

Another type of post-translation modification is the phosphorylation of a free hydroxyl group of the side chain of one or more Ser, Thr or Tyr residues. Protein kinases catalyze such reactions. Phosphorylation is often reversible due to the action of a protein phosphatase, an receptor that catalyzes the dephosphorylation of amino acid residues.

Differences in the chemical structure of amino terminal residues result from different host cells, each of which may have a different chemical version of the methionine residue encoded by a start codon, and these will result in amino termini with different chemical modifications.

For example, many or most bacterial proteins are synthesized with an amino terminal amino acid that is a modified form of methionine, i.e., N-formyl-methionine (fMct). Although the statement is often made that all bacterial proteins are synthesized with an fMet initiator amino acid; although this may be true for *E. coli*, recent studies have shown that it is not true in the case of other bacteria such as *Pseudomonas aeruginosa* (Newton et al., J. Biol. Chem. 274: 22143-22146, 1999). In any event, in *E. coli*, the formyl group of fMet is usually enzymatically removed after translation to yield an amino terminal methionine residue, although the entire fMet residue is sometimes removed (see Hershey, Chapter 40, "Protein Synthesis" in: *Escherichia Coli* and *Salmonella Typhimurium*: Cellular and Molecular Biology, Neidhardt, Frederick C., Editor in Chief, American Society for Microbiology, Washington, D.C., 1987, Volume 1, pages 613-647, and references cited therein.) *E. coli* mutants that lack the receptors (such as, e.g., formylase) that catalyze such post-translational modifications will produce proteins having an amino terminal fMet residue (Guillon et al., J. Bacteriol. 174:4294-4301, 1992).

In eukaryotes, acetylation of the initiator methionine residue, or the penultimate residue if the initiator methionine has been removed, typically occurs co- or post-translationally. The acetylation reactions are catalyzed by N-terminal acetyltransferases (NATs, a.k.a. N-alpha-acetyltransferases), whereas removal of the initiator methionine residue is catalyzed by methionine aminopeptidases (for reviews, see Bradshaw et al., Trends Biochem. Sci. 23:263-267, 1998; and Driessen et al., CRC Crit. Rev. Biochem. 18:281-325, 1985). Amino terminally acetylated proteins are said to be "N-acetylated," "N alpha acetylated" or simply "acetylated."

Another post-translational process that occurs in eukaryotes is the alpha-amidation of the carboxy terminus. For reviews, see Eipper et al. Annu. Rev. Physiol. 50:333-344, 1988, and Bradbury et al. Lung Cancer 14:239-251, 1996. About 50% of known endocrine and neuroendocrine peptide hormones are alpha-amidated (Treston et al., Cell Growth Differ. 4:911-920, 1993). In most cases, carboxy alpha-amidation is required to activate these peptide hormones.

Substitutions encompass amino acid alterations in which an amino acid is replaced with a different naturally-occurring or a non-conventional amino acid residue. Such substitutions may be classified as "conservative", in which case an amino acid residue contained in a peptide is replaced with another naturally-occurring amino acid of similar character, for example Gly to Ala, Asp to Glu, Asn to Gln or Trp to Tyr. Possible alternative amino acids include serine or threonine, aspartate or glutamate or carboxyglutamate, proline or hydroxyproline, arginine or lysine, asparagine or histidine, histidine or asparagine, tyrosine or phenylalanine or tryptophan, aspartate or glutamate, isoleucine or leucine or valine.

It is to be understood that some non-conventional amino acids may also be suitable replacements for the naturally occurring amino acids. Substitutions encompassed by the present invention may also be "non-conservative", in which an amino acid residue which is present in a polypeptide is substituted with an amino acid having different properties, such as naturally-occurring amino acid from a different group (e.g. substituting a charged or hydrophilic or hydrophobic amino acid with alanine), or alternatively, in which a naturally-occurring amino acid is substituted with a non-conventional amino acid. Additions encompass the addition of one or more naturally occurring or non-conventional amino acid residues. Deletions encompass the deletion of one or more amino acid residues.

One of skill in the art can identify other peptides and understands that homologues and orthologues of these molecules are useful in the compositions and methods of the instant invention. Moreover, variants of the peptides, are useful in the methods and compositions of the invention.

One of skill in the art will understand that molecules that share one or more functional activities with the molecules identified above, but have differences in amino acid or nucleic acid sequence would be useful in the compositions and methods of the invention. For example, in a preferred embodiment, a polypeptide or biologically active fragment thereof has at least about 60%, 70%, 80%, 90%, 95%, 96%, 97%, 98%, 99%, or 100% identity with the polypeptide set forth as SEQ ID NO: 1-3, or a fragment or variant thereof.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman et al. (1970, *J. Mol. Biol.* 48:444-453) algorithm which has been incorporated into the GAP program in the GCG software package (available at http://www.gcg.com), using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a BLOSUM 62 scoring matrix with a gap penalty of 12, a gap extend penalty of 4, and a frameshift gap penalty of 5.

The percent identity between two amino acid or nucleotide sequences can be determined using the algorithm of Meyers et al. (1989, CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences that one of skill in the art could use to make the molecules of the invention. Such searches can be performed using the NBLAST and XBLAST programs (version 2.0) of Altschul, et al. (1990, *J. Mol. Biol.* 215:403-410). BLAST nucleotide searches can be performed with the NBLAST program, score=100, wordlength=12 to obtain nucleotide sequences homologous to 13245 nucleic acid molecules of the invention. BLAST protein searches can be performed with the XBLAST program, score=50, wordlength=3 to obtain amino acid sequences homologous to 13245 protein molecules of the invention. To obtain gapped alignments for comparison purposes, gapped BLAST can be utilized as described in Altschul et al. (1997, *Nucl. Acids Res.* 25:3389-3402). When using BLAST and gapped BLAST programs, the default parameters of the respective programs (e.g., XBLAST and NBLAST) can be used.

Vectors

Another aspect of the invention pertains to vectors, preferably expression vectors, containing a nucleic acid molecule encoding the fusion molecules, or components thereof, of the invention as described above. As used herein, the term "vector" refers to a nucleic acid molecule capable of transporting another nucleic acid molecule to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid molecule of the invention in a form suitable for expression of the nucleic acid molecule in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., fusion molecules comprising a chemokine receptor ligand and a toxin moiety).

The recombinant expression vectors of the invention can be designed for expression of the polypeptides of the invention in prokaryotic or eukaryotic cells. For example, the polypeptides can be expressed in bacterial cells such as *E. coli*, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) Gene 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) Nucleic Acids Res. 20:2111-2118). Such alteration of nucleic acid sequences of the invention can be carried out by standard DNA synthesis techniques.

In another embodiment, the expression vector is a yeast expression vector. Examples of vectors for expression in yeast *S. cerivisae* include pYepSec1 (Baldari, et al., (1987) *EMBO J.* 6:229-234), pMFa (Kudjan and Herskowitz, (1982) *Cell* 30:933-943), pJRY88 (Schultz et al., (1987) *Gene* 54:113-123), pYES2 (Invitrogen Corporation, San Diego, Calif.), and picZ (InVitrogen Corp, San Diego, Calif.).

Alternatively, the polypeptides can be expressed in insect cells using baculovirus expression vectors. Baculovirus vectors available for expression of proteins in cultured insect cells (e.g., Sf9 cells) include the pAc series (Smith et al. (1983) *Mol. Cell. Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) EMBO J. 8:729-733) and immunoglobulins (Banedji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

Another aspect of the invention pertains to host cells into which a nucleic acid molecule encoding a fusion polypeptide of the invention is introduced within a recombinant expression vector or a nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a fusion polypeptide of the invention can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding the polypeptide of the invention or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) the polypeptides of the invention. Accordingly, the invention further provides methods for producing polypeptides using the host cells of the invention. In one embodiment, the method comprises culturing the host cell of the invention (into which a recombinant expression vector encoding a polypeptide of the invention has been introduced) in a suitable medium such that a polypeptides of the invention is produced. In another embodiment, the method further comprises isolating the polypeptide from the medium or the host cell.

The host cells of the invention can also be used to produce non-human transgenic animals. For example, in one embodiment, a host cell of the invention is a fertilized oocyte or an embryonic stem cell into which coding sequences have been introduced. Such host cells can then be used to create non-human transgenic animals in which exogenous sequences have been introduced into their genome or homologous recombinant animals in which endogenous sequences have been altered. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like.

Methods of Making the Molecules of the Invention

As described above, molecules of the invention may be made recombinantly using the nucleic acid molecules, vectors, host cells and recombinant organisms described above.

Alternatively, the peptide can be made synthetically, or isolated from a natural source and linked to the carbohydrate recognition domain using methods and techniques well known to one of skill in the art.

Further, to increase the stability or half life of the fusion molecules of the invention, the polypeptides may be made, e.g., synthetically or recombinantly, to include one or more peptide analogs or mimmetics. Exemplary peptides can be synthesized to include D-isomers of the naturally occurring amino acid residues or amino acid analogs to increase the half life of the molecule when administered to a subject.

Pharmaceutical Compositions

The nucleic acid and polypeptide fusion molecules (also referred to herein as "active compounds") of the invention can be incorporated into pharmaceutical compositions. Such compositions typically include the nucleic acid molecule or protein, and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions of the instant invention may also include one or more other active compounds. Alternatively, the pharmaceutical compositions of the invention may be administered with one or more other active compounds. Other active compounds that can be administered with the pharmaceutical compounds of the invention, or formulated into the pharmaceutical compositions of the invention, include, for example, anti-inflammatory compounds.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Preferred pharmaceutical compositions of the invention are those that allow for local delivery of the active ingredient, e.g., delivery directly to the location of a tumor. Although systemic administration is useful in certain embodiments, local administration is preferred in most embodiments.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™. (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, kit or dispenser together with instructions, e.g., written instructions, for administration, particularly such instructions for use of the active agent to treat against a disorder or disease as disclosed herein, including a Cav2 disorder. The container, pack, kit or dispenser may also contain, for example, a nucleic acid sequence encoding a peptide, or a peptide expressing cell.

For research and therapeutic applications, an $Ca_v2$ channel modulator is generally formulated to deliver modulator to a target site in an amount sufficient to inhibit Cav2 channels at that site.

Modulator compositions or peptides of the invention optionally contain other components, including, for example, a storage solution, such as a suitable buffer, e.g., a physiological buffer. In a preferred embodiment, the composition is a pharmaceutical composition and the other component is a pharmaceutically acceptable carrier, such as are described in Remington's Pharmaceutical Sciences (1980) 16th editions, Osol, ed., 1980.

A pharmaceutically acceptable carrier suitable for use in the invention is non-toxic to cells, tissues, or subjects at the dosages employed, and can include a buffer (such as a phosphate buffer, citrate buffer, and buffers made from other organic acids), an antioxidant (e.g., ascorbic acid), a low-molecular weight (less than about 10 residues) peptide, a polypeptide (such as serum albumin, gelatin, and an immunoglobulin), a hydrophilic polymer (such as polyvinylpyrrolidone), an amino acid (such as glycine, glutamine, asparagine, arginine, and/or lysine), a monosaccharide, a disaccharide, and/or other carbohydrates (including glucose, mannose, and dextrins), a chelating agent (e.g., ethylenediaminetetratacetic acid [EDTA]), a sugar alcohol (such as mannitol and sorbitol), a salt-forming counterion (e.g., sodium), and/or an anionic surfactant (such as Tween™, Pluronics™, and PEG). In one embodiment, the pharmaceutically acceptable carrier is an aqueous pH-buffered solution.

Certain embodiments include sustained-release pharmaceutical compositions. An exemplary sustained-release composition has a semipermeable matrix of a solid hydrophobic polymer to which the modulator is attached or in which the modulator is encapsulated. Examples of suitable polymers include a polyester, a hydrogel, a polylactide, a copolymer of L-glutamic acid and T-ethyl-L-glutamase, non-degradable ethylene-vinylacetate, a degradable lactic acid-glycolic acid copolymer, and poly-D-(–)-3-hydroxybutyric acid. Such matrices are in the form of shaped articles, such as films, or microcapsules.

Where the modulator is a polypeptide, exemplary sustained release compositions include the polypeptide attached, typically via epsilon-amino groups, to a polyalkylene glycol (e.g., polyethylene glycol [PEG]). Attachment of PEG to proteins is a well-known means of reducing immunogenicity and extending in vivo half-life (see, e.g., Abuchowski, J., et al. (1977) J. Biol. Chem. 252:3582-86. Any conventional "pegylation" method can be employed, provided the "pegylated" variant retains the desired function(s).

In another embodiment, a sustained-release composition includes a liposomally entrapped modulator. Liposomes are small vesicles composed of various types of lipids, phospholipids, and/or surfactants. These components are typically arranged in a bilayer formation, similar to the lipid arrangement of biological membranes. Liposomes containing Cav2 channel modulators are prepared by known methods, such as, for example, those described in Epstein, et al. (1985) PNAS USA 82:3688-92, and Hwang, et al., (1980) PNAS USA, 77:4030-34. Ordinarily the liposomes in such preparations are of the small (about 200-800 Angstroms) unilamellar type in which the lipid content is greater than about 30 mol. percent cholesterol, the specific percentage being adjusted to provide the optimal therapy. Useful liposomes can be generated by the reverse-phase evaporation method, using a lipid composition including, for example, phosphatidylcholine, cholesterol, and PEG-derivatized phosphatidylethanolamine (PEG-PE). If desired, liposomes are extruded through filters of defined pore size to yield liposomes of a particular diameter.

Pharmaceutical compositions can also include an modulator adsorbed onto a membrane, such as a silastic membrane, which can be implanted, as described in International Publication No. WO 91/04014.

Pharmaceutical compositions of the invention can be stored in any standard form, including, e.g., an aqueous solution or a lyophilized cake. Such compositions are typically sterile when administered to subjects. Sterilization of an aqueous solution is readily accomplished by filtration through a sterile filtration membrane. If the composition is stored in lyophilized form, the composition can be filtered before or after lyophilization and reconstitution.

In particular embodiments, the methods of the invention employ pharmaceutical compositions containing a polynucleotide encoding a polypeptide modulator of Cav2 channels. Such compositions optionally include other components, as for example, a storage solution, such as a suitable buffer, e.g., a physiological buffer. In a preferred embodiment, the composition is a pharmaceutical composition and the other component is a pharmaceutically acceptable carrier as described above.

Preferably, compositions containing polynucleotides useful in the invention also include a component that facilitates entry of the polynucleotide into a cell. Components that facilitate intracellular delivery of polynucleotides are well-known and include, for example, lipids, liposomes, water-oil emulsions, polyethylene imines and dendrimers, any of which can be used in compositions according to the invention. Lipids are among the most widely used components of this type, and any of the available lipids or lipid formulations can be employed with polynucleotides useful in the invention. Typically, cationic lipids are preferred. Preferred cationic lipids include N-[1-(2,3-dioleyloxy)pro-pyl]-n,n,n-trimethylammonium chloride (DOTMA), dioleoyl phosphotidylethanolamine (DOPE), and/or dioleoyl phosphatidylcholine (DOPC). Polynucleotides can also be entrapped in liposomes, as described above.

In another embodiment, polynucleotides are complexed to dendrimers, which can be used to introduce polynucleotides into cells. Dendrimer polycations are three-dimensional, highly ordered oligomeric and/or polymeric compounds typically formed on a core molecule or designated initiator by reiterative reaction sequences adding the oligomers and/or polymers and providing an outer surface that is positively changed. Suitable dendrimers include, but are not limited to, "starburst" dendrimers and various dendrimer polycations. Methods for the preparation and use of dendrimers to introduce polynucleotides into cells in vivo are well known to those of skill in the art and described in detail, for example, in PCT/US83/02052 and U.S. Pat. Nos. 4,507,466; 4,558,120; 4,568,737; 4,587,329; 4,631,337; 4,694,064; 4,713,975; 4,737,550; 4,871,779; 4,857,599; and 5,661,025.

For therapeutic use, polynucleotides useful in the invention are formulated in a manner appropriate for the particular indication. U.S. Pat. No. 6,001,651 to Bennett et al. describes a number of pharmaceutical compositions and formulations suitable for use with an oligonucleotide therapeutic as well as methods of administering such oligonucleotides.

Transgenic Animals

The transgenic non-human animal may be a primate, mouse, dog, cat, sheep, horse, rabbit or other non-human animal. Cells may be isolated and cultured from the transgenic non-human animals. The cells may be used in, for example, primary cultures or established cultures.

A transgenic non-human animal comprising an over-expressed NTB peptide or a fragment or variant thereof. The use of a transgenic animal according to claim 50, to test therapeutic agents. Embodiments of the invention include the use of the ES cell lines derived from the transgenic zygote, embryo, blastocyst or non-human animal to treat human and non-human animal diseases.

Transgenic non-human animals include those whose genome comprises over-expressed $NT_B$ peptide or a fragment or variant thereof comprising the nucleic acid sequence set forth in SEQ ID NO: 1-3, or a fragments or variants thereof. The methods are useful for producing transgenic and chimeric animals of most vertebrate species. Such species include, but are not limited to, nonhuman mammals, including rodents such as mice and rats, rabbits, ovines such as sheep and goats, porcines such as pigs, and bovines such as cattle and buffalo. Methods of obtaining transgenic animals are described in, for example, Puhler, A., Ed., Genetic Engineering of Animals, VCH Publ., 1993; Murphy and Carter, Eds., Transgenesis Techniques: Principles and Protocols (Methods in Molecular Biology, Vol. 18), 1993; and Pinkert, C A, Ed., Transgenic Animal Technology: A Laboratory Handbook, Academic Press, 1994. In certain embodiments, transgenic mice will be produced as described in Thomas et al. (1999) Immunol., 163:978-84; Kanakaraj et al. (1998) J. Exp. Med., 187:2073-9; or Yeh et al. (1997) Immunity 7:715-725. Methods of producing the transgenic animals are well-known in the art. See for example, Hooper, ML, Embryonal Stem Cells: Introducing Planned Changes into the Animal Germline (Modeem Genetics, v. 1), Int'. Pub. Distrib., Inc., 1993; Bradley et al. (1984) Nature, 309, 255-258; Jaenisch (1988) Science, 240:1468-1474; Wilmut et al. (1997) Nature, 385: 810-813; DeBoer et al., WO 91/08216; Wang, et al. Molecular Reproduction and Development (2002) 63:437-443); Page, et al. Transgenic Res (1995) 4(6):353-360; Lebkowski, et al. Mol Cell Biol (1988) 8(10):3988-3996; "Molecular Cloning: A Laboratory Manual. Second Edition" by Sambrook, et al. Cold Spring Harbor Laboratory: 1989; "Transgenic Animal Technology: A Laboratory Handbook," C. A. Pinkert, editor, Academic Press, 2002, 2nd edition, 618 pp.; "Mouse Genetics and Transgenics: A Practical Approach," I. J. Jackson and C. M. Abbott, editors, Oxford University Press, 2000, 299 pp.; "Transgenesis Techniques: Principles and Protocols," A. R. Clarke, editor, Humana Press, 2001, 351 pp.; Velander et al., Proc. Natl. Acad. Sci. USA 89:12003-12007, 1992; Hammer et al., Nature 315:680-683, 1985; Gordon et al., Science 214:1244-1246, 1981; and Hogan et al., Manipulating the Mouse Embryo: A Laboratory Manual (Cold Spring Harbor Laboratory, 2002), which are each incorporated herein by reference in their entirety.

Cells obtained from the transgenic non-human animals described herein may be obtained by taking a sample of a tissue of the animal. The cells may then be cultured. The cells preferably lack production of functional protein encoded by the nucleotide sequence comprising SEQ ID NO: 1-3 or a fragments or variants thereof.

In one embodiment, the transgenic non-human animal is a male non-human animal. In other preferred embodiments the transgenic non-human animal is a female non-human animal. According to other embodiments, the transgenic non-human animal oocyte, blastocyst, embryo, or offspring may be used as a model for a human disease, as a model to study human disease or to screen molecules, compounds and compositions. In certain embodiments, the cells of the transgenic oocyte, zygote, blastocyst, or embryo are used to establish embryonic stem (ES) cell lines. Stem cells are defined as cells that have extensive proliferation potential, differentiate into several cell lineages, and repopulate tissues upon transplantation. (Thomson, J. et al. 1995; Thomson, J. A. et al. 1998; Shamblott, M. et al. 1998; Williams, R. L. et al. 1988; Orkin, S. 1998; Reubinoff, B. E., et al. 2000).

Kits

The invention also provides kits useful in practicing the methods of the invention. In one embodiment, a kit of the invention includes a $Ca_v2$ channel modulator, e.g., contained in a suitable container. In a variation of this embodiment, the $Ca_v2$ channel modulator is formulated in a pharmaceutically acceptable carrier. The kit preferably includes instructions for administering the N-type calcium modulator to a subject to reduce or prevent a drug-related effect or behavior.

Instructions included in kits of the invention can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

EXAMPLES

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

Example 1

Described herein, according to certain embodiments, are compositions and methods related to the structural requirements and related mechanisms underlying G protein modulation of N-type $Ca^{2+}$ channels. $NH_3$ terminal elements function as a G protein-gated inhibitory module, acting via a previously unknown interaction with the I-II loop to produce channel inhibition. In one embodiment, when expressed as a free peptide with Gβγ, the $NH_3$ element constitutively inhibits channels. Beyond mechanism, the $NH_3$ terminal modulatory segment raises novel strategies to inhibit channels for biological and therapeutic ends.

Dominance of the $\alpha_{1B}$ $NH_3$ Terminus as a Structural Requirement for G Protein Inhibition In one embodiment, the functional impact of candidate structural determinants for the voltage-dependent G protein modulation of N-type $Ca^{2+}$ channels was examined. These elements reside on pore-forming $\alpha_1$ subunits (FIG. 1A, left) and include the I-II loop, the distal COOH tail, and the $NH_3$ terminus (NT). First, to impart strong G protein modulation, recombinant channels were coexpressed with G protein $\beta_1$ and $\gamma_2$ subunits (Gβγ) in HEK293 cells. This configuration gives a strong base-line against which to judge the effects of various deletions and chimeric-channel manipulations. Second, compound-state analysis (below) was used to provide a full biophysical description of modulation, thus minimizing chances that even subtle effects of channel manipulation would be missed. Third, a chimeric-channel screen pairing the most strongly modulated channel (N-type, $\alpha_{1B}$) with a partner completely insensitive to voltage-dependent G protein modulation (L-type, $\alpha_{1C}$) was emphasized. These features maximized resolution of the relative impact of various structural determinants.

FIGS. 1A and 1B summarize the baseline profile of N-type channel modulation, as viewed by compound-state analysis. Upon delivery of an isolated voltage step to 0 mV (FIG. 1A, gray voltage protocol without pre-pulse), $Ca^{2+}$ current activates almost entirely according to a slow exponential rise, characteristic of potent G protein modulation (FIG. 1B, gray current trace). This rising phase can be understood in terms of the "willing-reluctant" mechanism of G protein inhibition, shown at the extreme right of FIG. 1A (Bean, 1989). Here, "reluctant" channels (with Gβγ bound) are inhibited, and open poorly upon depolarization. However, channel affinity for Gβγ, while considerable when the channel re-sides in deep closed states, becomes weak to nonexistent as the channel nears the open state. Thus, upon moderate depolarization to 0 mV, many reluctant channels gradually shed their Gβγ (Zamponi and Snutch, 1998) and become "willing" channels that can readily open. This process underlies the progressive rise of current during the isolated voltage step (FIG. 1B, gray trace). Alternatively, application of a depolarizing pre-pulse (FIG. 1A, black voltage prepulse to +100 mV) rapidly forces reluctant channels toward their open conformation and completely dissociates Gβγ by the end of the prepulse (Colecraft et al., 2000). Hence, during the subsequent voltage step to 0 mV, the evoked current is initially large, being produced by a homogeneous population of willing channels (FIG. 1B, black current trace). However, at moderate depolarization to 0 mV, the aggregate affinity of Gβγ for reluctant channels increases (relative to prepulse), so a portion of willing channels will slowly reassociate with Gβγ (Zamponi and Snutch, 1998) and convert to the reluctant configuration. This conversion explains the subsequent decay of current (FIG. 1B, black current trace). Moreover, the convergence of gray and black current traces at 0 mV demonstrates a common, intermediate level of Gβγ binding at steady state. Using compound-state analysis, which approximates willing and reluctant configurations as two "compound" states (Agler et al., 2003; Neher and Steinbach, 1978), such current records specify two parameters that fully describe modulation at 0 mV: (1) the fraction of channels residing in the willing configuration at steady state [$W_{(00)}$~0.6] and (2) the time-constant with which this steady state is achieved (τ~60 ms). When protocols such as these are replicated at several potentials, W(f) and τ are specified as a function of voltage (FIG. 1B, right), providing a comprehensive modulatory "fingerprint." For orientation, Gβγ with G protein-insensitive L-type channels was coexpressed (FIG. 1F). These currents opened rapidly during depolarization to 0 mV and remained nearly unchanged by a prepulse; W(f) values approached unity throughout. N-type channels showed a similar profile absent Gβγ coexpression (compare FIGS. 1F and 3A).

From this baseline, substituting the I-II loop of the L-type channel $\alpha_{1C}$ subunit into the N-type channel $\alpha_{1B}$ backbone was considered (FIG. 1C, $\alpha_{1bBcBBBb}$). The I-II loop of $\alpha_{1B}$ (I-II$_B$) is a strong Gβγ binding locus, while the analogous loop of $\alpha_{1C}$ (I-II$_C$) reputedly fails to interact (De Waard et al., 1997; Qin et al., 1997) (see FIG. 15 below). Surprisingly, when coexpressed with Gβγ, the chimeric $\alpha_{1bBcBBBb}$ channel still exhibited obvious regulation (FIG. 1C, middle). Quantitatively, the loop substitution did weaken modulation (FIG. 1C, right), as W(f) was elevated (−100 to 0 mV), and r markedly accelerated. Nonetheless, I-II$_B$ initially presented more as a modulatory element, rather than as an indispensable determinant.

In R-type ($\alpha_{1E}$) channels, the distal COOH tail appeared functionally dominant over the I-II module, suggesting that a homologous COOH-tail module would also prove dominant in $\alpha_{1B}$ (Qin et al., 1997). Therefore the distal COOH tail of $\alpha_{1B}$ was deleted and substituted a YFP to compensate for the loss of mass (FIG. 1D, $\alpha_{1bBbBBBb\Delta\text{-}YFP}$). Currents exhibited robust modulation (FIG. 1D, middle), indistinguishable from that of wild-type channels (FIG. 1D, right). Simple truncation of the distal COOH tail of $\alpha_{1B}$ gave similar results (Supplemental Data, section 1). The COOH site played no detectable role in modulation of N-type channels.

Finally, for the third proposed determinant, the $NH_3$ terminus of $\alpha_{1B}$, the corresponding terminus of the G protein-insensitive L-type channel into the N-type ($\alpha_{1B}$) subunit was switched. The resulting $\alpha_{1cBbBBBb}$ channel completely lacked modulation (FIG. 1E), with W(f, V) hovering at unity throughout. These results confirmed the $NH_3$ terminus of $\alpha_{1B}$ as a predominant determinant of G protein modulation of N-type channels (Canti et al., 1999; Page et al., 1998).

Selective Interactions between the $NH_3$ Terminus and I-II Loop of $\alpha_{1B}$ To probe the dominance of the $\alpha_{1B}NH_3$ terminus ($NT_B$), binding among $NT_B$, $G\beta_1$, and other channel cytoplasmic domains, as analogous $NH_3$-terminal interactions impact gating in $K^+$ and CNG channels was tested (Minor et al., 2000; Sadja et al., 2003; Varnum and Zagotta, 1997; Zhou et al., 2001). As a sensitive initial screen, a yeast two-hybrid assay was used (McGee et al., 2004).

Before turning to novel interactions, a positive control was considered (FIG. 2A), confirming binding between $G\beta_1$ and the I-II loop of $\alpha_{1B}$ (I-II$_B$) (De Waard et al., 1997; Garcia et al., 1998; Li et al., 2004; Qin et al., 1997). Yeast cotransformation with two plasmids (one encoding $G\beta_1$ fused to GAL4 activation domain; the other for I-II$_B$ fused to GAL4 binding domain) yielded colonies on the "no-selection" plate. To test for binding, a filter lift of these colonies with subsequent screening for β-galactosidase expression was coupled, apparent as blue coloration in the "medium" assay panel. As a more stringent test of binding, replicated no-selection colonies onto "high" stringency media were plated, yielding enlarged and white-colored colonies indicating robust interaction. FIG. 2A (right) quantifies these results as the percentage (B, for "binding") of no-selection colonies that produced blue coloration in medium assays (gray) or thriving colonies under high stringency (black). Results were quantified over multiple trans-formations and averaged B values as shown. To exclude false positives, small background B values for $G\beta_1$ were confirmed (fused to activating domain) versus noninteracting lamin C (attached to binding domain). Likewise, limited backgrounds for I-II$_B$ (fused to binding domain) and the isolated activating domain itself were verified. Finally, the sum of these backgrounds was subtracted from the B value for $G\beta_1$/I-II$_B$ interaction, yielding net interaction (FIG. 2C, AB). The high AB percentage confirmed strong affiliation between these two molecules.

In a corresponding negative control, there was no interaction for GP, versus the proximal third of the L-type channel ($\alpha_{1C}$) COOH terminus (CTC) (FIGS. 2B and 2C). In particular, under high-stringency selection, colonies failed to expand, becoming pale disks (~stunted growth) with red foci indicative of adenine deficiency (Clontech-Laboratories, 1999).

Figure 1:
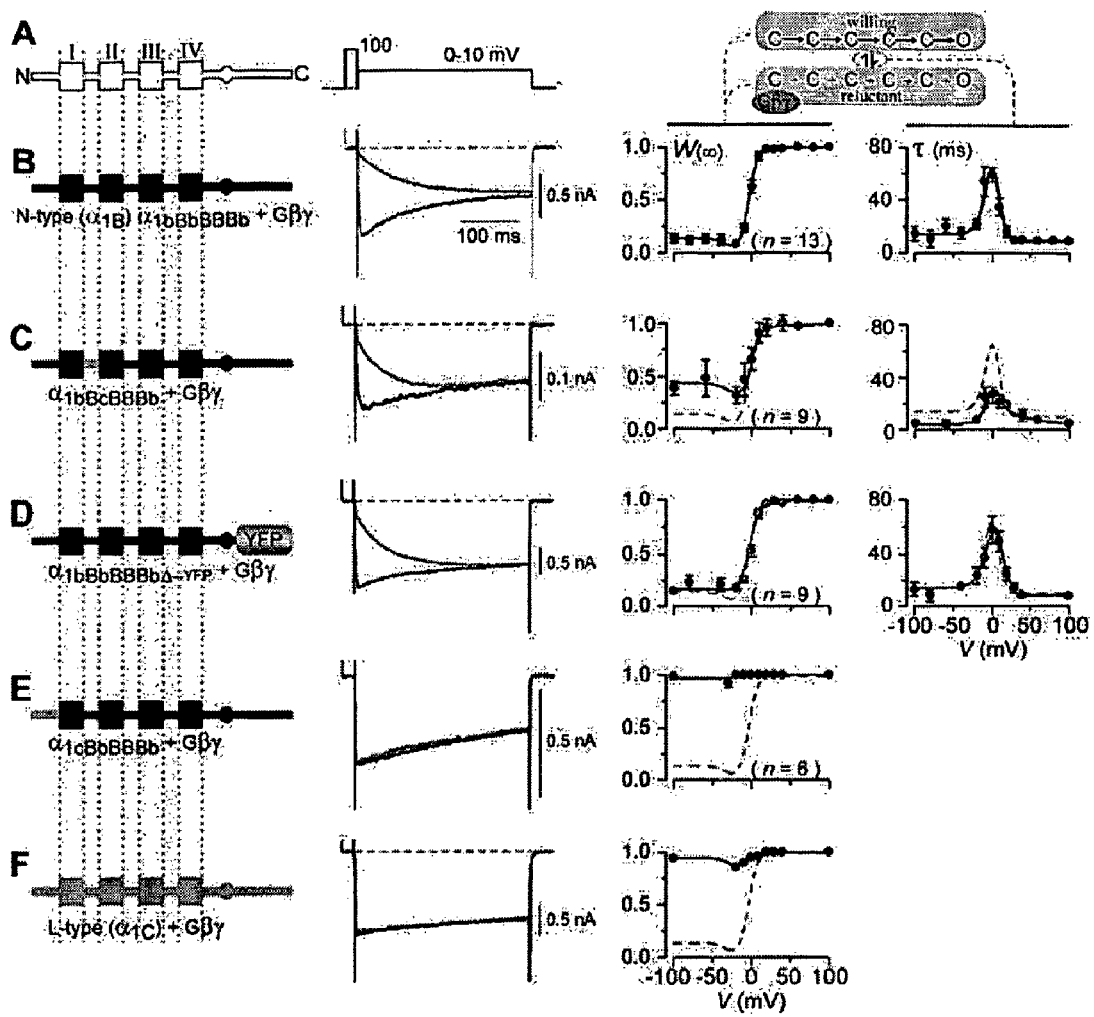
FIG. 1 shows structure-function analysis of G-protein modulation of N-type channels modulatory framework. (Left) $Ca^{2+}$ channel $α_1$. Homologous domains, I-IV. (Middle) Voltage protocol (±prepulse), holding potential=−100 mV throughout. Test pulse, 0 mV for traces, unless noted. (Right) "Willing-reluctant" model. N-type channels, with Gβγ. (Left) $α_{1B}$ aligned to generic $α_1$ (A). (Middle) Exemplar currents (gray, -prepulse; black, +prepulse). Extreme outward/inward currents were clipped throughout for clarity. (Right) Compound-state analysis, number of cells in parentheses, from Agler et al. (2003). Chimeric channel replacing I-II loop of $α_{1B}$, with that of $α_{1C}$. Format as above (A). Nomenclature: homologous domains denoted by capital letters referencing parent channel (B for $α_{1B}$, C for $α_{1C}$); relevant cytoplasmic domains (NT, I-II, and COOH terminus) specified by lower-case letters (b for $α_{1B}$). Currents with 20 mM $Ba^{2+}$, traces at 10 mV to correct surface-potential shift. Dashed lines, control fits (A), throughout figure. $α_{1B}$ with C tail truncation (at residue 1877) and fusion to YFP. Format as above (A). Chimeric channel replacing N terminus of $α_{1B}$ with that of $α_{1C}$. Format as above (A), except 20 mM $Ba^{2+}$ and test depolarization to 10 mV. W(f,V)~1, so τ(V) is indeterminate. L-type channel (G protein insensitive) with Gβγ. Format as above (A). (C-E) Specific composition/construction of channels, see Supplemental Data (section 1).

Given these controls, $G\beta_1$ interactions with $NT_B$ and other channel segments were screened (FIG. 2C). There was no indication of $G\beta_1$ binding to the proximal COOH terminus of the P/Q-type channel ($\beta_{1A}$) subunit ($CT_A$). Beyond this result, however, $G\beta_1$ binding appeared widespread. Not only did $G\beta_1$ interact with $NT_B$, but also with the corresponding $NH_3$ termini of L-type ($\alpha_{1C}$) and P/Q-type ($\alpha_{1A}$) subunits, respectively labeled $NT_C$ and $NT_A$. The results with $NT_A$ and $NT_B$ are novel. As residues 1-55 of $NT_B$ may be a strong modulatory determinant (Page et al., 1998), it was notable that this segment also interacted with $G\beta_1$ (FIG. 2C, $NT_B$ [1-55]). While isolated yeast results must be cautiously interpreted, there was no clear evidence that selective GPI binding to $NT_B$ could explain its unique function (FIG. 1).

Instead, considering the impact on gating of I-II loop associations with other cytoplasmic domains of L-type channels (Kim et al., 2004), preferential interaction between $NT_B$ and I-II$_B$ as an underlying basis for G protein modulation were tested (FIG. 2D). In fact, yeast two-hybrid assays were positive for the $NT_B$/I-II$_B$ pair. Intriguingly, testing $NT_B$ against I-II$_C$ failed to reveal an association, as did the pairing of $NT_C$ with either I-II$_B$ or I-II$_C$. Thus, a preferential affiliation between $NT_B$ and I-II$_B$ could explain the singular functional requirement for $NT_B$.

To confirm preferential interaction of $NT_B$ with I-II$_B$ a live-cell FRET two-hybrid assay was used (Erickson et al., 2003), in which $NT_B$, $NT_C$, I-II$_B$, and I-II$_C$ were fused to either CFP or YFP, and the resulting fusion constructs expressed pair-wise in mammalian HEK293 cells. Given a Forster distance of ~50 Å for the CFP/YFP pair (Patterson et al., 2000), the presence of FRET in individual cells would give a strong indication of interpeptide binding in the mammalian intracellular milieu. This indication is generally characterized by a low false-positive rate (Erickson et al., 2003), so that FRET assays provide a useful complement to yeast two-hybrid assays (Allen et al., 1995). Additionally, the degree of FRET interaction depends upon the fractional binding between interacting peptides; hence, variability in the expression levels of fusion constructs among cells could be exploited to estimate a relative dissociation constant ($K_{d,EFF}$) that gauges binding affinity. For example, FIG. 2Ea shows a cell expressing $NT_B$-CFP and I-II$_B$-YFP, here viewed through three filter cubes. $S_{CFP}$ (the signal derived from an image obtained with the CFP filter cube) is selective for CFP fluorescence and thereby gives an optical measure of $NT_B$-CFP expression. Analogously, the $S_{YFP}$ signal, derived from preferential excitation and detection of YFP, estimates I-II$_B$-YFP levels. Finally, the $S_{FRET}$ signal reflects I-II$_B$-YFP fluorescence stimulated by FRET transfer from $NT_B$-CFP, as well as secondary cross-talk signals. These three signals can be incorporated within a three-cube FRET algorithm to determine the strength of FRET interaction ("FRET ratio," FR), independently of cross-talk (Erickson et al., 2001). FR adopts a value of unity in the absence of FRET and grows linearly with increasing FRET efficiency (Erickson et al., 2003). FR values for many individual cells are plotted as circles in FIG. 2Eb, with numerous determinations clearly greater than unity. Alternatively, FR values specified by a YFP-photobleaching methodology were also elevated above unity (triangles) (Bastiaens and Jovin, 1996). More rigorously, when variable expression levels of $NT_B$-CFP ($D_{free}$, free relative donor concentration) or I-II$_B$-YFP ($A_{free}$, free relative acceptor concentration) were taken into account, the FR data conformed to a 1:1 binding relation (solid curve), with a $K_{d,EFF}$ (FIG. 2Ef) comparable to that for an apoCaM/IQ segment interaction supporting inactivation of L-type channels (Erickson et al., 2003). By contrast, for the FRET pairs $NT_B$/I-II$_C$, $NT_C$/I-II$_B$, and $NT_C$/I-II$_C$ (FIGS. 2Ec, 2Ed, 2Ee), $K_{d,EFF}$ values were all larger by an order of magnitude or more (FIG. 2Ef). Consistent with yeast two-hybrid assays, then, FRET assays confirmed a selective propensity for $NT_B$ and I-II$_B$ segments to associate.

$NH_3$ Terminus of $\alpha_{1B}$ Produces G Protein-Gated Channel Inhibition

If a unique interaction between $NT_B$ and I-II$_B$ was necessary for G protein inhibition of N-type channels, a sufficiently high concentration of free $NT_B$ peptide should usurp the I-II$_B$ binding site and perturb the normal modulatory profile. Currents might be inhibited in a manner where prepulse depolarization fails to reverse inhibition (FIG. 1). Without the latter signature of G protein inhibition, a requirement for detecting such an effect would be the means to distinguish changes in channel open probability, apart from nonspecific changes in channel expression.

FIG. 3A illustrates an approach for N-type channels without $G\beta\gamma$ coexpression. Exemplar currents activated quickly and were barely facilitated by strong prepulse depolarization (FIG. 3A, left). The slight residual prepulse facilitation reflects basal endogenous $G\beta\gamma$ activation. To estimate open probability, two intermediary parameters were specified. First, to gauge the number of channels in a cell ($N_{channel}$), the channel gating current at the reversal potential for ionic current were isolated (FIG. 3A, middle left) (Jones et al., 1999).

The area under this current yields the maximal gating charge $Q_{max}$, where $Q_{max}=N_{channel} \times q_{max}$, and $q_{max}$ is the maximal gating charge per channel. Second, $G_{max}$ for a given cell, the maximal ionic current conductance determined as the slope of the peak current-voltage relation at depolarized potentials were determined (FIG. 3A, middle right, line). Here and throughout, current-voltage relations were determined after a 100 mV prepulse, which transiently relieves all G protein inhibition (Colecraft et al., 2000), thus eliminating these inhibitory effects in the estimate of $G_{max}$. Accordingly, $G_{max}=N_{channel} \times P_{o,max} \times g$, where $P_{o,max}$ is the maximal channel open probability at saturating de-polarization, and g is the conductance of a single open channel. In combination, then, a plot of $G_{max}$ versus $Q_{max}$ for multiple cells (FIG. 2A, right) would describe a linear relation with slope equal to $P_{o,max} \times g/q_{max}$. Because g and $q_{max}$ are unchanged by G protein modulation (Colecraft et al., 2001; Jones et al., 1997; Patil et al., 1996), this slope (G/Q=0.44±0.03 nS/fC) is proportional to $P_{o,max}$ . . . FIG. 3B documents the supporting results for N-type channels coexpressed with Gβγ. $G_{max}$ determined after prepulse de-polarization, when plotted against $Q_{max}$, specifies an identical slope to that without Gβγ (FIG. 3B, right, G/Q=0.43±0.04 nS/fC). Hence, prepulse depolarization normally relieves G protein inhibition in this system. Free $NT_B$ peptide with $α_{1B}$ channels. Initially, an $NT_B$-CFP peptide was employed to visually confirm expression was coexpressed. Absent Gβγ, no differences from control were observed (compare FIGS. 3C and 3A). By contrast, coexpressing channels with $NT_B$-CFP and Gβγ produced remarkable effects (FIG. 3D). Currents showed little slowing of activation, and prepulse facilitation was diminished (FIG. 3D, left). More telling were small ionic current amplitudes despite gating current magnitudes on par with controls (FIG. 3D, middle panels). Consequently, there was a significant $^{~}$6-fold depression of the $G_{max}$-$Q_{max}$ plot (FIG. 3D, right). If $NT_B$-CFP were simply chelating Gβγ (FIG. 2C), the G/Q slope would be unchanged from control. Instead, the suppression of G/Q indicates constitutive inhibition of channel opening.

To establish specificity, several variants of this initial result were considered. First, channels with free $NT_B$ peptide itself (without CFP fusion) and Gβγ (FIG. 4A) were coexpressed. The results were identical to those obtained with $NT_B$-CFP, demonstrating that the active ingredient was $NT_B$ alone. Second, channels with free peptide for the $NH_3$ terminus of $α_{1C}$ ($NT_C$) were coexpressed. Both in the absence and presence of Gβγ, free $NT_C$ peptide had no effect (FIGS. 4B and 4C). Constitutive inhibition appeared specific to the $NT_B$ segment.

Figure 4:
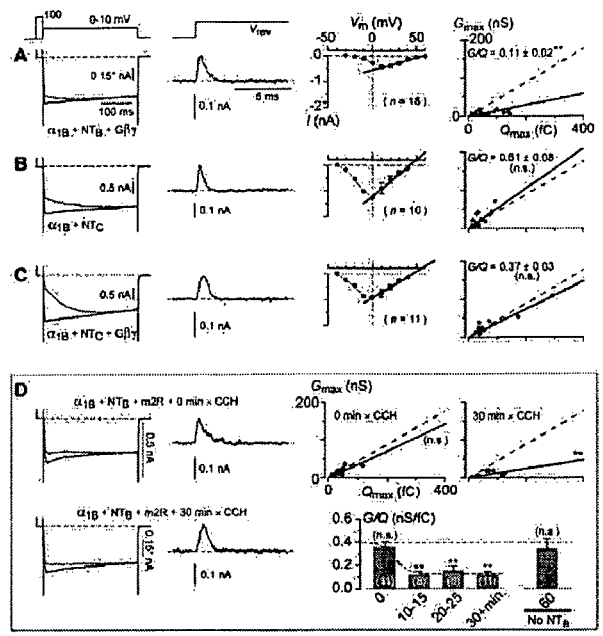
FIG. 4 shows the selectivity of α$_{1B}$ NH$_3$-terminal peptide effects. (A-C) G/Q analysis for various channels, peptides, and Gβγ. Format as in FIG. 3. (A) G/Q analysis, N-type channels, with NT$_B$ and Gβγ, same G/Q suppression as FIG. 3D. (B and C) NH$_3$-terminus of α$_{1C}$ does not affect G/Q, Gβγ. (D) G/Q analysis, N-type channels with both NT$_B$ and m2R receptor. (Left half) Ionic and gating currents, obtained without m2R activation by carbachol (top, 0 min×CCH), and with m2R activation by 30-min×50 μM CCH (bottom). Separate cells. Format as above (A-C). (Right half) Top, G$_{max}$-Q$_{max}$ plots without CCH exposure, and after 30 min application of CCH, 0 min×CCH plot, squares represent channels coexpressed with m2R, but without NT$_B$; circles refer to channels coexpressed with m2R and NT$_B$. (Right half, bottom) Average G/Q slope parameters for plots above, and for intermediary CCH exposures (labeled on the bottom). Composition of m2R and segments.

Finally, whether the constitutive inhibition produced by free $NT_B$ was a nonspecific effect related to prolonged 24-48 hr overexpression of Gβγ was explored. Accordingly, coexpression of free $NT_B$ during receptor activation of G proteins were examined, using a recombinant m2 muscarinic receptor engineered to minimize desensitization (m2R) (Pals-Rylaarsdam and Hosey, 1997). Bath application of carbachol (CCH) rapidly induced marked G protein modulation of channels (Cole-craft et al., 2000; Patil et al., 1996), lasting over an hour (Supplemental Data, section 4). Absent carbachol, coexpression of channels and m2R (±$NT_B$ peptide) produced functional profiles indistinguishable from control N-type channels (FIG. 4D, upper row, 0 min×CCH). By contrast, with m2R and free $NT_B$ peptide present, application of carbachol for ≧30 min produced constitutive inhibition, as illustrated by traces showing little prepulse facilitation, small ionic current amplitude, and maintained gating current size (FIG. 4D, bottom left). Population data corroborated these trends, showing marked suppression of the G/Q slope (FIG. 4D, top right, 30 min×CCH). Without $NT_B$ peptide, carbachol application for 60 min produced no G/Q depression (FIG. 4E, bottom), excluding nonspecific actions of carbachol. Moreover, the detailed induction time course (FIG. 4E, bottom) indicates that the free $NT_B$ peptide acted within 10-15 min of receptor activation. Given that the receptor-mediated $NT_B$ effect was best produced in the incubator at 37° C., rather than at the room temperature used for patch-clamp recording, the 10-15 min induction may well reflect the duration required for free $NT_B$ to penetrate and associate appropriately with a channel, once rendered permissive for interaction by Gβγ. Overall, multiple approaches (FIG. 4) made it unlikely that the constitutive inhibition produced by free $NT_B$ peptide reflects unintended effects.

Figure 2:
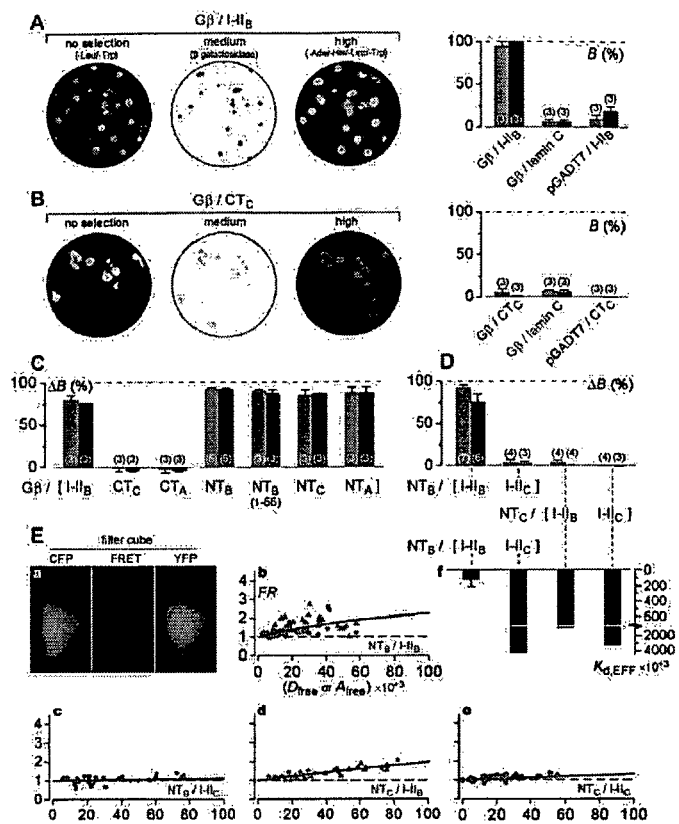
FIG. 2 demonstrates the yeast and FRET two-hybrid assays of binding among channel segments and Gβγ. Yeast, positive control, Gβ₁ (pGADT7), I-II$_B$ (pGBKT7). No selection, growth on -Leu/-Trp plates. Medium, filter-lift assay of "no selection" plate; blue-colored colonies indicate interaction. High, replication of "no selection" colonies onto high-stringency plates (-Ade/-His/-Leu/-Trp). (Right) Percent colonies (B) turning blue (gray) or surviving under high stringency (black). Bars shown as mean±SEM, with number of transformations in parentheses throughout. Yeast, negative control, Gβ$_1$ (pGADT7), CT$_C$ (pGBKT7). Format as above (A). Yeast, Gβ$_1$ (pGADT7), channel fragments (pGBKT7). AB, background-subtracted binding percentages, shown as mean±SEM. Yeast, NT$_B$ (pGBKT7) versus I-II loops of β$_{1B}$ and α$_{1C}$ (I-II$_B$ and I-II$_C$, pGADT7); NTC (pGBKT7) versus I-IIB and I-IIC (pGADT7). Format as above (C). (A-D) Background levels, segment composition, see Supplemental Data (section 2). FRET assays, NT$_B$ versus I-II$_B$ and I-II$_C$, and NT$_C$ versus I-II$_B$ and I-II$_C$. (Ea) Widefield fluorescence images of cell coexpressing NT$_B$-CFP and I-II$_B$-YFP, viewed with CFP, FRET, and YFP filters. (Eb-Ee) FR versus relative concentration of binding partners. For three-cube FRET, FR for each cell (circle) versus relative free donor (CFP-tagged molecule) concentration, D$_{free}$. For YFP-photobleaching, FR for each cell (triangle) versus the relative free acceptor (YFP-tagged molecule) concentration. Smooth curves, simultaneous fits to three-cube FRET and donordequenching data; parameters in (Ef). Pairings, NT$_B$-CFP versus I-II$_B$-YFP (Eb), NT$_B$-CFP versus I-II$_B$-YFP (Ec), NT$_C$-CFP versus I-II$_B$-YFP (Ed), and NT$_C$-YFP versus I-IIC-CFP (Ee). Rise of FR in (Ed) occurs primarily at larger D$_{free}$ or A$_{free}$, indicative of low-affinity interaction (large K$_{d,EFF}$ in [Ef], ≅8-fold larger than NT$_B$/I-II$_B$), with high FR$_{max}$ (approximate large FRET when NT$_C$/I-II$_B$ partners manage to bind). Segment composition, see Supplemental Data (section 2). (Ef) K$_{d,EFF}$ for pairings in (Eb)-Ee). Standard errors by Jacobian error matrix analysis; means without bars, lower-limit estimates. FR$_{max}$, 3.66 for NT$_B$-CFP/I-II$_B$-YFP, and 10.8 for others.
Figure 5:
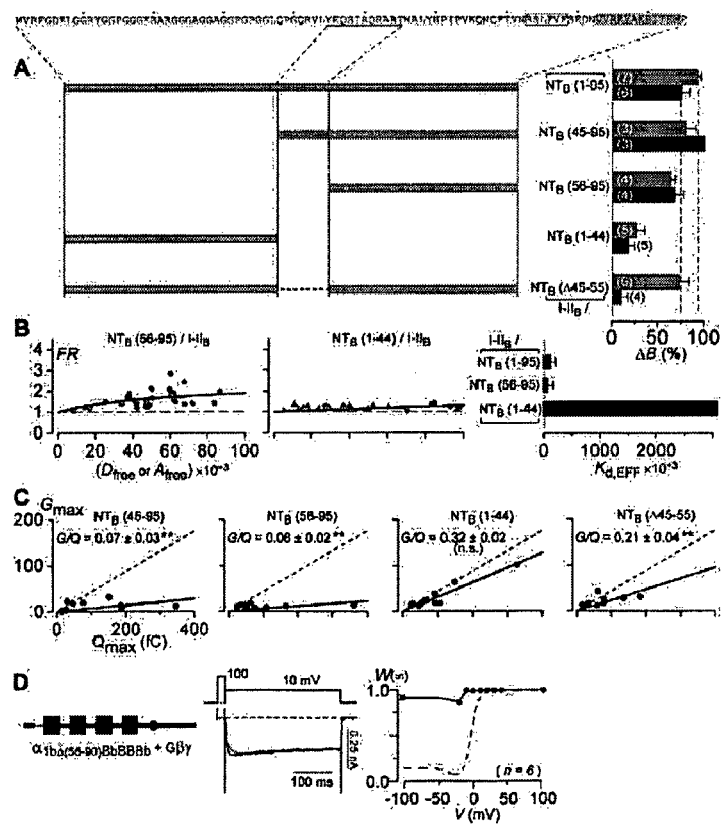
FIG. 5 demonstrates that channel modulation correlates with NT$_B$ binding to the I-II loop of α$_{1B}$. (A) Yeast mapping, NT$_B$ sub-domains, I-II$_B$ loop. Top, NT$_B$ sequence. PhD analysis: shaded region, helical; boxed region, strand. Underline, modulatory hotspot (Canti et al., 1999). Below, left, NT$_B$ sub-regions (pGBKT7) paired with I-II$_B$ (pGADT7) in yeast assays. Below, right, ΔB, format as in FIG. 2D. NT$_B$ (1-95) reproduced from FIG. 2C for reference. NT$_B$ (56-95) suffices for full interaction. (B) FRET assays, NT$_B$ (56-95)—CFP with I-II$_B$-YFP, and NT$_B$ (1-44)-CFP with I-II$_B$-YFP. Left and middle, binding-curve analysis, format as in FIG. 2Ee. Right, relative dissociation constants for curves on left; format as in FIG. 2Ef. For reference, data for NT$_B$ (1-95) interaction reproduced from FIG. 2Ef. FR$_{max}$ values: 2.44 for NT$_B$ (56-95)—CFP versus I-II$_B$-YFP; 10.8 for NT$_B$ (1-44)-CFP versus I-II$_B$-YFP. (C) G/Q slope depression correlates with NT$_B$ subdomain interaction with I-II$_B$. Format as in FIG. 4A. Dashed lines, control fit (FIG. 3A). For NT$_B$ (45-95) and NT$_B$ (56-95), obtained with 20 mM Ba$^{2+}$, G$_{max}$ converted to 2 mM Ca$^{2+}$ equivalents. Other data, 2 mM Ca$^{2+}$. Ancillary data, Supplementary Data (section 5). (D) Deletion of core NT$_B$ residues (α$_{1B(\Delta 56-90)BbBBBb}$) eliminates 2+G protein modulation. Format as in FIG. 1E, step to 10 mV and 20 mM Ba$^{2+}$.

Inhibitory Potential of $NT_B$ Correlates with its Ability to Interact with the I-$II_B$ It was further investigated whether $NT_B$ peptide inhibition was causally related to $NT_B$/I-$II_B$ interaction, as initially proposed (FIG. 2). Therefore, $NT_B$ was dissected for subregions capable of I-$II_B$ binding and then investigated the ability of these subfragments to constitutively inhibit channels. Initial mapping was performed with yeast two-hybrid assays (FIG. 5A). Because the first 44 residues of the N-type channel $α_{1B}$ subunit can be deleted without affecting G protein modulation (Canti et al., 1999), it was tested whether $NT_B$ (45-95) could by itself interact with I-$II_B$. Robust ΔB values confirmed this expectation. Given that deletion of residues 45-55 from $α_{1B}$ subunits sharply attenuates G protein inhibition (Canti et al., 1999), next examined was whether $NT_B$ (56-95) would fail to associate with I-$II_B$. Contrary to this supposition, the $NT_B$ (56-95) peptide seemed fully capable of such binding. To further establish that most of the interaction region is confined to residues 56-95, explicitly tested was $NT_B$ (1-44) for binding to I-$II_B$. Fitting with the primacy of residues 56-95, $NT_B$ (1-44) showed little interaction. Finally, to explore the elimination of G protein modulation by deleting residues 45-55 in $α_{1B}$ (Canti et al., 1999), paired were I-$II_B$ with an $NT_B$ peptide lacking residues 45-55, $NT_B$ (Δ45-55). The data suggest partially attenuated association of $NT_B$ (Δ45-55) with I-$II_B$. Thus, $NT_B$ (56-95) contains the main I-$II_B$ interaction locus. Amino acids 45-55 may restrain residues 144 from interfering with the binding potential of residues 56-95, as seen with full-length $NT_B$.

To confirm that $NT_B$ (56-95) suffices to support strong affiliation with I-$II_B$, paired were $NT_B$ (56-95)—CFP with I-$II_B$-YFP in FRET experiments (FIG. 5B). The data conformed to a 1:1 binding curve (left), with an affinity equivalent to that of full $NT_B$ (right). Conversely, $NT_B$ (1-44)—CFP showed no detectable association with I-$II_B$-YFP (middle and right). Therefore, residues 56-95 incorporate the dominant locus of $NT_B$ binding to I-$II_B$.

Having established the propensity of various $NT_B$ fragments to associate with I-$II_B$, this propensity was correlated with the ability to constitutively inhibit channels (FIG. 5C). With Gβγ present, $NT_B$ (45-95) and $NT_B$ (56-95) both depressed $G_{max}$-$Q_{max}$ relations to the same extent as did full $NT_B$ (FIG. 4A). By contrast, $NT_B$ (144) kept corresponding relations essentially unchanged from control, while $NT_B$ (Δ45-55) exerted inter-mediate inhibition. Throughout, the proclivity for I-$II_B$ affiliation matched the degree of channel inhibition (Supplemental Data, section 5.2). Not only does the $NT_B$ domain function as a G protein-gated inhibitory module, the inhibitory potential of $NT_B$ seems closely related to its ability to interact with I-$II_B$.

Role of $NT_B$ Inhibitory Module in G Protein Modulation of the Holo N-Type Channel To probe the possibility that the effect of free $NT_B$ peptide was unrelated to the actual modulatory mechanism within intact holo-channels, an $\alpha_{1B}$ subunit was constructed lacking essentially all of the $NT_B$ locus required to bind I-II$_B$ (FIG. 5D, left, $\alpha_{1B\Delta(56-90)BbBBBb}$). Exemplar currents (FIG. 5D, middle) and population data (FIG. 5D, right) documented complete ablation of modulation. Thus, the $NT_B$ inhibitory module may be central to the voltage-dependent G protein inhibition of N-type Ca$^{2+}$ channels.

The NH$_3$ terminus of the N-type Ca$^{2+}$ channel $\alpha_{1B}$ subunit ($NT_B$) were confirmed as a predominant structural determinant of voltage-dependent G protein modulation of these channels (Canti et al., 1999; Page et al., 1998).

Revised Mechanism for G Protein Modulation of N-Type Ca$^{2+}$ Channels

Recognition of a G protein-gated inhibitory module ($NT_B$) motivates initial mapping of structural events onto the largely kinetic format of the "willing-reluctant" mechanism for G protein modulation (FIG. 1A). In the current view, G$\beta\gamma$ partitions channels between "willing" (G$\beta\gamma$ unbound) and "reluctant" (G$\beta\gamma$ bound) pools (Bo-land and Bean, 1993). Willing channels open readily upon depolarization ($\Delta V$), while reluctant channels open poorly. Because $NT_B$/I-II$_B$ binding correlates with constitutive inhibition (FIG. 5), but only with G$\beta\gamma$ present (FIGS. 3C, 3D, and 4D), $NT_B$ and I-II$_B$ elements are portrayed as noninteracting in willing channels (FIG. 6A, top). Though peptide versions of these segments can interact without G$\beta\gamma$ (FIGS. 2 and 5), it could be envisages that the corresponding elements in holo-channels require G$\beta\gamma$. For instance, without G$\beta\gamma$, the I-II$_B$ within a channel may be inaccessible for $NT_B$ interaction. Extending this reasoning to reluctant channels, G$\beta\gamma$/channel binding would permit $NT_B$/I-II$_B$ interaction (FIG. 6A, bottom left), which is fundamental to this gating mode. Specifically, the results with free $NT_B$ peptide (FIGS. 3D, 4A, 4D, and 5C) and with the $\beta_{1B\Delta(56-90)BbBBBb}$ channel (FIG. 5D) imply that it is $NT_B$/I-II$_B$ association within a holo-channel that inhibits opening. Moreover, the constitutive (i.e., prepulse insensitive) nature of $NT_B$ peptide inhibition (FIGS. 3D, 4A, 4D, and 5C) hints at a mechanism for depolarization-induced relief of inhibition, seen during conventional modulation. Normally, depolarization may drive reluctant channels into states favoring G$\beta\gamma$ unbinding (FIG. 6A, bottom right), with consequent reversal of inhibition (Boland and Bean, 1993). Free $NT_B$ peptide lacks covalent linkage to the channel, so it is plausible that this linkage normally conveys voltage-induced contortion to the $NT_B$/I-II$_B$ interaction (FIG. 6A, bottom right), which then destabilizes G$\beta\gamma$ binding. Thus, $NT_B$/I-II$_B$ interaction may not only be key for inhibition, but destabilization of this interaction may also underlie voltage-dependent relief of inhibition.

Consideration of channel inhibition by free $NT_B$ yields a deeper perspective (FIG. 6B). Upon G$\beta\gamma$ activation, free $NT_B$ outcompetes the intrinsic $NT_B$ module for access to the I-II$_B$ loop (FIG. 6B, bottom left), partly owing to overexpression of peptide and a mass-action effect. Based on the inhibition by free $NT_B$ (FIGS. 3 and 4), this affiliation of channel I-II$_B$ and free $NT_B$ likely suffices to restrict opening. Without covalent linkage between the channel and free $NT_B$, however, depolarization would not contort the association of I-II$_B$ and $NT_B$ peptide (FIG. 6B, bottom right) and spare G$\beta\gamma$ binding. Channels would thus be "constitutively reluctant" (FIG. 6B, bottom). Such a scenario raises two points. (1) Compared to reluctant channels, the lack of depolarization-mediated G$\beta\gamma$ unbinding in constitutively reluctant channels would decrease the overall G$\beta\gamma$ unbinding rate. Consequently, with G$\beta\gamma$ present, the steady-state binding of channel I-II$_B$ to $NT_B$ peptide would be enhanced beyond that produced by the mass-action effect raised above. (2) As predicted, following induction of constitutive inhibition by $NT_B$ peptide and carbachol (c.f. FIG. 4D), removal of carbachol (for >3 min) did not reverse inhibition (data not shown), as if G$\beta\gamma$ remained bound after dissipation of free G$\beta\gamma$.

Integration of Experimental Perspectives on G Protein Inhibition

Figure 6:
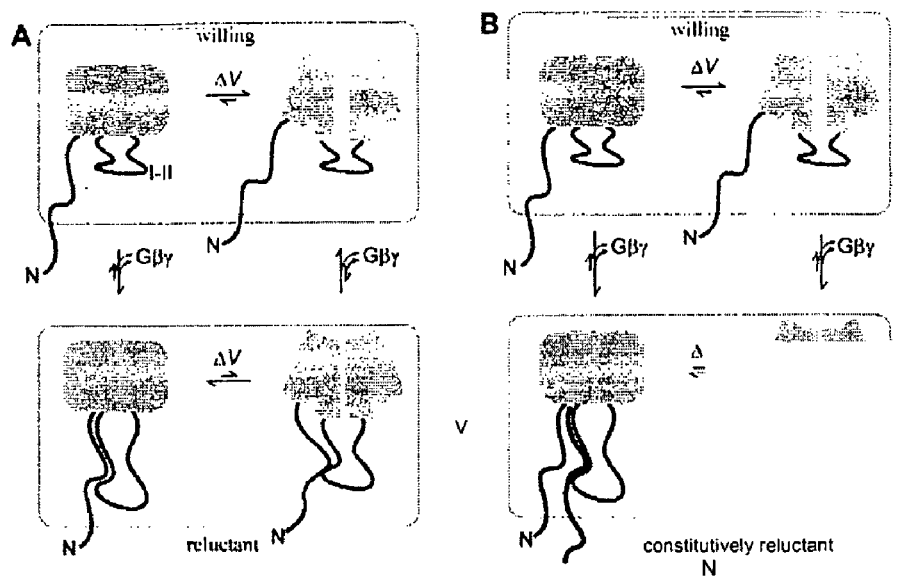
FIG. 6 shows the revised mechanism of G protein modulation of N-type Ca$^{2+}$ channels. (A) Willing-reluctant model, including potential NT$_B$/I-II$_B$ inhibitory interactions. (Top) Willing mode, depolarization (ΔV), Gβγ absent, NT$_B$ and I-II$_B$ separate. (Bottom) Reluctant mode, Gβγ bound to channel, NT$_B$ and I-II$_B$ interact and inhibit opening. Depolarization contorts NT$_B$/I-II$_B$ interaction, promoting Gβγ release. (B) Model of constitutive inhibition by NT$_B$ peptide. (Top) Willing channel nonpermissive for I-II$_B$ interaction with either native NT$_B$ or free NT$_B$. (Bottom) Constitutively reluctant channel, where NT$_B$ peptide (thick black segment) usurps I-II$_B$ from native NT$_B$, an event that inhibits channel opening. Without covalent linkage of NT$_B$ peptide to channel, depolarization fails to contort NT$_B$/I-II$_B$ interaction, and Gβγ remains bound.

In reference to FIG. 6, in certain aspects, $NT_B$ may support another functional role, given that outside the $NT_B$ (56-95) core required for I-II$_B$ interaction, deletions of $\alpha_{1B}$ residues 1-55 or 45-55 both eliminate G protein modulation (Canti et al., 1999; Page et al., 1998), as replicated (data not shown). Based on the interaction of $NT_B$ with G$\beta\gamma$ (FIG. 2C), it is suggested that the initial residues of $NT_B$ may contribute to an aggregate G$\beta\gamma$ binding pocket on the channel [$NT_B$ (1-55)], much as both NH$_3$ and COOH termini of GIRK channels jointly coordinate G$\beta\gamma$ binding (Sadja et al., 2003; Zhou et al., 2001). Thus, $NT_B$ may incorporate two actions: possibly helping to bind G$\beta\gamma$ as an initiatory event, followed by I-II$_B$ loop interaction leading to channel inhibition. Because constitutive inhibition would be unexpected for N-terminal channel segments that only contribute to G$\beta\gamma$ binding (but not I-II$_B$ linker interaction), our G/Q screen (FIG. 5C) is consistent with such bifunctionality of $NT_B$.

The new data here favor $NT_B$/I-II$_B$ binding as central to channel inhibition (FIGS. 3-5) and thus support the essentiality of both I-II$_B$ and $NT_B$ modules. This viewpoint warrants two points. (1) G protein modulation of N-type channels was strongly attenuated by application of 1-II$_B$ subdomain peptides, without notable change in overall current amplitude (Zamponi et al., 1997). Such attenuation was attributed to peptide chelation of G$\beta\gamma$, thus projecting G$\beta\gamma$/I-II$_B$ binding as essential for channel modulation. FIG. 6 raises the possibility that this attenuation may also reflect I-II$_B$ peptide chelation of the native $NT_B$ segment attached to N-type channels, so as to produce "constitutively willing" channels. Indeed, the $NT_B$ peptide interacts with the N-terminal third of the I-II$_B$ loop in a region that contains two of three peptides found to inhibit N-type channel modulation by G$\beta\gamma$ (Zamponi et al., 1997). Still, another result does suggest that G$\beta\gamma$/I-II$_B$ binding is central for G protein modulation: a T422E mutation within I-II$_B$ selectively impacts modulation by GP, but not other G$\beta$ subtypes (Doering et al., 2004). On balance, then, the I-II$_B$ element seems important for G protein inhibition, not only via $NT_B$ interactions, but also by contributing to functionally relevant association with G$\beta\gamma$. (2) The persistence of G protein modulation in chimeric $\alpha_{1BcBBBb}$ channels (FIG. 1C) might initially appear to contradict the importance of the I-II$_B$ loop (Canti et al., 1999; Zhang et al., 1996). However, both I-II$_C$ and I-II$_B$ loops could support an obligatory G protein modulatory function, though overt signs of such a I-II$_C$ capability may remain hidden in L-type ($\alpha_{1C}$) channels lacking additional elements like $NT_B$. In fact, hybridization assays suggest G$\beta\gamma$ interaction with the I-II$_C$ element. Hence, the modest modulation of $\beta_{1BBcBBBb}$ channels (FIG. 1C) could reflect bona fide G$\beta\gamma$/I-II$_C$ interaction, whose modulatory output is muted by weak $NT_B$/I-II$_C$ interaction (compared to $NT_B$/I-II$_B$). This weakened interaction is directionally consistent with hybridization assays for $NT_B$/I-II$_C$ (FIGS. 1D and 1E and F), if one considers the intramolecular context of presumed $NT_B$/I-II$_C$ binding within chimeric channels (Page and Jencks, 1971).

Finally, complete preservation of modulation upon deletion of the COOH site (FIG. 1D) excludes an obligatory role in voltage-dependent G protein modulation of N-type channels (Qin et al., 1997). This site may help attract G$\beta\gamma$ and adjust submaximal responses (Hamid et al., 1999; Li et al., 2004), but for core mechanism, the COOH site is not considered in FIG. 6.

Detecting Constitutive Inhibition of Channels

Figure 7:
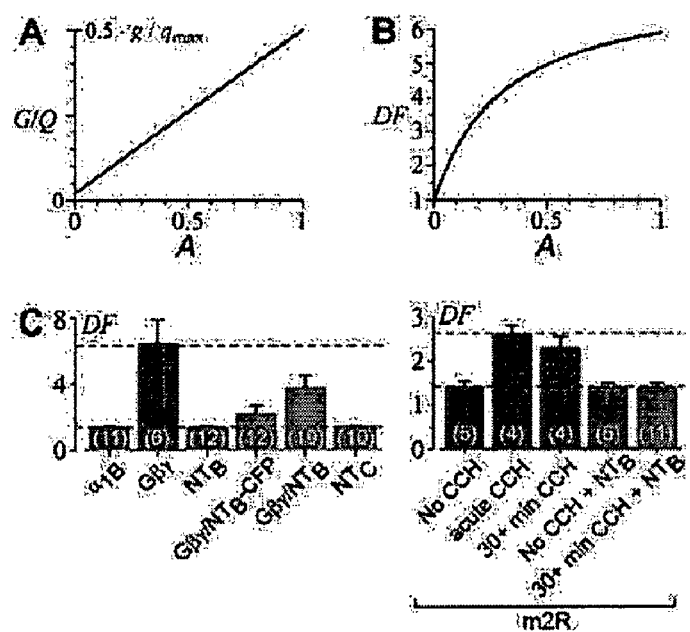
FIG. 7 demonstrates detecting constitutive inhibition of channels. (A) Predicted relationship between G/Q slope (nS/fC) and fraction of channels residing outside constitutively reluctant mode (parameter A) (Supplemental Data, section 7, Equation 1). (B) Predicted relationship between DF and parameter A (Supple-mental Data, section 7, Equation 2). (C) DF values for FIGS. 3 and 4 (A-C) (left) and FIG. 4D (right).

The G/Q slope parameter used here is appropriate, because G/Q slope will decline in approximately direct proportion to decreasing A (FIG. 7A), where A is the fraction of willing versus constitutively reluctant channels after prepulse depolarization. By contrast, the degree of prepulse facilitation (DF), a commonly used measure of G protein modulation, proves problematic for assessing constitutive inhibition. DF is the ratio of currents measured milliseconds after step depolarization to 0-10 mV, as evoked plus or minus prepulse. Accordingly, DF equals unity without Gβγ and grows progressively with increasing Gβγ. Though counterintuitive, DF will stay elevated until nearly all channels become constitutively reluctant. FIG. 7B explicitly calculates this outcome, where the pseudoplateau created in the right two-thirds of the curve documents the insensitivity of DF to declining A. For concreteness, DF values are shown for various control and peptide experiments (FIG. 7C). For many perturbations, DF approaches unity, consistent with approximately complete conversion to constitutively reluctant channels. However, DF approximates 4 for free $NT_B$ with Gβγ, seemingly at odds with strong G/Q depression (FIG. 4A). FIG. 7B shows that a DF~4 nonetheless reflects strong, ~75%, conversion to constitutively reluctant channels.

The free $NT_B$ peptides described herein offer novel means to attenuate pain, alone or by working in conjunction with morphine to potentiate analgesia driven by G protein inhibition of N-type channels. According to FIG. 6B, effective levels of N-type channel inhibition might be achieved at lower doses of morphine, or even for some period after opiate withdrawal. $NT_B/I-II_B$ hybridization assays (FIGS. 1D and 1Ef) may furnish a basis of high-throughput library screens for inorganic surrogates of $NT_B$ (Young et al., 1998), as compounds inhibiting hybridization would represent promising candidates for higher-order refinement. Moreover, analogous screens with $NH_3$ termini of other $Ca_v2$ channels could uncover selective congeners for the other channel types and their customized biological functions. Overall, the $NT_B$ module may impact mechanistic, biological, and even therapeutic realms of inquiry.

Transfection of HEK293 Cells

Cells were transiently transfected and cultured in 10 cm plates (Brody et al., 1997). For 2+$Ca^{2+}$ channels, 8 µg was used of each of cDNAs of the desired $a_1$, rat brain β2a (Perez-Reyes et al., 1992), and rat brain $a^28$ (Tomlinson et al., 1993) subunits; along with 2 µg T-antigen cDNA. N-type $α_{1B}$, human origin (NM000718); L-type $α_{1C}$, rabbit (Wei et al., 1991) (X15539). Gβγ coexpressed with 4 µg each of $Gβ_1$ (Sugimoto et al., 1985) and $Gγ_2$ (Gautam et al., 1990). For coexpression of N-terminal peptides, channel subunit cDNA reduced to 6 µg, while adding 14 µg peptide cDNA. For receptor experiments, 0.5 µg cDNA for m2R (below) applied with other cDNAs.

Electrophysiology

Whole-cell current records were made with Axopatch 200B (Axon Instruments, Calif.), 1-3 days posttransfection. Pipets, 1.5-3 MΩ before 60-75% series resistance compensation. Internal solution: 135 mM $CsMeSO_4$, 5 mM CsCl, 10 mM EGTA, 10 mM HEPES, 1 mM $MgCl_2$, and 4 mM MgATP. External solution: 150 mM $TEAMeSO_4$, 10 mM HEPES, 2 mM $CaCl_2$, and 1 mM $MgCl_2$. During constitutive inhibition (or as noted for some chimeras), 20 mM $BaCl_2$ was substituted for 2 mM $CaCl_2$, and the resulting solution was diluted 1.08×. To compare across external solutions, a conversion factor of 3.18 was used. Currents and conductances with 20 mM $Ba^{2+}$ were thus scaled×1/3.18 to facilitate uniform comparison of values, as if all data had been collected with 2 mM $Ca^{2+}$. When applied, conversion is denoted by asterisk (*). Ionic currents, 2 kHz filter; gating currents, 5 kHz. Leak and capacity currents were P/8 corrected. Analysis by custom MATLAB software (MathWorks, Natick, Mass.) and Microsoft Excel. Compound-state analysis was performed as described (Agler et al., 2003). Population data are shown as mean±SEM. G/Q regression analysis is as described in Glantz and Slinker (1990); slopes were considered statistically different than control (FIG. 3A) at p<0.001 (**); slope shown as mean±SEM, where ±SEM denotes 67% confidence interval.

Molecular Biology

Human m2 muscarinic acetylcholine receptor (AF498916) was engineered to reduce desensitization (Pals-Rylaarsdam and Hosey, 1997). QuikChange (Stratagene, La Jolla, Calif.) introduced cluster mutations, yielding m2R: residues 286-290 (STSVS/AAAVA), residues 307-311 (TVSTS/AVAAA). For FRET assays, base templates were ECFP/EYFP-tagged calmodulin constructs in pcDNA3 (Invitrogen, Carlsbad, Calif.), as described (Erickson et al., 2001). PCR-amplified channel segments or G proteins were substituted for calmodulin via upstream EcoRI and downstream NheI sites, creating in-frame fusions with fluorophore (ECFP/EYFP C-terminal to test molecules). For $NT_B$ segments, residues are shown in FIG. 5A. $NT_C$ residues, 1-53; $I-II_B$ residues, 357-482; and $I-II_C$ residues, 436-554.

For yeast two-hybrid assays, a PCR fragment encoding one partner was fused, in-frame, with the GAL4 DNA binding domain (BD) in pGBKT7 (Clontech, Palo Alto, Calif.). The other element was fused, in-frame, with the GAL4 activation domain (AD) in pGADT7. For specific residues, see Supplemental Data (section 2). For electrophysiology, NT peptides lacking fluorophore tag were PCR amplified and cloned in pcDNA3. $NT_B$ peptide residues, 1-95; $NT_C$ residues, 1-153. Throughout, all segments subject to PCR or QuikChange were verified in their entirety by sequencing.

Yeast Two-Hybrid Assays

The Matchmaker GAL4 Two-Hybrid System 3 was used (Clontech, Palo Alto, Calif.). AH109 yeast were transformed with pGBKT7/pGADT7-based constructs (Yeastmaker Yeast Transformation System 2 kit, Clontech). After 5-8 days, growth on -leucine/-trytophan plates confirmed transformation of both plasmids. If partners interact, GAL4 BD/AD would complex, activating reporter genes (HIS3, ADE2, lacZ, and MEL1), for which assays are detailed in the Supplemental Data (section 2.1).

FRET Two-Hybrid Analysis

Experiments were performed mostly as previously described (Erickson et al., 2001; Erickson et al., 2003). Briefly, the FRET Ratio (FR) is the fractional increase in YFP emission due to FRET. In the three-cube FRET mode, $$FR=[S_{FRET}-(R_{D1})(S_{CFP})]/[(R_{A1})(S_{YFP}-(R_{D2})(S_{CFP}))],$$

where $S_X$ is the whole-cell fluorescence measurement with the indicated filter cube (X), and experimentally determined $R_{D1}$, $R_{D2}$, and $R_A$ values (0.3346, 0.0051, and 0.0281, respectively) did not vary significantly among the various CFP- and YFP-tagged constructs. For donor-dequenching analysis, $E_{EFF}$ is calculated as $E_{EFF}=1-CFP_{pre}/CFP_{post}$, where $CFP_{pre}$ and $CFP_{post}$ are the CFP emissions before/after 3 min YFP photobleaching. FR is determined by $FR=(E_{EFF}/[\epsilon_{YFP}/\epsilon_{CFP}])+1$, where EYFP/ECFP is ratio of YFP and CFP molar extinction coefficients through 440 nm excitation bandpass of FRET cube (0.0574). For binding model analysis, $K_{d,EFF}$ is the effective dissociation constant, related to actual $K_d$ via filter/microscope optical characteristics.

G-Protein Modulation of $\alpha_{1bBbBBBb\Delta}$ Channels

Figure 8:
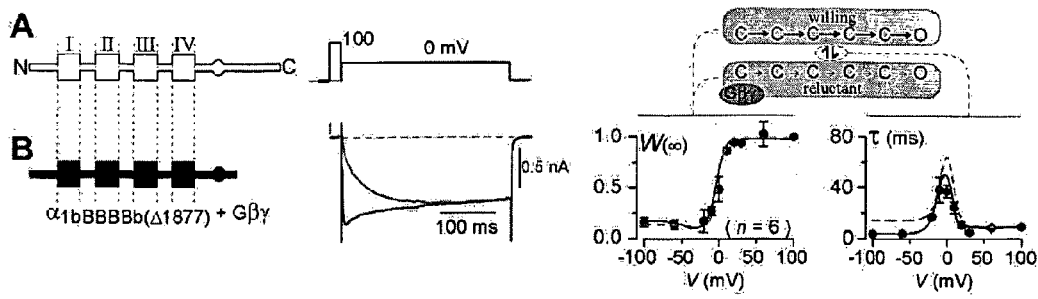
FIG. 8 demonstrates the results with an additional channel deletion, and construction of channel deletions and chimeras, e.g., the persistence of G-protein modulation in α$_{1bBbBBBbA}$ channel with C-tail truncation (at residue 1877), without subsequent fusion to YFP. Modulatory profile is near unchanged from control (FIG. 8A). Format as in FIG. 1A.

In regard to FIGS. 1D and 8, simple deletion of the entire distal COOH tail of $\alpha_{1B}$, without substitution of a YFP, were tested for control-like G-protein modulation. FIG. 8 shows the results for such $\alpha_{1bBbBBBb\Delta}$ channels. Exemplar current traces gave clear evidence of strong G-protein modulation, for which the quantitative profile was near indistinguishable from that of the wild-type channel (FIG. 8). Thus, addition of the YFP moiety did not impact significantly the profile of G-protein modulation.

Construction of Channel Deletions and Chimeras

The engineered channels in FIG. 1 were created with strategies based on polymerase chain reaction (PCR). The channel chimera shown in FIG. 1C ($\alpha_{1bBcBBBb}$) was created by overlap extension (Ho et al., 1989). The 'left' PCR amplified $\alpha_{1B}$ residues 45-356. For orientation, residue 357 would be the first amino acid of the I-II$_B$ loop element. A unique Cla I site, at residue 48, is included near the beginning of the PCR product, and the downstream oligo appends additional base pairs encoding the beginning of the I-II$_C$ loop element, starting with $\alpha_{1C}$ residue 436. The 'right' PCR amplified $\alpha_{1C}$ residues 436-517, corresponding to the I-II$_C$ loop element. The upstream oligo appends additional base pairs encoding $\alpha_{1B}$ residues just upstream of the I-II$_B$ loop element. The downstream oligo appends additional base pairs encoding $\alpha_{1B}$ residues downstream of all I-II$_B$ loop elements implicated in G-protein modulation (Zamponi et al., 1997), including base pairs corresponding to a unique Age I site in $\alpha_{1B}$. 'Left' and 'right' PCR reactions were combined in a third 'combinatorial' PCR, which was digested with Cla I and Age I restriction receptors, and cloned into these unique sites within the $\alpha_{1B}$ backbone. The result is a construct encoding the chimeric channel diagrammed in FIG. 9A.

Figure 9:
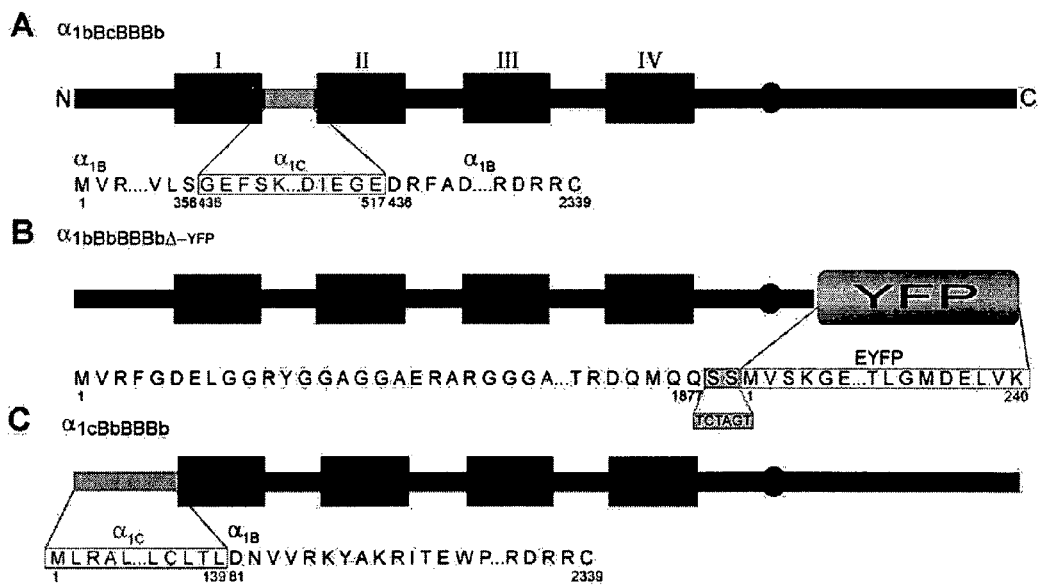
FIG. 9 shows the further exposition of yeast two-hybrid assays, composition of yeast two-hybrid interaction segments, controls for auto-activation of transcription factors, and additional interacting partners. The sequences for chimeric and truncated channels: four homologous domains labeled I-IV. (A) For the I-II loop chimera, amino acids 357 to 435 of α$_{1B}$ were replaced with amino acids 436 to 517 of α$_{1C}$. (B) The α$_{1B}$ channel was truncated at amino acid 1877 and fused to an EYFP. The two serines, situated in between α$_{1B}$ and EYFP, are left over from the ligation of overlapping regions of Xba I and Spe I restriction cuts. (C) The NH$_3$- terminal chimera was created by replacing amino acids 1 to 80 of $\alpha_{1B}$ with amino acids 1 to 139 of $\alpha_{1C}$.

To create an $\alpha_{1B}$ subunit in which YFP has been substituted for the distal COOH terminus (FIG. 1D, $\alpha_{1bBbBBBb\Delta-YFP}$), first was created a custom a1B subunit in which a silent Xba I site was created at the 5' end of the COOH terminus. This produced an $\alpha_{1B}$* construct in which base pairs encoding the COOH terminus were flanked by a unique pair of Xba I sites. Second, was created a PCR amplified $\alpha_{1B}$* regions that incorporated the upstream Xba I site at the 5' end, and proceeded through base pairs encoding residue 1877 at the 3' end. The downstream oligo appended an Xba I site. This PCR fragment was then cloned via flanking Xba I sites into the corresponding sites of $\alpha_{1B}$*, producing a 'stop-less' $\alpha_{1B}$* truncated after residue 1877. A stop codon does exist in the multi-cloning site of pcDNA3, positioned the equivalent of 12 amino acids C-terminal to residue 1877. Thus, this construct corresponds to the functional C-terminal deletion channel ($\alpha_{1bBbBBBb\Delta}$, FIG. 5I). Third, full-length EYFP was PCR amplified with oligos appending Spe I (upstream) and Xba I sites (downstream). Because Spe I and Xba I have compatible cohesive ends, the resulting PCR product could be inserted into the pair of Xba I sites in $\alpha_{1B}$*, producing $\alpha_{1bBbBBBb\Delta-YFP}$ (FIG. 9B). The NH$_3$-terminal chimera $\alpha_{1cBbBBBb}$ (FIG. 1E) was created by PCR amplification of an $\alpha_{1C}$ segment encoding residues 1-139 (corresponding to NT$_C$). The upstream oligo appended an EcoRI site, and the downstream oligo appended an Asp I site. This PCR product was ligated into unique EcoRI and Asp I sites, which were situated on an EcoRI/Bgl II fragment of a1B cloned in pGEM. This effectively switched $\alpha_{1B}$ residues 1-80 for $\alpha_{1C}$ residues 1-139. This amended fragment of $\alpha_{1B}$ was transferred by EcoRI and Bgl II sites into the full-length $\alpha_{1B}$ construct, producing $\alpha_{1cBbBBBb}$ (FIG. 9).

In-Depth Description of Yeast Two-Hybrid Assays

As a 'medium' stringency assay, expression of the lacZ gene was tested for encoding β-galactosidase, performing a filter lift with application of blue chromogenic substrate (Clontech-Laboratories, 1999). After the filter lift, original plates were re-grown for 2-3 days at 30° C. Filter paper was then used to replicate colonies onto a high stringency plate (-adenine/-histidine/-leucine/-trytophan). These plates were then incubated at 30° C. for 5-8 days. Survival on high stringency plates indicates production of both adenine and histidine, from transcription of the ADE2 and HIS3 genes, respectively. The percentage of colonies that turned blue in the filter lift assay, along with the percentage of colonies that survived on high stringency plates, was recorded for each pairing. Experiments were repeated at least three times. False positives were controlled for by testing each segment in pGBKT7 against empty pGADT7, and each segment in pGADT7 against lamin C in pGBKT7 (lamin C interacts with few proteins). Average sum of these backgrounds was subtracted from B to produce the net interaction parameter ΔB (FIG. 2).

In specific regard to the exemplar positive interaction experiment (FIG. 2A), the colonies apparent on the 'no selection' plates (lacking leucine and tryptophan) were only indicative of successful incorporation of both types of plasmids, but made no statement regarding Gβ$_1$/I-II$_B$ association. Requisite receptors for these essential amino acids were encoded on the plasmids containing activation and binding domains, but no interaction between fusion peptides need have occurred to permit colony growth under these conditions. The first indication of actual binding came with a filter lift of 'no selection' colonies, followed by subsequent testing for expression of β-galactosidase. Such expression would only occur if Gβ$_1$/I-II$_B$ interaction were to bring activation and binding domains together in close proximity, thus driving production of β-galactosidase and conversion of a blue chromogenic substrate ('medium' assay conditions). To provide a more stringent test of binding, 'no selection' colonies were replicated onto media lacking both adenine and histidine (in addition to leucine and tryptophan). Robust Gβ$_1$/I-II$_B$ interaction would be required to permit transcription of factors required for production of adenine and histidine, both of which would be required for the enlargement of white-colored colonies as observed under 'high' stringency conditions. Concerning exemplar negative control experiments (FIG. 2B), the pale colonies seen in the 'high' selection context were punctuated by red foci, which are characteristic of an adenine deficient state for the particular yeast strain employed in these experiments (Clontech-Laboratories, 1999).

Yeast Two Hybrid Construct Details and Controls for Auto-Activation

The composition of yeast two-hybrid interaction segments is detailed below, along with extensive controls for auto-activation of transcription factors. In particular, those proteins or peptides cloned into pGADT7 (activation domain) were tested against pGBKT7-lamin C, since lamin C binds very few proteins. Those proteins or peptides cloned into pGBKT7 (binding domain) were tested against empty pGADT7. Results of these controls are shown in Table 1. Values in parentheses show residues of parent constructs that have been incorporated into hybridization constructs.

TABLE 1

| Yeast two-hybrid controls Construct | Filter Lift Assay (%) | Number of Transformations | High Stringency (%) | Number of Transformations |
|---|---|---|---|---|
| T-pGADT7 & p53-pGBKT7 | 89.96 ± 4.74 | 6 | 89.05 ± 5.20 | 6 |
| T-pGADT7 & lam-pGBKT7 | 0.23 ± 0.23 | 5 | 0.00 ± 0 | 6 |
| I-II$_B$(357-482)-pGADT7 & lam-pGBKT7 | 0.00 ± 0 | 3 | 0.74 ± 0.74 | 4 |
| I-II$_C$(436-554)-pGADT7 & lam-pGBKT7 | 0.00 ± 0 | 3 | 0.00 ± 0 | 3 |
| pGADT7 & CT$_C$(1525-1670)pGBKT7 | 0.00 ± 0 | 3 | 0.00 ± 0 | 3 |
| pGADT7 & CT$_A$(1763-1928)pGBKT7 | 0.00 ± 0 | 3 | 0.10 ± 0.10 | 3 |
| pGADT7 & I-II$_B$(357-482)-pGBKT7 | 9.18 ± 4.88 | 3 | 18.67 ± 5.95 | 4 |
| pGADT7 & I-II$_C$(436-554)-pGBKT7 | — | — | 8.44 ± 5.49 | 3 |
| pGADT7 & NT$_B$(1-95)-pGBKT7 | 0.14 ± 0.14 | 5 | 0.34 ± 0.21 | 5 |
| pGADT7 & NT$_B$(1-55)-pGBKT7 | 1.56 ± 1.56 | 4 | 3.84 ± 2.29 | 4 |
| pGADT7 & NT$_C$(1-153)-pGBKT7 | 0.00 ± 0 | 4 | 1.00 ± 1.00 | 3 |
| pGADT7 & NT$_A$(2-100)pGBKT7 | 0.82 ± 0.82 | 3 | 0.00 ± 0 | 3 |
| pGADT7 & NT$_B$(45-95)-pGBKT7 | 0.00 ± 0 | 4 | 0.00 ± 0 | 5 |
| pGADT7 & NT$_B$(1-44)-pGBKT7 | 47.94 ± 28.21 | 3 | 0.98 ± 0.98 | 4 |
| pGADT7 & NT$_B$(56-95)-pGBKT7 | 32.25 ± 20.12 | 4 | 2.11 ± 1.30 | 5 |
| pGADT7 & NT$_B$(Δ45-55)-pGBKT7 | 2.50 ± 2.22 | 5 | 0.56 ± 0.56 | 3 |
| I-II$_B$(357-397)-pGADT7 & lam-pGBKT7 | — | — | 0.00 ± 0.00 | 3 |
| I-II$_B$(398-435)-pGADT7 & lam-pGBKT7 | — | — | 0.04 ± 0.04 | 3 |
| I-II$_B$(436-482)-pGADT7 & lam-pGBKT7 | — | — | 0.00 ± 0.00 | 3 |

Additional Interacting Partners by Yeast Two Hybrid Assays

Another outcome of the yeast- and FRET two-hybrid assays is that Gβ$_1$ gave evidence of interaction with the I-II$_C$ loop element (FIG. 10), further underscoring the importance of the NT$_B$ module in supporting G-protein modulation of N-type channels.

Figure 3:
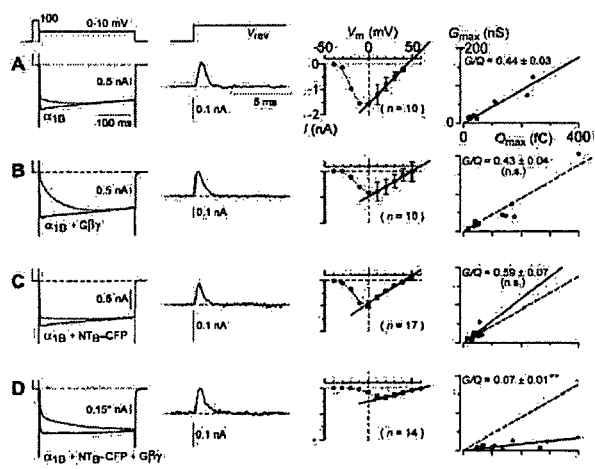
FIG. 3 demonstrates that the α$_{1B}$ NH$_3$-terminal peptide produces constitutive channel inhibition. G/Q analysis for N-type channels, without Gβγ. (Left) Exemplar currents with (black) and without prepulse (gray), via protocol above. (Left middle) Gating current at reversal potential (~50 mV), same cell. Q$_{max}$, area under gating current. (Right middle) Peak currents during voltage steps following a 30 ms prepulse (top left). Number of cells in parenthesis. G$_{max}$, linear regression slope. (Right) G$_{max}$-Q$_{max}$ plot for multiple cells. G/Q slope (mean±SEM), proportional to maximal channel open probability. G/Q analysis, N-type channels with Gβγ. Format as above (A). G/Q indistinguishable (n.s.) from control (A). (Right) Dashed line, fit to control (A) throughout. G/Q analysis, N-type channels, with NT$_B$-CFP (as in FIG. 2Eb), without Gβγ. Format as above (A). G/Q indistinguishable (n.s.) from control (A). G/Q analysis for N-type channels, with NT$_B$-CFP and Gβγ. Marked suppression of G/Q (**p<0.001) relative to control (A). Format as above (A). *Currents with 20 mM Ba$^{2+}$, converted to 2 mM Ca$^{2+}$ equivalent. G/Q and G$_{max}$ also compensated (Supplemental Data, section 3).

FIG. 3 Supplement: Conductance Conversion Factor

Most of the electrophysiological data was gathered using an external solution containing 2 mM Ca$^{2+}$ as charge carrier. In some cases, when the currents were small, external solution containing 20 mM Ba$^{2+}$ was used for purposes of improving signal-to-noise ratios. To enable comparison of data obtained in different solutions, the maximal conductance for individual cells in the two solutions was determined, as well as the ratio of conductances. To relieve any residual G-protein inhibition, conductances were determined for step depolarizations that followed shortly after a 30-ms prepulse to 100 mV (FIG. 11A and 11B, right). For 10 cells, the ratio $G_{max}$ (20 mM Ba$^{2+}$)/$G_{max}$ (2 mM Ca$^{2+}$) was 3.18±0.22. This conversion factor was used to convert the conductances in 20 mM Ba$^{2+}$ to calculated conductances in 2 mM Ca$^{2+}$. The consistency of the conversion ratio can be gauged by the average conductance and current-voltage relationships shown in FIG. 11.

Engineered Muscarinic Receptor Exhibits Little Desensitization

It was found that the m2 muscarinic receptor (AF498916) desensitizes to carbachol after only 10-15 minutes at 37° C. To obviate this limitation, several mutations in two different phosphorylation regions were made (Pals-Rylaarsdam and Hosey, 1997). The first region 'N' (residues 286-290) was mutated from STSVS to AAAVA, and the second region 'C' (residues 307-311) was mutated from TVSTS to AVAAA. FIG. 12A shows a typical pair of currents evoked by test depolarization to 0 mV, obtained with and without a depolarizing prepulse. FIG. 12B shows the increase in modulation that occurs with the acute application of carbachol. FIG. 12C shows the persistence of modulation even after 60 minutes of carbachol at 37° C. Population data in FIG. 7C (right) confirm these trends.

Construction of α$_{1bΔ(56-90)BbBBBb}$

To further demonstrate the functional impact of α$_{1B}$ amino acids 56-95, an α$_{1B}$ channel that had residues 56-90 deleted was created (FIG. 5D, α$_{1bΔ(56-90)BbBBBb}$). To create this construct, overlap-extension PCR was used (Ho et al., 1989). In the 'left' PCR, α$_{1B}$ as template, and amplified an EcoRI site (upstream of the start codon of α1B) along with residues 1-55 of α$_{1B}$ was used. The downstream oligo also encoded α$_{1B}$ residues 91-96. The 'right' PCR amplified sequence encoding α$_{1B}$ residues 91-1462. The upstream oligo appended sequence encoding α$_{1B}$ residues 51-55, and the 3' end of the PCR product spanned a unique Bgl II site. 'Left' and 'right' PCR reactions were combined in a third 'combinatorial' PCR, which was digested with EcoRI and Bgl II restriction receptors, and cloned into corresponding sites on the α$_{1B}$ backbone. The result is a construct encoding the chimeric channel diagrammed in Figure S6.

NT$_B$ Residues 56-95 are Necessary for Constitutive Inhibition

FIG. 5C shows suppression of $G_{max}$ versus $Q_{max}$ plots by NT$_B$ sub-domains that retain interaction with the I-II$_B$ loop element (NT$_B$ (45-95) and NT$_B$ (56-95)). In FIG. 14, is presented the complete set of ancillary data relating to these plots, following the format of FIG. 3. In reference to FIG. 15, I-II$_B$ is sub-mapped for interaction with NT$_B$.

Further Dimensions of the G-Protein Modulatory Mechanism in FIG. 6

An alternative scenario where NT$_B$ and I-II$_B$ elements within a holo-channel already interact without Gβγ, and subsequent Gβγ binding simply permits the NT$_B$/I-II$_B$ interaction to convey inhibition to the channel was considered. However, this alternative predicts that receptor-mediated peptide inhibition (FIG. 4D) should be rapidly induced by carbachol, at odds with the ~10-minute induction required for constitutive inhibition following receptor activation. Also, in these experiments (FIG. 4D), acute carbachol application (with NT$_B$ peptide present) rapidly inhibited currents featuring normal prepulse facilitation (DF=2.64±0.18, n=6). Thus, Gβγ readily accessed the channel, and the delayed onset of constitutive inhibition must reflect other events. By contrast, FIG. 6B explains the induction delay as the time required for free NT$_B$ to penetrate and associate with a channel, once becoming permissive for interaction by Gβγ.

Auxiliary Ca$^{2+}$ channel B subunits interact tightly with an 'AID' subsection of the I-II$_C$ linker (Chen et al., 2004; Opatowsky et al., 2004; Van Petegem et al., 2004), and Gβγ binding to the I-II$_B$ loop overlies the analogous AID subsection (De Waard et al., 1997). The yeast assays suggest that the NT$_B$ peptide also interacts with the NH$_3$-terminal third of the I-II$_B$ loop, containing the AID site.

Derivation of Explicit Functions in FIGS. 7A and 7B

Consider FIG. 7A. Because $G_{max}$ is determined after prepulse depolarization, reluctant channels are nearly all converted to the willing configuration (FIG. 6A). Aggregate $P_{o,max}$ (which underlies G/Q assays) can thus be deduced by considering only the partitioning of channels between willing and constitutively reluctant pools (measurements are made after a strong depolarizing prepulse), yielding $$P_{o,max} = A \cdot P_{o,max,willing} + (1-A) \cdot P_{o,max,constitutively\ reluctant} \quad (1)$$

where A is the fraction of willing channels (after strong prepulse depolarization), 1-A is the fraction of constitutively reluctant channels, $P_{o,max,\ willing}$ is the open probability of willing channels measured in the 10-40 mV range, and $P_{o,max,\ constitutively\ reluctant}$ is the open probability of constitutively reluctant channels over this same voltage range. Presuming that reluctant and constitutively-reluctant channels share the same open probability, the earlier single-channel data would estimate that $P_{o,max,willing} \sim 0.5$ and $P_{o,max,constitutively\ reluctant} \sim 0.02$ (FIG. 3H in Colecraft et al (2001)). Hence, Equation 1 approximates to $P_{o,max} \sim A \cdot P_{o,max,willing}$, so that G/Q declines in nearly direct proportion to decreasing A. This is explicitly demonstrated by the plot of G/Q versus A (FIG. 7A), as determined from Equation 1.

Consider FIG. 7B. It might appear that decreasing DF (with Gβγ present) would also be an appropriate measure of constitutive inhibition, because DF would equal to unity if all channels were constitutively reluctant (FIG. 6B, bottom). However, this outcome would not occur until nearly all channels have become constitutively reluctant. Though prepulse depolarization would not enhance constitutively reluctant channels, the contribution of these channels to whole-cell current would be small, due to their low open probability. Hence, even a small remnant of channels resisting constitutive inhibition would contribute disproportionately to current, owing to their larger open probability. This intuitive argument can be made explicit by Equation 2, which specifies aggregate DF as a function of the fraction of willing channels after strong prepulse depolarization (A)

$$DF = \frac{A \cdot P_{o,max,willing} + (1-A) \cdot P_{o,max,constitutively\ reluctant}}{[P_{o,max,willing} \cdot (1-R) + P_{o,max,reluctant} \cdot R] + A \cdot (1-A) \cdot P_{o,max,constitutively\ reluctant}} \quad (2)$$

where $P_{o,max,reluctant}$ is the open probability of reluctant channels (FIG. 6A, bottom) measured in the 10-40 mV range, and R is the number of reluctant channels divided by the total number of reluctant and willing channels. FIG. 7B plots this equation, using the approximate single-channel parameters $P_{o,max,reluctant} \sim 0.5$ and $P_{o,max,constitutively\ reluctant} \sim P_{o,max,reluctant} \sim 0.02$ (Colecraft et al., 2001), and R set at 0.87 to match experimentally determined DF in the absence of peptide inhibition.

Specific FRET Methodology

Experiments were performed as described previously for the most part (Erickson et al., 2001; Erickson et al., 2003). Specifically, for quantitative analysis, all fluorescence from single cells were isolated through a pinhole in the image plane, and detected by photo-multiplier tube. In all three-cube FRET experiments, CFP levels were below a threshold where spurious, concentration-dependent FRET became significant (Stratton et al., 2004). Similarly, for donor-dequenching experiments, YFP levels were below an analogous threshold. Filter-cubes (excitation, dichroic, emission, company): CFP (D440/20X, 455DCLP, D480/30M, Chroma); YFP (500RDF25, 525DRLP, 530EFLP, Omega Optical); FRET (D436/20X, 455DCLP, D535/30M, Chroma); YFP photobleaching cube (HQ535/50X, 100% mirror, blank, Chroma).

Binding-model analysis assumed a 1:1 ligand-binding model to determine two parameters, $FR_{max}$ and $K_{d,EFF}$. In the three-cube FRET mode, $FR_{max}$ is the theoretical maximum FR when all acceptor-tagged molecules are bound. In the donor-dequenching mode, $FR_{max}$ corresponds to the theoretical maximum $E_{EFF}$ when all donor-tagged molecules are bound. $FR_{max}$ depends only upon inter-fluorophore geometry. The second parameter $K_{d,EFF}$, the effective dissociation constant, furnishes the relative dissociation constant for the binding reaction, with conversion factors to actual $K_d$ determined by optical characteristics of our microscope system. In FIGS. 2Ef and 5B, standard error bars for $K_{d,EFF}$ were determined by Jacobian error matrix analysis (Billo, 2001). Where error bars are not shown, the mean values represent lower-limit estimates of $K_{d,EFF}$. Due to low-affinity interaction in these cases, fits of the binding equation were unobtainable in the usual fashion. As the $FR_{max}$ parameter was set to progressively higher values, the numerical solver converged to increasingly larger $K_{d,EFF}$ values. $FR_{max}$ values greater than 10.8 (corresponding to 50% FRET efficiency) are probably unrealizable, due to the 'tin-can' structure surrounding fluorophore moieties in GFP (Ormo et al., 1996); even CFP-YFP fusions with short linkers produce $FR_{max}$ less than this value (Erickson et al., 2001). Setting $FR_{max} = 10.8$ thus produced the lower-limit $K_{d,EFF}$ values shown for low-affinity interactions.

A number of embodiments of the invention have been described. Nevertheless, it will be understood that various modifications may be made without departing from the spirit and scope of the invention. Accordingly, other embodiments are within the scope of the following claims.

REFERENCES

Agler, H. L., Evans, J., Colecraft, H. M., and Yue, D. T. (2003). Custom distinctions in the interaction of G-protein beta subunits with N-type ($Ca_v2.2$) versus P/Q-type ($Ca_v2.1$) calcium channels. J. Gen. Physiol. 121, 495-510.

Allen, J. B., Walberg, M. W., Edwards, M. C., and Elledge, S. J. (1995). Finding prospective partners in the library: the two-hybrid system and phage display find a match. Trends Biochem. Sci. 20, 511-516.

Artim, D. E., and Meriney, S. D. (2000). G-protein-modulated $Ca^{2+}$ current with slowed activation does not alter the kinetics of action potential-evoked $Ca^{2+}$ current. J. Neurophysiol. 84, 2417-2425.

Bastiaens, P. I., and Jovin, T. M. (1996). Microspectroscopic imaging tracks the intracellular processing of a signal transduction protein: fluorescent-labeled protein kinase C beta I. Proc. Natl. Acad. Sci. USA 93, 8407-8412.

Bean, B. P. (1989). Neurotransmitter inhibition of neuronal calcium currents by changes in channel voltage dependence. Nature 340, 153-156.

Bell, T. J., Thaler, C., Castiglioni, A. J., Helton, T. D., and Lipscombe, G Protein Inhibition of N-Type $Ca^{2+}$ Channels 903 D. (2004). Cell-specific alternative splicing increases calcium channel current density in the pain pathway. Neuron 41, 127-138.

Bliss, M. (1999). William Osler: A Life in Medicine (New York: Oxford University Press).

Boland, L. M., and Bean, B. P. (1993). Modulation of N-type calcium channelCav2s in bullfrog sympathetic neurons by luteinizing hormone-releasing hormone: kinetics and voltage dependence. J. Neurosci. 13, 516-533.

Bourinet, E., Soong, T. W., Stea, A., and Snutch, T. P. (1996). Determinants of the G protein-dependent opioid modulation of neuronal calcium channels. Proc. Natl. Acad. Sci. USA 93, 1486-1491.

Brody, D. L., and Yue, D. T. (2000). Relief of G-protein inhibition of calcium channels and short-term synaptic facilitation in cultured hippocampal neurons. J. Neurosci. 20, 889-898.

Brody, D. L., Patil, P. G., Mulle, J. G., Snutch, T. P., and Yue, D. T. (1997). Bursts of action potential waveforms relieve G-protein inhibition of recombinant P/Q-type $Ca^{2+}$ channels in HEK 293 cells. J. Physiol. 499, 637-644.

Canti, C., Page, K. M., Stephens, G. J., and Dolphin, A. C. (1999). Identification of residues in the N terminus of alpha1B critical for inhibition of the voltage-dependent calcium channel by Gbeta gamma. J. Neurosci. 19, 6855-6864.

Chen, Y. H., Li, M. H., Zhang, Y., He, L. L., Yamada, Y., Fitzmaurice, A., Shen, Y., Zhang, H., Tong, L., and Yang, J. (2004). Structural basis of the alpha 1-beta subunit interaction of voltage-gated $Ca^{2+}$ channels. Nature 429, 675-680.

Clontech-Laboratories. (1999). MATCHMAKER GAL4 Two-Hybrid System 3 & Libraries User Manual, pp. 1-37.

Colecraft, H. M., Patil, P. G., and Yue, D. T. (2000). Differential occurrence of reluctant openings in G-protein-inhibited N- and P/Q-type calcium channels. J. Gen. Physiol. 115, 175-192.

Colecraft, H. M., Brody, D. L., and Yue, D. T. (2001). G-protein inhibition of N- and P/Q-type calcium channels: distinctive elementary mechanisms and their functional impact. J. Neurosci. 21, 1137-1147.

De Waard, M., Liu, H., Walker, D., Scott, V. E., Gurnett, C. A., and Campbell, K. P. (1997). Direct binding of G-protein betagamma complex to voltage-dependent calcium channels. Nature 385, 446-450.

Doering, C. J., Kisilevsky, A. E., Feng, Z. P., Arnot, M. I., Peloquin, J., Hamid, J., Barr, W., Nirdosh, A., Simms, B., Winkfein, R. J., and Zamponi, G. W. (2004). A single Gbeta subunit locus controls cross-talk between protein kinase C and G protein regulation of N-type calcium channelCav2s. J. Biol. Chem. 279, 29709-29717.

Dolphin, A. C. (2003). G protein modulation of voltage-gated calcium channels. Pharmacol. Rev. 55, 607-627.

Dunlap, K. (1997). Calcium channels. Integration hot-spot gets hotter. Nature 385, 394-395, 397.

Dunlap, K., Luebke, J. I., and Turner, T. J. (1995). Exocytotic $Ca^{2+}$ channels in mammalian central neurons. Trends Neurosci. 18, 89-98.

Elmslie, K. S. (2003). Neurotransmitter modulation of neuronal calcium channels. J. Bioenerg. Biomembr. 35, 477-489.

Elmslie, K. S., Zhou, W., and Jones, S. W. (1990). LHRH and GTP-gamma-S modify calcium current activation in bullfrog sympathetic neurons. Neuron 5, 75-80.

Erickson, M. G., Alseikhan, B. A., Peterson, B. Z., and Yue, D. T. (2001). Preassociation of calmodulin with voltage-gated $Ca^{2+}$ channels revealed by FRET in single living cells. Neuron 31, 973-985.

Erickson, M. G., Liang, H., Mori, M. X., and Yue, D. T. (2003). FRET two-hybrid mapping reveals function and location of L-type $Ca^{2+}$ channel CaM preassociation. Neuron 39, 97-107.

Garcia, D. E., Li, B., Garcia-Ferreiro, R. E., Hernandez-Ochoa, E. O., Yan, K., Gautam, N., Catterall, W. A., Mackie, K., and Hille, B. (1998). G-protein beta-subunit specificity in the fast membrane-delimited inhibition of $Ca^{2+}$ channels. J. Neurosci. 18, 9163-9170.

Gautam, N., Northup, J., Tamir, H., and Simon, M. I. (1990). G protein diversity is increased by associations with a variety of gamma sub-units. Proc. Natl. Acad. Sci. USA 87, 7973-7977.

Geib, S., Sandoz, G., Comet, V., Mabrouk, K., Fund-Saunier, O., Bichet, D., Villaz, M., Hoshi, T., Sabatier, J. M., and De Waard, M. (2002). The interaction between the I-II loop and the III-IV loop of Cav2.1 contributes to voltage-dependent inactivation in a beta-dependent manner. J. Biol. Chem. 277, 10003-10013.

Glantz, S., and Slinker, B. (1990). Primer of Applied Regression and Analysis of Variance (New York: McGraw-Hill).

Hamid, J., Nelson, D., Spaetgens, R., Dubel, S. J., Snutch, T. P., and Zamponi, G. W. (1999). Identification of an integration center for cross-talk between protein kinase C and G protein modulation of N-type calcium channelCav2s. J. Biol. Chem. 274, 6195-6202.

Herlitze, S., Garcia, D. E., Mackie, K., Hille, B., Scheuer, T., and Catterall, W. A. (1996). Modulation of $Ca^{2+}$ channels by G-protein beta gamma subunits. Nature 380, 258-262.

Ikeda, S. R. (1996). Voltage-dependent modulation of N-type calcium channelCav2s by G-protein beta-gamma subunits. Nature 380, 255-258.

Ivanina, T., Blumenstein, Y., Shistik, E., Barzilai, R., and Dascal, N. (2000). Modulation of L-type $Ca^{2+}$ channels by gbeta gamma and calmodulin via interactions with N and C termini of alpha 1C. J. Biol. Chem. 275, 39846-39854.

Jones, L. P., Patil, P. G., Snutch, T. P., and Yue, D. T. (1997). G-protein modulation of N-type calcium channelCav2 gating current in human embryonic kidney cells (HEK 293). J. Physiol. 498, 601-610.

Jones, L. P., DeMaria, C. D., and Yue, D. T. (1999). N-type calcium channelCav2 inactivation probed by gating-current analysis. Biophys. J. 76, 2530-2552.

Kaneko, S., Yada, N., Fukuda, K., Kikuwaka, M., Akaike, A., and Satoh, M. (1997). Inhibition of $Ca^{2+}$ channel current by mu- and kappa-opioid receptors coexpressed in *Xenopus* oocytes: desensitization dependence on $Ca^{2+}$ channel alpha 1 subunits. Br. J. Pharmacol. 121, 806-812.

Kim, J., Ghosh, S., Nunziato, D. A., and Pitt, G. S. (2004). Identification of the components controlling inactivation of voltage-gated $Ca^{2+}$ channels. Neuron 41, 745-754.

Li, B., Zhong, H., Scheuer, T., and Catterall, W. A. (2004). Functional role of a C-terminal Gbetagamma-binding domain of $Ca_v2.2$ channels. Mol. Pharmacol. 66, 761-769.

Markram, H., and Tsodyks, M. (1996). Redistribution of synaptic efficacy between neocortical pyramidal neurons. Nature 382, 807-810.

McGee, A. W., Nunziato, D. A., Maltez, J. M., Prehoda, K. E., Pitt, G. S., and Bredt, D. S. (2004). Calcium channel function regulated by the SH3-GK module in beta subunits. Neuron 42, 89-99.

McIntosh, J. M., and Jones, R. M. (2001). Cone venom—from accidental stings to deliberate injection. Toxicon 39, 1447-1451.

Minor, D. L., Lin, Y. F., Mobley, B. C., Avelar, A., Jan, Y. N., Jan, L. Y., and Berger, J. M. (2000). The polar T1 interface is linked to conformational changes that open the voltage-gated potassium channel. Cell 102, 657-670.

Neher, E., and Steinbach, J. H. (1978). Local anaesthetics transiently block currents through single acetylcholine-receptor channels. J. Physiol. 277, 153-176.

Opatowsky, Y., Chen, C. C., Campbell, K. P., and Hirsch, J. A. (2004). Structural analysis of the voltage-dependent calcium channel beta subunit functional core and its complex with the alpha 1 interaction domain. Neuron 42, 387-399.

Page, M. I., and Jencks, W. P. (1971). Entropic contributions to rate accelerations in enzymic and intramolecular reactions and the chelate effect. Proc. Natl. Acad. Sci. USA 68, 1678-1683.

Page, K. M., Canti, C., Stephens, G. J., Berrow, N. S., and Dolphin, A. C. (1998). Identification of the amino terminus of neuronal $Ca^{2+}$ channel alpha1 subunits alpha1B and alpha1E as an essential determinant of G-protein modulation. J. Neurosci. 18, 4815-4824.

Pals-Rylaarsdam, R., and Hosey, M. M. (1997). Two homologous phosphorylation domains differentially contribute to desensitization and internalization of the m2 muscarinic acetylcholine receptor. J. Biol. Chem. 272, 14152-14158.

Patil, P. G., de Leon, M., Reed, R. R., Dubel, S., Snutch, T. P., and Yue, Neuron 904 D. T. (1996). Elementary events underlying voltage-dependent G-protein inhibition of N-type calcium channelCav2s. Biophys. J. 71, 2509-2521.

Patterson, G. H., Piston, D. W., and Barisas, B. G. (2000). Forster distances between green fluorescent protein pairs. Anal. Biochem. 284, 438-440.

Penn, R. D., and Paice, J. A. (2000). Adverse effects associated with the intrathecal administration of ziconotide. Pain 85, 291-296.

Perez-Reyes, E., Castellano, A., Kim, H. S., Bertrand, P., Baggstrom, E., Lacerda, A. E., Wei, X. Y., and Birnbaumer, L. (1992). Cloning and expression of a cardiac/brain beta subunit of the L-type calcium channel. J. Biol. Chem. 267, 1792-1797.

Qin, N., Platano, D., Olcese, R., Stefani, E., and Birnbaumer, L. (1997). Direct interaction of gbetagamma with a C-terminal gbetagamma-binding domain of the $Ca^{2+}$ channel alpha1 subunit is responsible for channel inhibition by G protein-coupled receptors. Proc. Natl. Acad. Sci. USA 94, 8866-8871.

Sadja, R., Alagem, N., and Reuveny, E. (2003). Gating of GIRK channels: details of an intricate, membrane-delimited signaling complex. Neuron 39, 9-12.

Simen, A. A., and Miller, R. J. (2000). Involvement of regions in domain I in the opioid receptor sensitivity of alpha1B $Ca^{2+}$ channels. Mol. Pharmacol. 57, 1064-1074.

Smiley, M. M., Lu, Y., Vera-Portocarrero, L. P., Zidan, A., and Westlund, K. N. (2004). Intrathecal gabapentin enhances the analgesic effects of subtherapeutic dose morphine in a rat experimental pancreatitis model. Anesthesiology 101, 759-765.

Sugimoto, K., Nukada, T., Tanabe, T., Takahashi, H., Noda, M., Minamino, N., Kangawa, K., Matsuo, H., Hirose, T., Inayama, S., et al. (1985). Primary structure of the beta-subunit of bovine transducin deduced from the cDNA sequence. FEBS Lett. 191, 235-240.

Tang, Z. Z., Liang, M. C., Lu, S., Yu, D., Yu, C. Y., Yue, D. T., and Soong, T. W. (2004). Transcript scanning reveals novel and extensive splice variations in human 1-type voltage-gated calcium channel, $Ca_v1.2$ alpha1 subunit. J. Biol. Chem. 279, 44335-44343.

Tomlinson, W. J., Stea, A., Bourinet, E., Charnet, P., Nargeot, J., and Snutch, T. P. (1993). Functional properties of a neuronal class C L-type calcium channel. Neuropharmacology 32, 1117-1126.

Van Petegem, F., Clark, K. A., Chatelain, F. C., and Minor, D. L., Jr. (2004). Structure of a complex between a voltage-gated calcium channel beta-subunit and an alpha-subunit domain. Nature 429, 671-675.

Vanegas, H., and Schaible, H. (2000). Effects of antagonists to high-threshold calcium channels upon spinal mechanisms of pain, hyperalgesia and allodynia. Pain 85, 9-18.

Varnum, M. D., and Zagotta, W. N. (1997). Interdomain interactions underlying activation of cyclic nucleotide-gated channels. Science 278, 110-113.

Wei, X. Y., Perez-Reyes, E., Lacerda, A. E., Schuster, G., Brown, A. M., and Birnbaumer, L. (1991). Heterologous regulation of the cardiac $Ca^{2+}$ channel alpha 1 subunit by skeletal muscle beta and gamma subunits. Implications for the structure of cardiac L-type $Ca^{2+}$ channels. J. Biol. Chem. 266, 21943-21947.

Wei, X., Neely, A., Olcese, R., Lang, W., Stefani, E., and Birnbaumer, L. (1996). Increase in $Ca^{2+}$ channel expression by deletions at the amino terminus of the cardiac alpha 1C subunit. Receptors Channels 4, 205-215.

Wheeler, D. B., Randall, A., and Tsien, R. W. (1994). Roles of N-type and Q-type $Ca^{2+}$ channels in supporting hippocampal synaptic transmission. Science 264, 107-111.

Wilding, T. J., Womack, M. D., and McCleskey, E. W. (1995). Fast, local signal transduction between the mu opioid receptor and $Ca^{2+}$ channels. J. Neurosci. 15, 4124-4132.

Wu, L. G., and Saggau, P. (1997). Presynaptic inhibition of elicited neurotransmitter release. Trends Neurosci. 20, 204-212.

Young, K., Lin, S., Sun, L., Lee, E., Modi, M., Hellings, S., Husbands, M., Ozenberger, B., and Franco, R. (1998). Identification of a calcium channel modulator using a high throughput yeast two-hybrid screen. Nat. Biotechnol. 16, 946-950.

Zamponi, G. W. (2001). Determinants of G protein inhibition of pre-synaptic calcium channels. Cell Biochem. Biophys. 34, 79-94. Zamponi, G. W., and McCleskey, E. W. (2004). Splicing it up. A variant of the N-type calcium channel-Cav2 specific for pain. Neuron 41, 3-4. Zamponi, G. W., and Snutch, T. P. (1998). Decay of prepulse facilitation of N type calcium channels during G protein inhibition is consistent with binding of a single Gbeta subunit. Proc. Natl. Acad. Sci. USA 95, 4035-4039.

Zamponi, G. W., Bourinet, E., Nelson, D., Nargeot, J., and Snutch, T. P. (1997). Crosstalk between G proteins and protein kinase C mediated by the calcium channel alpha1 subunit. Nature 385, 442-446.

Zhang, J. F., Ellinor, P. T., Aldrich, R. W., and Tsien, R. W. (1996). Multiple structural elements in voltage-dependent $Ca^{2+}$ channels support their inhibition by G proteins. Neuron 17, 991-1003.

Zhou, M., Morais-Cabral, J. H., Mann, S., and MacKinnon, R. (2001). Potassium channel receptor site for the inactivation gate and quaternary amine inhibitors. Nature 411, 657-661. Billo, E. J. (2001). Excel for chemists: a comprehensive guide, 2nd edn (Hoboken, N.J., Wiley-VCH).

Ho, S., Hunt, H., Horton, R., Pullen, J., and Pease, L. (1989). Site-directed mutagenesis by overlap extension using the polymerase chain reaction. Gene 77, 51-59.

Ormo, M., Cubitt, A. B., Kallio, K., Gross, L. A., Tsien, R. Y., and Remington, S. J. (1996). Crystal structure of the *Aequorea victoria* green fluorescent protein. Science 273, 1392-1395.

Stratton, J., Evans, J., Erickson, M. G., Alvania, R. S., and Yue, D. T. (2004). The nature of concentration-dependent spurious FRET arising from CFP and YFP (abstr.). Biophys J 86, 317*a*.

What is claimed is:

1. A pharmaceutical composition comprising a voltage gated calcium channel modulator comprising an amino acid sequence selected from:
MVRFGDELGGRYGGPGGGERARGGGAG-GAGGPGPGGLQPGQRVLYKQSI AQRARTMA-LYNPIPVKQNCFTVNRSLFVFSEDNV-VRKYAKRITEWP (SEQ ID NO: 1); NT$_B$ (45-95) KQSIAQRARTMALYN-PIPVKQNCFTVNRSLFVFSEDNVVRKY-AKRITEWP (SEQ ID NO: 2); or
or NT$_B$ (56-95) MALYNPIPVKQNCFTVNRSLFVF-SEDNVVRKYAKRITEWP (SEQ ID NO: 3); wherein the modulator is effective to treat ameliorate, reduce or alleviate pain, an analgesic side effect, analgesic tolerance or symptoms thereof and a pharmaceutically acceptable excipient.

2. The pharmaceutical composition of claim 1, wherein said composition enhances potency of an opioid agonist.

3. The pharmaceutical composition of claim 1, further comprising an opioid analgesic.

4. The pharmaceutical composition of claim 3, wherein the opioid analgesic is morphine, hydrocodone, oxycodone, codeine, fentanyl, alfentanil, hydromorphone, meperidine, methadone, oxymorphone, propoxyphene, or tramadol.

5. An isolated peptide consisting of the amino acid sequence SEQ ID NO:1, SEQ Is NO:2, or SEQ ID NO:3.

6. A pharmaceutical composition comprising a voltage gated calcium channel modulator consisting of amino acid sequence: MVRFGDELGGRYGGPGGGERARGGGAG-GAGGPGPGGLQPGQRVLYKQSI AQRARTMALYN-PIPVKQNCFTVNRSLFVFSEDNVVRKYAKRITEWP (SEQ ID NO: 1); NT$_B$ (45-95) KQSIAQRARTMALYN-PIPVKQNCFTVNRSLFVFSEDNVVRKYAKRITEWP (SEQ ID NO: 2); or
or NT$_B$ (56-95) MALYNPIPVKQNCFTVNRSLFVF-SEDNVVRKYAKRITEWP (SEQ ID NO: 3); wherein the modulator is effective to treat, ameliorate, reduce or alleviate pain, an analgesic side effect, analgesic tolerance or symptoms thereof and a pharmaceutically acceptable excipient.

7. A method to treat, ameliorate, reduce or alleviate pain, comprising: administering to a subject in need thereof a pharmaceutically effective amount of a composition of claim 1 or claim 6.

8. The method of claim 7, further comprising administering one or more Gβγ polypeptides.

9. The method of claim 7, further comprising administering one or more opioid agonists.

10. The method of claim 9, wherein the opioid antagonist is from about 0.1 mg to about 300 mg.

11. The method of claim 7, wherein the pain is chronic pain, neuropathic pain, or acute pain.

12. A method for enhancing the potency of an opioid agonist comprising administering to a subject in need thereof a therapeutically effective amount of the composition of claim 1 or claim 6.

* * * * *